(12) United States Patent
Stephenson

(10) Patent No.: US 9,926,342 B2
(45) Date of Patent: Mar. 27, 2018

(54) RECOMBINANT VAPA AND VAPC PEPTIDES AND USES THEREOF

(71) Applicant: John R. Stephenson, Weatherford, TX (US)

(72) Inventor: John R. Stephenson, Weatherford, TX (US)

(73) Assignee: SANTA CRUZ BIOTECHNOLOGY, INC., Dallas, TX (US)

( * ) Notice: Subject to any disclaimer, the term of this patent is extended or adjusted under 35 U.S.C. 154(b) by 0 days.

(21) Appl. No.: 14/210,326

(22) Filed: Mar. 13, 2014

(65) Prior Publication Data
US 2015/0023983 A1 Jan. 22, 2015

Related U.S. Application Data

(60) Provisional application No. 61/778,970, filed on Mar. 13, 2013.

(51) Int. Cl.
| | |
|---|---|
| *A61K 39/00* | (2006.01) |
| *A61K 39/38* | (2006.01) |
| *A61K 39/205* | (2006.01) |
| *C07K 14/195* | (2006.01) |
| *A61K 39/05* | (2006.01) |

(52) U.S. Cl.
CPC ............ *C07K 14/195* (2013.01); *A61K 39/05* (2013.01); *A61K 2039/545* (2013.01); *A61K 2039/55* (2013.01); *A61K 2039/552* (2013.01); *A61K 2039/55511* (2013.01); *A61K 2039/70* (2013.01); *C07K 2319/21* (2013.01); *C07K 2319/23* (2013.01)

(58) Field of Classification Search
CPC ......... A61K 38/00; A61K 39/00; A61K 39/02
USPC ................................ 424/184.1, 185.1, 234.1
See application file for complete search history.

(56) References Cited

U.S. PATENT DOCUMENTS

| | | | |
|---|---|---|---|
| 7,169,393 B2 | 1/2007 | Vanniasinkam | |
| 7,297,339 B2 * | 11/2007 | Hondalus ................ | A61K 39/05 424/184.1 |

FOREIGN PATENT DOCUMENTS

| | | | | |
|---|---|---|---|---|
| WO | WO2012/009774 | * | 1/2012 | ................ C12N 1/21 |

OTHER PUBLICATIONS

Becú, T. et al. Immunoprophylaxis of Rhodococcus equi pneumonia in foals. Vet. Microbiol. Jun. 16, 1997; 56(3-4): 193-204.
Benoit et al. H2O2, Which Causes Macrophage-Related Stress. Infection and Immunity Jul. 2002; 70(7): 3768-3776.
Byrne, B.A., et al. Virulence Plasmid of Rhodococcus equi Contains Inducible Gene Family Encoding Secreted Proteins. Infection and Immunity Feb. 2001; 69(2): 650-6.
Chirino-Trejo, J.M. et al. Protection of Foals Against Experimental Rhodococcus equi Pneumonia by Oral Immunization. Can. J. Vet. Res. Oct. 1987; 51(4): 444-7.
Coulson et al. Characterization of the Role of the Pathogenicity Island and vapG. Infect and Immun. Aug. 2010; 78(8): 3323-3334.
Dawson , T.R. et al. Current understanding of the equine immune response to Rhodococous equi. Vet. Immunol. Immunopathol. May 15, 2010; 135(1-2): 1-11.
Fernandez-Mora et al., Maturation of Rhodococcus equi—Containing Vacuoles is Arrested After Completion of the Early Endosome Stage. Traffic. Aug. 2005; 6(8): 635-653.
Gigeure et al. Clinical manifestations, diagnosis, treatment, and prevention of Rhodococcus equi infections in foals. Vet microbial. 1997; 56: 313-34.
Gigeure, S. Role of the 85-Kilobase Plasmid and Plasmid-Encoded Virulence-Associated Protein A in Intracellular Survival. Infection and Immunity Jul. 1999; 67(7): 3548-57.
Gigeure et al. Modulation of Cytokine Response of Pneumonic Foals by Virulent Rhodococcus equi. Infection and Immunity Oct. 1999; 67(10): 5041-5047.
Giguere, Evaluation of a commercially available hyperimmune plasma product for prevention of naturally acquired pneumonia. J. Am. Vet. Med. Assoc. Jan. 1, 2002; 220(1): 59-63.
Higuchi et al., Effect of Prophylactic Administration of Hyperimmune Plasma to Prevent Rhodoccus equi Infection of Foals. Zentralbl Veterinarmed B. Nov. 1999; 46(9): 641-648.
Hines and Hitela. Rhodococcal pneumonia: humoral versus cell-mediated immunity. Equine Vet J. Sep. 1996; 28(5): 339-340.
Holznagel et al., Onset of immunoglobulin production in foals, Equine Vet. J. Sep. 2003; 35(6): 620-622.
Hondalus et al. Survival and Replication of Rhodococcus equi in Macrophages. Infection and Immunity Oct. 1994; 62(10): 4167-4175.
Hooper-McGrevy et al. Evaluation of equine immunoglobulin specific for Rhodococcus equi virulence-associated proteins A and C. Am J Vet Res. Aug. 2001; 62(8): 1307-1313.
Hooper-McGrevy K.E. et al. Immunoglobulin G Subisotype Response of Pneumonic and Healthy, Exposed Foals and Adult Horses. Clin. Diagn. Lab Immunol. May 2003; 10(3): 345-51.

(Continued)

*Primary Examiner* — Rodney P Swartz
(74) *Attorney, Agent, or Firm* — John P. White; Cooper & Dunham LLP

(57) ABSTRACT

The present invention provides a recombinant protein comprising consecutive amino acids, the sequence of which is substantially identical to a sequence of amino acids present in a *Rhodococcus equi* virulence-associated protein and compositions containing fusion proteins of the invention. The present invention also provides uses of the compositions in the manufacture of hyperimmune plasma against *Rhodococcus equi*, in producing a hyperimmune plasma against *Rhodococcus equi* in protecting an animal against *Rhodococcus equi* and in protecting a newborn animal against *Rhodococcus equi*.

25 Claims, 2 Drawing Sheets

(56) References Cited

OTHER PUBLICATIONS

Hooper-McGrevy, K.E. et al., Virulence-associated protein-specific serum immunoglobulin G-isotype expression in young foals . . . , Vaccine. Dec. 30, 2005; 23(50): 5760-7.
Hurley, J.R. Failure of hyperimmune plasma to prevent pneumonia caused by Rhodococcus equi in foals, Aust. Vet. J. Nov. 1995; 72(11): 418-20.
Jacks, et al. In Vivo Expression of and Cell-Mediated Immune Responses to the Plasmid-Encoded Virulence-Associated Protein. Clin. Vaccine Immunol. Apr. 2007; 14(4): 369-374.
Jain, S., Deletion of vapA encoding Virulence Associated Protein A attenuates the intracellular actinomycete Rhodococcus equi, Mol. Microbio. Oct. 2003; 50(1): 115-28.
Léguillette, R. et al. Equine Respiratory Disease, Jan. 2002; Document No. B0329.0102.
Letek et al. Evolution of the Rhodococcus equi vap Pathogenicity Island Seen through Comparison of Host-Associated vapA and vapB. J Bacteriol. Sep. 2008; 190(17): 5797-5805.
Letek, M. et al. The Genome of a Pathogenic Rhodococcus: Cooptive Virulence Underpinned by Key Gene Acquisitions. PLosS Genet. Sep. 30, 2010; 6(9). pii:elOOI 145.
Lopez, A.M. Identification of Pulmonary T-Lymphocyte and Serum Antibody Isotype Responses Associated with Protection . . . , Clin. Diagn. Lab. Immunol. Nov. 2002; 9(6): 1270-6.
Lopez et al. Analysis of anamnestic immune responses in adult horses and priming in neonates induced by a DNA vaccine. Vaccine. Sep. 8, 2003; 21(25-26): 3815-3825.
Lopez et al. Safety and immunogenicity of a live-attenuated auxotrophic candidate vaccine against the intracellular pathogen Rhodococcus. Vacine. Feb. 13, 2008; 26(7):998-1009.
Lührmann, A. et al. Necrotic Death of Rhodococcus equi-Infected Macrophages Is Regulated by Virulence-Associated Plasmids. Infection and Immunity Feb. 2004; 72(2): 853-62.
Martens, R. J. et al. Rhodococcus equi foal pneumonia: Protective effects of immune plasma in experimentally infected foals. Equine Vet J. Jul. 1989; 21(4), 249-255.
Meijer and Prescott. Rhodococcus equi. Vet res. Jul.-Aug. 2004; 35(4): 383-396.
Muscatello, G. Rhodococcus equi pneumonia in the foal—Part 1: Pathogenesis and epidemiology. Vet J. Apr. 2012; 192(1): 20-6.
Muscatello, G. Rhodococcus equi pneumonia in the foal—Part 2: Diagnostics, treatment and disease management. Vet J. Apr. 2012; 192(1): 27-33.
Muscatello, G. et al. Rhodococcus equi infection in foals: the science of 'rattles'. Equine Vet J. Sep. 2007; 39(5): 470-8. Review.
Muscatello, G. et al. Detection of Virulent Rhodococous equi in Exhaled Air Samples from Naturally Infected Foals. J. Clin Microbiol. Mar. 2009; 47(3): 734-7.
Ocampo-Sosa, et al. Molecular Epidemiology of Rhodococcus equi Based on traA, vapA, and vapB Virulence Plasmid Markers. J. infect. Dis. Sep. 1, 2007; 196(5):763-769.
Oldreld, C. et al. Rapid determination of vapA/vapB genotype in R. equi using a differential polymerase chain reaoton. Antonie Van Leeuwenkoek. May 2004; 85(4): 317-26.
Oliviera et al. Vaccination of Mice with *Salmonella* Expressing VapA; Mucosal and Systemic Th1 Responses. PLoS One. Jan. 13, 2010; 5(1): e8644.
Pei, V. et al. Mutation and virulence assessment of chromosomal genes Rhodococcus equi 103. Can. J Vet Res, Jan. 2007; 71(1): 1-7.
Pei et al. Immunization by intrabronchial administration to 1-week-old foals of an unmarked double gene disruption strain . . . , Vet Microbiol. Nov. 15, 2007; 125(1-2): 100-110.
Prescott, J. F. Rhodococcus equi: an Animal and Human Pathogen, Clin. Microbiol. Rev. Jan. 1991; 4(1): 20-34.

Ren, J. and Prescott J.F. Analysis of virulence plasmid gene expression of intra-macrophage and in vitro grown Rhodococcus equi . . . , Vet Microbiol. Jul. 1, 2003; 94(): 167-82.
Ren J. Prescott J. F. The effect of mutation on Rhodococcus equi virulence plasmid gene expression and mouse virulence. Vet Microbiol. Nov. 15, 2004: 103(3-4): 219-230.
Russell, D.A. et al. The LysR-Type Transcriptional Regulator VirR Is Required for Expression of the Virulence Gene vapA of R. equi. J. Bacteriol. Sep. 2004; 186(17): 5576-84.
Ryan, et al. Effect of age and mitogen on the frequency of interleukin-4 and interferon gamma secreting cells in foals . . . Vet. Immunol Immunopathol. Jan. 15, 2010; 133(1), 66-71.
Takai, S. et al. Identification of 15- to 17-Kilodalton Antigens Associated with Virulent Rhodococcus equi. J Clin. Microbiol. 1991; 29(3): 439-443.
Takai, S. et al. Association between a large plasmid and 15- to 17-kilodalton antigens in virulent Rhodococcus equi. Infection and Immunity Nov. 1991; 59(11): 4056-60.
Takai, S. et al. Virulence-Associated 15- to 17-Kilodalton Antigens in Rhodococcus equi: Temperature-Dependent Expression . . . , Infection and Immunity Jul. 1992; 60(7): 2995-2997.
Takai, S. et al. Identification of Intermediately Virulent Rhodococcus equi Isolates from Pigs. J Clin Microbiol. Apr. 1996; 34(4): 1034-7.
Takai, S. et al. Expression of Virulence-Associated Antigens of Rhodococcus equi Is Regulated by Temperature and pH. Microbiol. Immunol. 1996; 40(8): 591-4.
Takai, S. et al. DNA Sequence and Comparison of Virulence Plasmids from Rhodococcus equi ATCC 33701 and 103. Infection and Immunity Dec. 2000; 68(12): 6840-7.
Takai, S. et al. Pathogenicity of Rhodococcus equi expressing a virulence-asociated 20 kDa protein (VapB) in foals. Vet Microbiol. Sep. 15, 2000; 76(1): 71-80.
Tan, C. et al. Molecular Characterization of a Lipid-modified Virulence-associated Protein of Rhodococcus equi and its Potential . . . , Can. J. Vet. Res. Jan. 1995; 59(1): 51-9.
Taouji, S. et al. Immunogenecity of synthetic peptides representing linear B-cell epitopes of VapA of Rhodococcus equi. Vaccine. Mar. 12, 2004; 22(9-10): 1114-23.
Tkachuk-Sadd, O. and Prescott J. Rhodococcus equi Plasmids: Isolation and Partial Characterization. J. Clin. Microbiol. Dec. 1991; 29(12): 2696-700.
Toyooka, K. et al. Rhodococcus equi can survive a phagolysosomal environment in macrophages by suppressing acidification . . . , J. Med. Microbiol. Nov. 2005; 54(11): 1007-15.
Van Der Geize, R. et al. The Steroid Catabolic Pathway of the Intracellular Pathogen Rhodococcus equi Is Important for Pathogenesis PLoS Pathogens. Aug. 2011; 7(8): e1002181.
Vanniasinkam, T. The immunogenicity of Rhodococcus equi GroEL2-based vaccines in a murine model. Vet. Immunol Immunopathol. Mar. 2004; 98(1-2): 91-100.
Vanniasinkam, T. Immune response to vaccines based upon the VapA protein of the horse pathogen, Rhodococcus equi . . . , Int. J. Med. Microbiol. Jan. 2005; 294(7): 437-45.
Von Bargen, K. and Haas, A. Molecularand infection biologyof the horse pathogen Rhodococcus equi. FEMS Microbiol. Rev. Sep. 2009; 33(5): 870-91.
Von Bargen, K. et al. Rhodococcus equi Virulence-Associated Protein A Is Required for Diversion of Phagosome Biogenesis . . . Infection and Immunity Dec. 2009; 77(12): 5676-5681.
Wall, D. M., et al.Isocitrate Lyase Activity Is Required for Virulence of the Intracellular Pathogen Rhodococcus equi. Infection and Immunity Oct. 2005; 73(10), 6736-6741.
Zink, M.C. et al. Electron Microscopic Investigation of Intracellular Events after Ingestion of Rhodococcus equi . . . , Vet. Microbiol. Aug. 1987; 14(3): 295-305.

* cited by examiner

FIGURE 1

RECOMBINANT VAPA AND VAPC PEPTIDES AND USES THEREOF

This application claims benefit of U.S. Provisional Application No. 61/778,970 filed Mar. 13, 2013, the contents of which is hereby incorporated by reference in its entirety.

REFERENCE TO SEQUENCE LISTING

This application incorporates-by-reference nucleotide and/or amino acid sequences which are present in the file named "141006_5102_83154_SequenceListing_DH.txt," which is 49 kilobytes in size, and which was created Sep. 30, 2014 in the IBM-PC machine format, having an operating system compatibility with MS-Windows, which is contained in the text file filed Oct. 6, 2014 as part of this application.

Throughout this application, various publications are referenced by author and publication date within parentheses. Full citations for these publications may be found at the end of the specification or at the end of each experimental section. The disclosures of these publications are hereby incorporated by reference into this application to describe more fully the art to which this invention pertains.

FIELD OF THE INVENTION

The present invention relates to a recombinant VapA protein and a recombinant VapC protein that can be used as a vaccine, with or without the administration of hyperimmune plasma (HIP) in foals, to protect against *Rhodococcus equi* in vertebrates.

BACKGROUND

*R. equi* Infection

A significant endemic pathogen that affects the equine breeding industry is the facultative bacterial pathogen, *Rhodococcus equi*. The intracellular bacteria are part of the mycolic acid-containing group of actinomycetes, which includes *Corynebacterium, Mycobacterium*, and *Nocardia* (Embley et al., 1994). *R. equi* is an opportunistic bacterium that is abundant in soil and herbivore manure and takes advantage of the underdeveloped immune system of 1-6 month old foals (Giguere et al., 1997). This can lead to pyogranulomatous bronchopneumonia, resulting in death of the foals if not treated (Giguere et al., 1997). Foals, sheep, pigs, goats, cattle and immunocompromised humans are all vulnerable to infection by *R. equi*, with foals being the primary host (Prescott, 1991). Infected swine and cattle develop pyogranulomatous adenitis, whereas other species develop pneumonia and pulmonary lesions, followed by a disruption of the bronchial and mesenteric lymph nodes, which is similar in infected foals (Prescott, J F 1991; von Bargen and Haas, 2010). Foals are infected with *R. equi* when they inhale aerosolized bacteria particles from contaminated feces, dust, or from the exhalations of contaminated foals; *R. equi* multiplies in the intestine and disseminates into the environment through fecal matter (Muscatello et al., 2007; Muscatello et al., 2009; von Bargen and Haas, 2010). Alveolar macrophages phagocytize inhaled *R. equi* and form an *R. equi* containing vacuole (RCV), documented to block the phagosome-lysosome fusion, inhibit acidification and prevent any further maturation of the vacuole (Zink et al., 1987; Fernandez-Mora et al., 2005). The RCV environment allows *R. equi* to multiply and survive, resulting in necrotic death of the macrophage and the formation of granuloma as *R. equi* proliferates (Toyooka et al., 2005; Lührmann et al., 2004).

Immune Response to *R. equi*

Research suggests that foals are susceptible to *R. equi* and cannot clear an infection due to their underdeveloped innate, humoral and cell mediated immune responses in comparison to adult horses. *R. equi* is cleared with a combination of interferon (IFN) gamma-activated macrophages and opsonizing antibodies enhanced by CD4+ T cells (Cauchard et al., 2004; Dawson, 2010). However, it has been demonstrated that foals have a lag synthesis of IgGb antibodies and low levels of IFN gamma that induce an intracellular response (Sheoran et al., 2000; Holznagel et al, 2003; 2000; Breathnach et al., 2006; Ryan et al., 2010). The waning of maternal antibodies and the low levels of IgGb, which are important factors in combating bacterial and viral pathogens, may also contribute to the susceptibility of foals to *R. equi* (Hines and Hitela, 1996; Wagner, 2006; Dawson et al., 2010). To clear an *R. equi* infection a T-helper (TH1) cell-mediated response characterized by IFN gamma induction is required, yet due to an immature immune system, foals mount a T-helper (TH2) cell mediated response characterized by IL-4 induction, which is detrimental to the foals and may lead to the development of clinical pneumonia (Giguere et al., 1999 (5041-5047); Breathnach et al., 2006; Dawson et al., 2010; Ryan et al., 2010). Other limiting factors that increase *R. equi* susceptibility in foals include decreased killing activity of neutrophils, deficient toll-like receptors on macrophages and Cytotoxic T lymphocytes (CTLs) (Dawson, 2010). Foals have low Major Histocompatibility class II (MHC II) expression and CD 1b levels by antigen-presenting cells, which also play an important role in the clearance of pathogens in adult horses (Dawson, 2010).

Treatment Against *R. equi*

A combination of lipophilic antimicrobial agents can be used as therapy for an extended period of time to treat *R. equi* infected foals because they have the ability to penetrate cells and target intracellular pathogens (Prescott, 1991). One common treatment combination consists of rifampin and erythromycin but in the last few years, resistance to this combination has been rising and prolonged antimicrobial therapy should be avoided (Buckley et al., 2007; Takai et al., 1997). The use of rifampin or erythromycin alone is not recommended because the efficacy of erythromycin in an intracellular environment is poor, and the combination of the two optimizes protective effects (Nordmann et al., 1992; Prescott and Sweeney, 1985). In recent years macrolides such as, azithromycin and clarithromycin, have replaced erythromycin in the antimicrobial combination as they have less adverse side effects and are administered less frequently (Giguere et al, 2004). Resistance to macrolides is a problem that has surfaced. When resistance to one macrolide occurs the organism is usually resistant to many other macrolides (Cohen, 2006). Another method to prevent an *R. equi* infection is administration of *R. equi*-specific hyper immune plasma (HIP) to foals. HIP provides all-around antibodies against *R. equi* and other factors that induce an immune response, however, it is reported to have variable results (Martens et al., 1989; Hurley and Begg, 1995; Higuchi et al., 1999; Giguere et al., 2002; Perkins et al., 2002). Although the exact component of HIP that provides protection in unknown, VapA and VapC antibodies are claimed to be critical, in addition to other immune components (Hooper-McGrevy et al., 2001; Lopez et al., 2002). Antibiotics have helped treat *R. equi* infections but they are not a long-term solution due to antibiotic resistance and side effects.

Human Susceptibility to *R. equi*

An *R. equi* infection is rare in healthy humans and only present in immunocompromised patients with symptoms such as cavitated bronchopneumonia, commonly accompanied by fever, dyspnea, lung lesions, chest pain and a nonproductive cough (Cinque et al., 2011; Prescott, 1991). Infection of *R. equi* in AIDs patients occurs when CD4+ helper T cells are less than 100 cells/µl (Muscatello, 2012). As of 2010, approximately 34 million people live with HIV/AIDS globally and HIV/AIDS resulted in about 1.8 million deaths in 2010 (WHO HIV/AIDS Data and Statistics, 2010). The first *R. equi* infection in a human was reported in 1967 and only 15 additional cases were reported until 1983 (Golub et al., 1967; van Etta et al., 1983; Eiguchi et al., 2009; Petrosillo et al., 2010). There has been a steady increase of *R. equi* infections since 1983, primarily due to the increase in HIV infection, organ transplantations and cancer treatments (Weinstock and Brown, 2002). By 2010, more than 200 cases of *R. equi* infection in immunocompromised individuals were reported worldwide (Topino et al., 2010; Yamshchikov et al., 2010). Human infection occurs via the same route in humans as in foals (Schlusselhuber et al., 2011). Among HIV-infected patients, the mortality rate due to *R. equi* is within a 50-55% range and within a range of 20-25% among non-HIV immunocompromised patients (Weinstock and Brown, 2002; Schlusselhuber et al., 2011).

Human Treatment Against *R. equi*

Introduction of highly active antiretroviral therapy (HAART) in the 1990's has decreased the mortality rate of HIV patients infected with *R. equi*, with some reporting a survival rate of 100% (Torres-Tortosa et al., 2003; Yamshchikov et al., 2010). No standard treatment for *R. equi* in humans exists but treatment with a combination of at least two antibiotics is commonly used. *R. equi* is susceptible to: rifampin, carbapenems, aminoglycosides, glycopeptides, floroquinolones, macrolides, tygecicline and linezolid (El Karoui et al, 2009; Russo et al., 2010; Ferretti et al., 2011). Treatment with antibiotics over time has led to higher doses required for treating HIV-infected people because some *R. equi* strains are showing resistance to commonly used antibiotics, including penicillins (Weinstock and Brown, 2002).

*R. equi* Plasmids

The phylogenetically diverse *Rhodococcus* genus consists of pathogenic species that affect plants or animals and non-pathogenic species that are found in the environment. *R. equi* carry different types of plasmids with genes that aid in the survival of both the environment and hosts (Bell et al., 1998; Gürtler et al., 2004). Virulent *R. equi* strains carry an 80-90 kb plasmid critical for virulence, intracellular replication, and survival (Takai et al., 1991; Tkachuk-Saad and Prescott 1991; Giguere et al., 1999). Loss of the plasmid results in an avirulent strain unable to replicate in the macrophage (Hondulas et al., 1994; Giguere, et al., 1997). The virulence plasmid is divided into four regions: replication and partition, conjugation, pathogenicity island (PAI), and an unknown area (Takai et al., 2000; Letek et al., 2008). Polymerase chain reaction (PCR) analysis demonstrates that plasmidless non-pathogenic *R. equi* strains are common in the environment with virulent plasmids organized into three different categories, vapA+, vapB+, or vapAB-negative, based on the presence of the virulence associated protein genes, vapA and vapB. Research demonstrates that vapB+ plasmids were found in pig isolates, vapA+ plasmids were found in horse isolates and vapAvapB-plasmids were found in bovine isolates (Oldfield et al., 2004; Ocampo-Sosa et al., 2007). All three different plasmids were detected in human isolates with vapA and vapB not occurring on the same plasmid (Ocampo-Sosa et al., 2007). Both vapA+ plasmids and vapB+ plasmids have a conserved housekeeping backbone and a PAI that encodes different vap genes, which are upregulated when the organism invades the macrophage (Letek et al., 2008). The PAI in vapB+ plasmids consists of six full length vap genes: vapB, -J$_y$, -K1, -K2, -L, and vapA+ plasmids consist of six full length vap genes: vapA, -C, -D -E, -G, -H, and three vap pseudogenes vapF, -I, -X (Takai et al., 2000; Letek et al., 2008). The VapA protein has varying percent identity to the other Vap proteins (Table 1; FIG. 1), with the highest percent identity to the VapB protein, also observed in Letek et al, 2008. The VapC protein also shows varying percent identity to the other Vap proteins (Table 1; FIG. 1), with the highest percent identity to the nonfunctional protein, VapF, also observed in Letek et al., 2008. Phylogenetic analysis of the Vap amino acid sequences demonstrates that VapA and VapB are most closely related, in comparison to the other vaps, and share a common ancestral yap gene (Letek et al., 2008).

TABLE 1

Comparison of full length *R. equi* VapA and VapC protein sequences against other full length *R. equi* Vap proteins:

| *R. equi* Vap protein | SEQ ID No: | NCBI Accession number of *R. equi* Vap protein | Percent amino acid sequence identity with *R. equi* VapA | Percent amino acid sequence identity with *R. equi* VapC |
|---|---|---|---|---|
| A | 1 | NP_066765 | 100 | 58 |
| B | 2 | YP_002149601 | 75 | 55 |
| C | 3 | NP_066767 | 58 | 100 |
| D | 4 | NP_066768 | 55 | 43 |
| E | 5 | NP_066772 | 40 | 48 |
| F | 6 | NP_066773 | 50 | 65 |
| G | 7 | NP_066755 | 46 | 56 |
| H | 8 | NP_066759 | 39 | 55 |
| I | 9 | ADI50249 | 52 | 22 |
| J | 10 | YP_002149592 | 40 | 56 |
| K1 | 11 | YP_002149595 | 53 | 54 |
| K2 | 12 | YP_002149598 | 53 | 54 |
| L | 13 | YP_002149597 | 44 | 54 |
| M | 14 | YP_002149599 | 56 | 58 |
| X | 15 | — | 43 | 47 |

Sequences were analyzed using the BLAST algorithm.
Results expressed as a dash (—) indicate that there is not a curated sequence available from NCBI.

SEQ ID No. 1:
MKTLHKTVSKAIAATAVAAAAMIPAGCANATVLDSGSSSAILNSGAGSGIVGSGSYDSSTTSLNLQK

DEPNGRASDTAGQEQQYDVHGDVISAVVYQRFHVFGPEGKVFDGDAGGLTLPGAGAFWGTLFTNDLQR

LYKDTVSFQYNAVGPYLNINFFDSSGSFLGHIQSGGVSTVVGVGGGSGSWHNA

-continued

SEQ ID No. 2:
MMKALHKTVSRAIAAIATAAAAVLAVAPASVANAAVLDSGGGSALLKDGAGSGEVGSQAYDSSTVSSN

LQKAETNGPVGLAGTAEQEQQYDVHGNVISAAVYQKFHVYGPEDMVFDGDAGGLTIPGAGAFWGTLFT

SDLQRLYKDTVSFQYNALGTYLNINFFDSSGGFLGHIQAGAVSAVVGVGGGSGSWHNWEVA

SEQ ID No. 3:
MFRVGRPSKSIAVVASVLCFLALGGTARANVVAPSAWGGAQSAADKEGEGVTLGGVGVLRPHNKDADE

QYVHGVVVSALFYNHLRISVDGGMTFDGDGGGLSTPGGGALWGTLTTSDLQQLYDETASFECNAVGPY

LNINFYDSYGRILASVQAGGVSTMIGIGGGNGRWHLV

SEQ ID No. 4:
MVRARAFGRLFTFLLAVAVIATVSMGGANAQELAGTKTSDAALLSGNKAAIPEDKEYDVSGRVVSALV

YQYFIVTVDDAEDKKGKTFQGDAGGVTIPGVDFFWGTLHTPDLEKLYSDTVSFQYNAAATFLNINFFD

SKGERLGYVLAGAAGTVSGIGGGTGGWE

SEQ ID No. 5:
MTTVHKKASKAIAFTVALRLPFAGTAVALVLIALTIVAAPTGIAGAREIGAQAWPASQLESGLAVSGN

PVGVHDVRMAVHDDSTHTREFKEDDSEKQYPVHGFASSFIFYQTVSIIIDDDGRGGPGKTFEGEAGGI

TTPGAAGYAGVLFTSDLERLYRETVSFEYNAVGPYLNINLFAGDGGLLGHVQSGAISSLVGIGGGTGA

WR

SEQ ID No. 6:
MIEYAWYGPSIQSNRCCGDCPILLALGGHRTCRLATPSAWVGTPSAAGKVLPPINNNADEQYAVHGVV

FSAVFYNHVRISVDGGMTEDGEGGGLSTPGGGALWGNLMTSDLLCSSYTTKLRRSNVIWPVSKDQLLR

QLWWHSWECSRERC

SEQ ID No. 7:
MSVRTLLAATLVAGISVLAPAGIANAETSMVSTTAASSVEHAANTYDFAEAKSGSSIPAKVAAEQANS

YSVHGLVTSLAVYQHFSLTVEGGGKTFTGDSGGISIPGVAVLEGTLFTEDLQHLYSDTVSFEYNAVGP

YLNINFFDSHGTLLGHVQSGSIGTVSGIGGGTGGWQ

SEQ ID No. 8:
MNLSKTTRKFLSRTAVPATFVMALTVPWGCAAPPPLPDGPTHDLPTWREEGANYSDGTMLVRASSNFL

EPSTHSDSGQQQWTVQGVLASALVYQRLKLNVEGGETFEGYAGGLSEPGGAMVWGTLFTDNIQRLYDR

TESFEFNAVGPYLNVNFFDGHSAILGHAQLGGVSSVIGIGGGTGTWIGDVA

SEQ ID No. 9:
MPIALTAVALPAGMASAQEMGDHAWSGSRAESDVAVLGKAESAHDDPSLRTPKLKKSNSGNQYRYTVL

LSSFIFYQTLSI

SEQ ID No. 10:
MNLAHVTRKFLVSTAVPVTLVIAFAAPFQFSAPLASAATSDLSIRRDGSAHYSDSTLSLRASSDSPEP

TTHGAQQQWAVHGVLASALVYQLLTLTVDGGEQFQGYAGGVSFPGGAAVWGTLFTDDIQRLYDQTASF

QFNAVGPYLNVNFFDRHGTLLGHAQLGGVSSVIGIGGGSGTWTGDVA

SEQ ID No. 11:
MGNARRSWVKAAAAATLTAAAVMVPAGLANAQPLDVGGSSTVVANDAFGSVSLGGHGSSGYGSSSDYG

SSSDYDGSGSGFGTAPDVRSQVAASLDEEQQYDVKGDVWSALVYQQFHVEGPQGKVEDGQAGGLTIPG

AGAFWGTLFTSDLNRLYADTSSFQYNAVGPYLNINFFDGNGVLLGHIQAGAVSTVTGVGGGTGSWS

SEQ ID No. 12:
MGNARRSWVKAAAAATLTAAAVMVPAGLANAQPLDVGGSSTVVANDAFGSVSLGGHGSSDYGSSSDYG

SSSDYDGSGSGFGTAPDVRSQVAASLDEEQQYDVKGDVWSALVYQQFHVEGPQGKVFDGQAGGLTIPG

AGAFWGTLFTSDLNRLYADTSSFQYNAVGPYLNINFFDGNGVLLGHIQAGAVSTVTGVGGGTGSWS

-continued

SEQ ID No. 13:
MRPQSSYRPYVRAIFAAALVAGISILGATGVVNAETSMASNAATSTVHRVAKTCDSNLSENDHSSAET

NGQLSFATEATAEQGYTYSVHGLVTSLAVYQHFSLTVEDDGKTFTGDSGGISVTGVAVLKGTLFTEDL

QRLYNDTVSFQYNAVGPYMNINFFDSHSTLLGHVQSGSIGTLTGIGGGTGGWR

SEQ ID No. 14:
MIRTVVGWGAFVLAFSILATGAAYAHAQELEPGGSFSEGILQRNFPLEGEFASVSEPGSGNVSASKVG

EESNFAVRGVVVSALFYQHLEITVSGGETEDGDGGGLSVPGGGALWGTLFTRDLQRLYDETVSFEFNA

AGLFVNVNFFDKDGILLGHVESGAVSTAVGIGGGTGRWHIV

SEQ ID No. 15:
RLYDETGPFDFNAAGLFMNVDHFGYRA

Expression of Vaps

Environmental signals such as temperature, pH, magnesium and iron concentration, and/or oxidative stress are documented to regulate the expression of most vap genes on the PAI of equine isolates. VapA, an essential virulence protein of R. equi found in equine isolates, is a 15-17 kDa surface expressed lipoprotein linked to the cell wall through a lipid-modified N-terminal which is regulated by pH and temperature (Takai et al., 1991 (439-443); Takai et al., 1992 (2995-2997); Tan et al., 1995; Giguere et al., 1999; Jain et al., 2003). The function of vapA is unknown, however it is thought to help prevent fusion between the RCV and lysosomes (Fernandez-Mora et al., 2005; Toyooka et al., 2005; von Bargen et al., 2009(5676-5681)). Expression of vapA is highly induced by macrophage related stress, and reported that its deletion prevents R. equi replication in macrophages without affecting macrophage attachment (Benoit et al., 2002; Jain et al., 2003; Jacks et al., 2007). Transcription of vapA is regulated by two genes in the PAI: virR, a LysR-type regulator, and orf8, a two component response-like regulator; the absence of either gene decreases virulence of R. equi (Takai et al., 2000; Ren and Prescott, 2003; Russell et al., 2004). Although vapA has been claimed to be essential for virulence, both vapA and the plasmid have been reported to be necessary for virulence in foals (Jain et al., 2003; Giguere et al., 1999). VapB, present in non-equine isolates, is reported to be a surface expressed 20 kDa lipoprotein with a similar structure to vapA (Takai et al., 2000 (71-80); Byrne et al., 2001; Letek et al., 2008). Plasmids that carry vapB are less virulent than plasmids that encode vapA and are categorized as intermediately virulent (Takai et al., 1996; Takai et al., September 2000).

VapC, a secreted protein, and VapA are reported to induce the strongest lymphoproliferative response in foals and adult horses infected with R. equi in comparison to other Vaps; both demonstrate the highest upregulation of the vap genes in macrophages in vitro (Hooper-McGrevy et al., 2003; Ren and Prescott, 2003; Jacks et al., 2007). The non-functional secreted protein VapD is highly induced due to macrophage related stress (Benoit et al., 2002; Ren and Prescott, 2003). VapG, a pH regulated protein that is secreted and may also be surface localized, is highly upregulated in foal macrophages, which is thought to be a response to stress within macrophages (Coulson et al., 2010). vapG has no effect on the intracellular replication of R. equi, and may play an important role in the initial host-pathogen interaction, or help disperse the pathogen from the lungs after a respiratory infection (Jain et al., 2003; Coulson et al., 2010). Expression of both vapD and vapG are induced through macrophage related stress and environmental signals, which are important pathophysiological factors in the virulence of R. equi (Benoit et al., 2002; Jacks et al., 2007; Coulson et al., 2010). The function of VapE, a secreted protein, and VapH are also unknown (Byrne et al, 2001). VapC, -D, and -E are low-molecular-mass immunogenic proteins that are thermoregulated and expressed at 37° C., in synchrony with VapA; coordinated regulation of multiple proteins is an important sign of virulence (Tan et al., 1994; Takai et al., 1996; Byrne et al., 1999; Byrne et al., 2001). The three vaps -F, -I, and -X, are non-functional proteins with unknown cellular locations (Meijer and Prescott, 2004; Cauchard et al., 2006; Polidori and Hass, 2006). vapI has been demonstrated to be unnecessary for the replication and survival in mouse macrophages and was observed to be upregulated by 6-fold when R. equi was grown in host cells (Polidori and Hass, 2006). Amino acid sequence analysis demonstrates that Vap proteins have high homology in their C-terminal domain, with the exclusion of VapF (Takai et al, 2000 (6840-6847). Although all yap genes are upregulated when R. equi is grown in equine macrophages, it was demonstrated that vapA, -D, and -G are greatly induced by macrophage related stress, and expressed at significantly higher levels in the lungs of infected foals (Benoit et al., 2002; Jacks et al., 2007; Coulson et al., 2010). When mutated, chromosomally encoded genes such as, nitrate reductase gene narG, isocitrate lyase gene aceA, high temperature requirement protein A gene, and the phoPR operon genes have demonstrated increased virulence or attenuation of R. equi, and are suggested to play a role in R. equi virulence in addition to the yap genes (Ren and Prescott, 2004; Wall et al., 2005; Pei et al., 2007). Furthermore, microarray and transcription network analysis demonstrate that plasmid encoded genes interact with housekeeping genes and cross-talk between the plasmid-chromosome genes, which is necessary for intracellular proliferation of R. equi (Letek et al, 2010). Table 2 summarizes the characteristics of each of the yap genes and their corresponding proteins.

TABLE 2

Characteristics of R. equi vap genes and corresponding Vap proteins:

| R. equi Vap protein | Plasmid Category | Cellular location of protein | Encoded by a pseudogene | Known method of gene regulation | Gene important for replication |
|---|---|---|---|---|---|
| A | vapA+ | surface | no | Thermo/pH | Yes |
| B* | vapB+ | surface | no | — | — |
| C | vapA+ | secreted | no | Thermo | — |
| D | vapA+ | secreted | no | Thermo/pH | — |
| E | vapA+ | secreted | no | Thermo | — |
| F | vapA+ | not secreted | yes | — | No |

TABLE 2-continued

Characteristics of R. equi vap genes and corresponding Vap proteins:

| R. equi Vap protein | Plasmid Category | Cellular location of protein | Encoded by a pseudogene | Known method of gene regulation | Gene important for replication |
|---|---|---|---|---|---|
| G | vapA+ | secreted** | no | Thermo/pH | — |
| H | vapA+ | secreted | no | — | — |
| I | vapA+ | secreted | yes | — | — |
| J | vapB+ | — | — | — | — |
| K1 | vapB+ | — | — | — | — |
| K2 | vapB+ | — | — | — | — |
| L | vapB+ | — | — | — | — |
| M | vapB+ | — | — | — | — |
| X | vapA+ | — | yes | — | — |

Results expressed as a dash (—) indicate there is insufficent evidence from which to draw a reasonable conclusion.
*VapB has only been observed in non-equine isolates.
**May also be surface expressed.

R. equi Vaccine Attempts

Recombinant VapA and VapC proteins have been used in several studies to test antibody levels against R. equiR. equi, and as immunogens to protect foals against an R. equiR. equi infection, or in donors for plasma production. Although a number of strategies have been studied and tested to develop an R. equiR. equi vaccine, a successful commercial vaccine has yet to be developed.

In the Chirino-Trejo 1987 study, protection of foals immunized orally against experimental R. equiR. equi was studied. Two strains of R. equiR. equi were used for immunization; one strain being a clinical isolate from a pneumonic foal (2523-85; CR +R) and the other a laboratory passaged Congo red negative (CR −R) variant of the same strain which differed in the absence of a dominant 17.5 kd and minor 15kd protein. This choice was made because in other facultative intracellular pathogens Congo red staining has been associated with virulence.

Two groups of three 1 to 3 week old foals were immunized administration of CR−R and CR+R via a stomach tube once a week for four weeks. The first group was immunized with 100 mL phosphate buffered saline containing 10^9-10^10 of CR+R. equiR. equi and the second group with 100 mL phosphate buffered saline containing 10^9-10^10 of CR −R. equiR. equi. Three non-immunized foals were used as controls. All foals were challenged three weeks after immunization, via aerosol infection with about 18 mL of about 10^10 of the pneumonic foal isolate. Additional aerosol exposure was performed on days 1, 2, 6, and 7 of the study (the first day of challenge being designated as day 0).

Foals in the control group were euthanized ten days after initial challenge day, along with one foal from each immunization group. The remaining foals were euthanized on day 14. The lungs of non-immunized foals showed signs of pneumonia, the lungs of one CR+ foal, sacrificed at the same day as the controls, showed areas of patchy consolidation which were significantly lower than that of the control foals. The lungs of the CR− foal, sacrificed at the same day as the controls, were congested and firm. The lungs of the CR+ and CR− foals euthanized on day 14 were congested but otherwise normal.

The procedure described for immunization appeared safe for foals but cannot be used on farms with endemic R. equiR. equi pneumonia problems. As described by Takai S et al. 1986, the multiplication of R. equiR. equi in intestine of foals causes dissemination of large numbers of virulent R. equiR. equi if administered by stomach tube. Therefore, natural infection will not be adequate to protectively immunize foals and an artificial immunization is required. Chirino-Trejo 1987 acknowledged that further studies must take place to identify the exact protective antigens and explore parental immunization.

Becú et al., 1997 performed a four-year study in Argentina to test the protection against R. equiR. equi pneumonia in foals via active and passive immunity. In field trial 1, between 700 and 1200 thoroughbred mares from 14 to 22 different farms were vaccinated with an R. equiR. equi vaccine containing many different antigens, including 'equi factors' and virulence associated protein VapA provided by Dr. J. F. Prescott. In the first two years (1992 and 1993), the mares were vaccinated at 45, 30, and 15 days prior to parturition. In the second two years (1994 and 1995), the mares were vaccinated at 30 and 15 days prior to parturition. From this group, 700 to 800 foals every year received only passive immunity.

In field trial 2, mares were vaccinated as described above. Foals with poor passive immunity were administered hyperimmune plasma (HIP) intravenously at 4 days of age. On two of the farms, all foals were administered HIP at 4 days of age. All 380 foals in this trial were given HIP at 25 days of age.

53 foals were used in field trial 3 and were divided up into three separate groups. The 33 foals in Group A were from vaccinated mares and all received HIP at 25 days of age. Five of these foals had poor passive transfer and were also administered HIP at 4 days of age. The ten foals in Group B were from non-vaccinated mares and were not administered HIP. These foals were immunized at 20, 30, and 40 days of age with 0.5 mL of the R. equiR. equi vaccine. The ten foals in Group C were from non-vaccinated mares and were neither given HIP nor vaccinated.

The immune response of all foals was tested until the foals were 90 days of age. The mortality from R. equiR. equi pneumonia in the foals from vaccinated dams dropped from an average of 3% to 1.2% in the 4 years of the study. The average mortality due to R. equiR. equi in foals administered HIP dropped from 5.8% to 0.2%. Active vaccination of foals from vaccinated mares on an enzootic farm at 20, 30, and 40 days of age did not protect them from mortality due to R. equiR. equi pneumonia. Becú et al., 1997 concluded that using their vaccine in a program of mare vaccination before parturition on enzootically affected farms significantly reduced morbidity and mortality. Furthermore, more complete control of enzootic pneumonia due to R. equiR. equi was achieved by administration of hyperimmune plasma to foals with low levels of antibodies to the vaccine antigens.

Hines et al. 2001 studied the hypothesis that horses develop an antigen-specific recall response after exposure to R. equiR. equi early in life, and can use this response to successfully clear R. equiR. equi bacteria when challenged. Twelve clinically healthy adult horses were used in this study over two consecutive summers. Representing a variety of breeds, the age of the horses ranged from 2 to 18 years. Three weekly bronchoalveolar lavages (BALs) were performed on each horse. During the first BAL procedure, the right lung of the horses was administered 2×10^7 R. equiR. equi strain ATCC 33701 per mL of PSB. The BAL procedure was repeated 7 and 14 days post-challenge, but no additional R. equiR. equi was administered.

Following each BAL procedure, the horses were placed in an isolated stall for one week after challenge and monitored for any changes in rectal temperature, respiration, or pulse. Any horse with a fever was further examined, including auscultation of the lungs using a re-breathing bag. Blood was taken from the horses vial jugular venipuncture on the day of each BAL procedure. Blood counts and fibrinogen levels were analyzed.

Using a pMal vector, Hines et al. 1996 constructed a recombinant VapA (rVapA) protein fused with maltose binding protein (MBP). The rVapA protein was used to study the lymphoproliferative response in BALF cells and PBMC from pre- and post-challenged horses. Prior to challenge with *R. equiR. equi*, most horses had minimal responses to rVapA protein; however, after challenge, the horses showed antigen-driven responses to rVap. From these findings, Hines et al. 1996 concluded that the administration of bacteria into the lungs led to the activation of memory T-cells with receptors for *R. equiR. equi* antigens. Support for further testing of VapA as an immunogen is associated with the recognition of VapA by T-cells of the lung.

A key study performed by Hooper-McGrevy et al. 2001, tried to determine whether immunity against *R. equi* conferred by hyperimmune plasma was mediated by antibodies against VapA and VapC. Twenty-eight 3-week old mixed breed pony foals ranging in age from 18 to 23 days were used in the study. 7 foals received 1 liter of commercially available hyperimmune plasma from whole-cell *R. equi* immunized donors (HIP) intravenously 24 hours prior to infection with *R. equi*. A second group of 7 foals received purified immunoglobulin against VapA and VapC 24 hours prior to infection. Foals were infected by administration of 25 ml of *R. equi* strain 103+ at a concentration of $5 \times 10^7$ CFU/ml into each of the major bronchi. 14 foals were used as controls in this study. Foals were euthanized 14 days after infection.

VapA and VapC recombinant proteins were produced by amplifying genes encoding VapA and VapC from the *R. equi* 103+ plasmid. Amplified products were digested and the digestions products were ligated to a similarly digested plasmid vector. Resultant plasmids were transformed into *E. coli* to allow for the in vitro production of recombinant VapA and VapC fused to glutathione-S-transferase (GST). Fusion proteins were purified using glutathione beads and VapA and VapC were cleaved from CST by use of thrombin.

Three adult horses were immunized intramuscularly 3 times at 2-week intervals with 1.5 mg each of VapA and VapC using 1 ml of aluminum hydroxide gel as the adjuvant. Three weeks after the third immunization, 4 liters of blood was collected from each horse and plasma was separated. Immunoglobulin was then precipitated from plasma, lyophilized and rehydrated in a volume of saline solution that resulted in a titer equivalent to that in the original plasma. Foals received 1 liter of this preparation intravenously 1 day prior to infection with *R. equi*. Heart rate, respiratory rate, and rectal temperature were recorded twice daily, and serum fibrinogen concentration and WBC count were determined every other day following infection.

Foals were euthanized 14 days following infection, and lung lesions and concentration of *R. equi* in lungs were assessed. The onset of clinical signs of pneumonia was significantly delayed in the HIP- and immunoglobulin-treated groups, compared with the untreated infected group. Moreover, pulmonary lesions were less severe in the treated groups, and significantly fewer *R. equi* organisms were cultured from the lungs of treated foals. Compared with untreated infected foals, severity of disease that developed following infection was reduced by administration of commercially available HIP as well as by administration of immunoglobulin purified from plasma of horses immunized with *R. equi* VapA and VapC.

Based on this study, Hooper-McGrevy concluded that immunoglobulin is the primary component of hyperimmune plasma that confers protection against *R. equi*-induced pneumonia in foals and that antibodies against *R. equi* VapA and VapC are protective. Significantly, Hooper-McGrevy observed that antibodies against VapA and VapC provided partial protection against *R. equi* induced pneumonia equivalent to that mediated by HIP. Thus, Hooper-McGrevy indicated that further studies are required to develop active immunization procedures that effectively protect foals from infection with *R. equi*.

Lopez et al. 2002 set out to test whether antibodies to VapA would be expanded 14 days post challenge in adult horses. Lopez et al., 2002 developed a His-tagged recombinant VapA protein derived from ATCC 33701 to measure Vap protein levels from 12 adult horses challenged intrabrochially with *R. equi*. Horses were challenged with $2 \times 10^7$ *R. equi* strain ATCC 33701. 14 days post challenge, titers of all VapA antibody isotypes increased significantly, but the titers of IgGb and IgGa were dramatically enhanced following challenge. Lopez et al. 2002 concluded that an effective vaccine for foals must be designed to induce IgGb and/or the T-lymphocyte responses that production of this isotype reflects.

Hooper-McGrevy et al., 2003 developed recombinant GST-tagged Vap proteins for Vap proteins A, C, D, E, F, G and H derived from the *R. equi* strain 103+ plasmid. Proteins were produced in order to test the hypothesis that resistance of susceptibility to *R. equi* pneumonia in foals is associated with distinct IgG subtype-related antibody responses to the seven virulence-related Vap proteins and that in pneumonic foals the profile reflects a Th2-biased response whereas in healthy foals and adults, the profile reflects a Th1-biased response. 6 clinically normal pony foals from a farm with a history of *R. equi* infection in foals representing a clinically normal, *R. equi* exposed foal group, 6 clinically normal adult horses representing an *R. equi* immune group, and 8 foals with clinical *R. equi* pneumonia representing a nonimmune group, were used in this study. Hooper-McGrevy, et al., 2003 concluded that the higher the ratio of IgGa to IgGb subtype ratio and IgGa to IgGT ratio, the better the animals are protected against *R. equi*.

Lopez, et al. 2003 set out to evaluate the immune response of foals to a DNA vaccine expressing a His-tagged recombinant VapA. Using the vapA gene amplified from the virulent *R. equi* strain 33701, Lopez, et al. 2003 designed a recombinant plasmid DNA containing the vapA gene (pVR1055vapA) and His-tagged recombinant VapA protein (rVapA). To characterize the primary immune response elicited by DNA immunization, 5 foals between 8 and 15 days of age (day 1) received 0.5 mg of pVR1055vapA intranasally. At day 14, foals received another 0.5 mg of pVR1055vapA intranasally. At day 30, foals received 0.1 mg of protein intranasally and 0.1 mg of protein containing 0.5 mls of RIBI adjuvant intradermally.

When examined at day 24 (10 days following the DNA boost), none of the foals had developed detectable antibodies against VapA. At day 45 (15 days following the protein boost), 2 of the 5 foals showed strong VapA-specific IgG antibody responses as measured by ELISA compared 20 with the control foals. Based on the observation that 2 foals mounted an immune response within 15 days of receiving a VapA protein boost, Lopez, et al. 2003 concluded that pVR1055vapA priming of naïve foals is suboptimal for the goal of protecting foals against *R. equi* and that a more profound protein boost, such as might occur with a low dose challenge with virulent *R. equi* organisms, may have been more successful at priming the foals. Lopez, et al. 2003 suggested that protecting foals against *R. equi* infection required priming and expanding lymphocytes within the first few weeks of life and proposed using a modified DNA based vapA vaccine whereby cytokine genes such as IL-12 and GM-CSF would be included in the vaccine. The most significant finding from this study was that the only immune response observed was after foals were immunized with the protein boost.

In a study aimed at evaluating serum IgG antibody levels and opsonizing activity in foals from pregnant mares immunized with either VapA or whole killed *R. equi* together with a water-based nanoparticle adjuvant, Cauchard, 2004 identified VapA as a candidate vaccine for immunizing pregnant mares resulting in passive antibody-mediated protection of foals. The whole formaldehyde-killed *R. equi* preparation (WKRE) was prepared from an isolate obtained from an infected foal from an endemically affected breeding farm in Normany, France. VapA was purified from *R. equi* strain 85F, which was obtained from a foal in the same geographic area. 24 mares were immunized with 1 mg of VapA protein at 9, 6 and 3 weeks before delivery, 8 mares were immunized with $10^9$ bacteria at 24, 12 and 4 weeks before delivery. 15 mares served as controls and received adjuvant without purified protein or WKRE at 9, 6 and 3 weeks before delivery.

IgG antibodies were significantly higher in colostrum from the purified VapA immunized mares and WKRE immunized mares compared with the control mares, but no significant difference in titer between the VapA immunized mares and WKRE immunized mares was observed. After foals received colostrum, all foals exhibited *R. equi* antibody levels close to that of their mare. Foals born to WKRE immunized mares maintained the most stable antibody levels compared to foals born to VapA immunized mares and foals born to control mares.

Four of the 13 foals born to control mares developed proven *R. equi* pneumonia where all of the 23 foals born to VapA immunized mares and all of the 7 foals born to WKRE immunized mares remained free of *R. equi* induced pneumonia for the first 6 months of life. *R. equi* was confirmed by bacterial isolation from transtracheal aspirates, blood and feces.

Based on this study, in which environmental exposure was the only means of challenge, Cauchard et al. 2004 concluded that pregnant mare immunization with VapA protein antigen associated with a water-based nanoparticle adjuvant provides a more accessible, passive antibody-mediated protection than administration of hyperimmune plasma. This conclusion is based on the fact that serum opsonic activity in mares was higher in immunoglobulin from mares immunized with VapA than in either the control group or mares immunized with WKRE.

Taouji et al., 2004 tested synthetic VapA peptides (N15Y and V20S) representing B-cell epitope with two groups of adjuvants. Mice were immunized with 100 micrograms antigenic content twice at 2 week intervals. Mice were challenged with $2\times10^6$ *R. equi* ATCC 33701 4 weeks after the first vaccination and were euthanized and sampled 4 days after challenge. Mares ranging in age from 2 to 7 years were immunized subcutaneously with 0.5 mg antigenic content twice at 4 week intervals. Taouji et al. 2004 observed that the nanoparticle adjuvants elicicited the best immune response in comparison to metabolized oil adjuvant and that all adjuvants promoted anti-N15Y IgG2b and in a lesser extent, IgGa and IgGT. Additionally, antibodies to N15Y were detected in sera of immunized mares for 12 months. Taouji, et al. 2004 concluded that the N15Y peptide with the low-oil adjuvant was the most effective immunogen by elicicitng primary and memory immune response in mares, but that the efficiency of the N15Y peptide in combination with T-cell epitope would need to be further evaluated before challenge of foals.

Vanniasinkam et al., 2004 studied the immunogenicity of *R. equi* vaccines in a murine model for the potential use as vaccine candidates to protect against *R. equi* in foals. Four groups of five female BALB/c mice at 6-8 weeks of age were used in this study. Each group of mice was vaccinated separately with pcDNA3-Re1, His-tagged GroEL2, pcDNA3 vector, or $10^5$ live virulent *R. equi* strain ATCC 33701. All animals were vaccinated three times, two weeks apart. Two weeks after the last immunization, all mice were challenged with an intravenous inoculation of $1.5\times10^7$ virulent *R. equi* strain ATCC 33701. Animals were symptom free a few days post-challenge, and bacterial clearance was measured 48-120 hours post-challenge. The protein-based vaccine elicited a mixed Th1/Th2 response, whereas the DNA vaccine elicited a predominantly Th1 biased immune response. When the vaccinated mice were challenged, neither vaccine enhanced bacterial clearance from the spleen or liver. Vanniasinkam et al., 2004 concluded that the co-administration of immunostimulatory molecules, such as IL-18 and IL-12, together with a pathogen-specific antigen-encoding DNA vaccine might be an option for enhancing a Th1 protective response. This approach may be useful for improvement of the Th1 type immunity observed.

Vanniasinkam et al. 2005 performed another study to determine the immune response elicited by *R. equi* VapA protein-based vaccines in a murine model. To test this, four groups of five 6-8 week old female BALE/c mice were vaccinated with pcDNA3-Re2, pcDNA3 vector, live *R. equi*, or His-tagged VapA protein. One group of mice received 5 µg of the murine cytokine IL-12 expression plasmid pORF-mIL12 co-injected with pcDNA3-Re2. All mice were vaccinated three times, two weeks apart. Two weeks after the last immunization, mice were challenged with an intravenous inoculation of $1.5\times10^7$ virulent *R. equi* strain ATCC 33701. Clearance of bacteria was measured 48-120 hours post-challenge. It was found that there was no significant difference in the rates of bacterial clearance from both the liver and spleen of mice with either the vapA-based DNA or protein vaccine compared with the control group. Overall, the results of this study suggest that VapA-based vaccines whether administered as DNA or recombinant protein vaccines do not enhance clearance of *R. equi* in the murine model, unlike the live *R. equi*. The efficacy of the live vaccine suggests that other *R. equi* antigens in addition to VapA may be required in order to induce a protective immune response to *R. equi*. Other strategies, including a heterologous prime/boost vaccination regiment, potent adjuvants, and viral vaccine carriers, could be employed to enhance the efficacy of the DNA vaccine used in this study.

Haghighi and Prescott, 2005 attempted to test the hypothesis that a DNA vaccine encoding vapA could induce a cell-mediated immune response to *R. equi* in mice and that the induction of this immunity confers protection against *R. equi*, and whether IL-12 would enhance this effect. A recombinant plasmid containing the vapA gene derived from the virulent strain ATCC 33701 (pcDNA3.1-vapA) was used in combination with a vector expressing IL-12 (pORF-mIL-12) as an adjuvant for pcDNA3.1-vapA. Mice were immunized with 100 micrograms of pcDNA3.1-vapA or 50 micrograms of pcDNA3.1-vapA and 50 micrograms of pORF-mIL-12. On day 21 after the first immunization, mice were challenged intravenously with 5×10^5 *R. equi* strain ATCC 33701 and were euthanized 4 days later. The DNA vaccine was effective in inducing a cellular immune response, and a significant increase in the VapA specific IgG2a to IgG1 ratio was observed. Using pORF-mIL-12 led to a significant increase in *R. equi* clearance from the liver, but a significant reduction in specific antibody titer. Haghighi and Prescott, 2005 concluded that DNA immunization using vapA and IL-12 has potential as a vaccine approach in foals and suggested that inclusion of other vap genes might also enhance the immune response.

As an extension of the Chirino-Trejo et al. 1987 study, Hooper-McGrevy et al. 2005 tried to determine whether oral immunization of foals with virulent *R. equi* strain ATCC 33701 within the first 2 weeks of life would induce protection by 3 weeks of age. This study also addressed whether or not it is possible to induce an effective immune response to *R. equi* in very young foals, given the difficulty to achieve efficacious vaccination of the neonate in the presence of maternal antibody.

The immunization schedule consisted of administration of 100 mL of phosphate-buffered saline (PBS), containing 1×10^8 CFU/mL of *R. equi* by stomach tube, 2 days after birth and again at 1 and 3 weeks of age. The control group contained 4 foals which were administered PBS only, by the same route. All foals were challenged at 3 weeks of age with 25 mL of *R. equi* containing 2×10^6 CFU/ml by intrabronchial inoculation into each of the major bronchi. After the challenge, the heart rate, respiratory rate and temperature of the foals were monitored twice daily. Blood was collected every other day for fibrinogen concentration, white blood cell count, and serology. Foals were euthanized via IV injection of pentobarbital sodium, 14 days after challenge (day of challenge being designated as day 0).

The non-immunized control foals remained healthy during the infection-immunization period, but developed signs of pneumonia by day 9 post-challenge. In comparison, the infection-immunized foals remained alert and healthy throughout the 2 week post-challenge. Assessment of the lungs postmortem showed that pneumonia occurred only in controls, but there was significant enlargement of lung-associated lymph nodes in foals from both groups. As a result of the pneumonia, the lungs of the control foals showed signs of obvious congestion and edema. The lungs of infection-immunized foals were free of lesions.

Analysis of antibody response was performed using Vap-specific ELISAs. The main difference in total antibody response between the control and immunized foal groups was for VapA and VapC. The anti-VapA and anti-VapC response in immunized foals was significantly greater, from day 0 through day 10 post-challenge and from day 2 through day 10, respectively. The total antibody response to the other Vap proteins did not differ.

Based on these results, Hooper-McGrevy concluded that future work should investigate the possibility of creating mutant strains of *R. equi* to reduce virulence but possess a majority of the immunogenic proteins such as VapA and VapC.

Mealey et al., 2007 attempted to induce a Type1/Th1 response in neonatal foals using a DNA-based *R. equi* vapA vaccine using recombinant equine IL-12 as a molecular adjuvant. Four foals under 8 days of age were immunized intradermally and intranasally with 1 mg of the DNA based vapA vaccine pVR1055vapA and 1 mg of IL-12 plasmid (day 1). On day 15, all foals received a second DNA vaccination. On day 30, all foals received a protein boost with 0.5 mg of purified recombinant VapA protein intradermally and 0.1 mg of purified recombinant VapA protein intranasally. Foals were challenged with *R. equi* ATCC 33701 virulent strain 2 weeks following the purified recombinant VapA protein boost. A challenge dose was 10^4 organisms per animal was used because the objective of this study was to evaluate immune responses with and without IL-12 DNA as an adjuvant and not to induce disease to evaluate protection for 2 weeks post-challenge. Mealey et al., 2007 was unable to detect a significant adjuvant effect in foals. Thus, the DNA based vapA vaccine pVR1055vapA was shown to be poorly immunogenic in foals.

Jacks et al., 2007 performed a study to determine the relative expression of *R. equi* vap genes and the lymphoproliferative responses in the lungs of infected foals. Five 7 to 10 day old foals and five 2 to 12 year old adult horses were used in the study. Transfer of passive immunity was confirmed in foals at 12 to 24 hours of age. Each foal was intrabronchially challenged with approximately 1×10^6 CFU of *R. equi* strain ATCC 33701, and each adult was intrabronchially challenged with approximately 1×10^7 CFU (2×10^4 CFU per kg of body weight). All of the animals were physically examined every day post-challenge for fifteen days, and their heart rate, respiratory rate, and temperature was recorded twice daily. At fifteen days post-challenge, all animals were euthanized, and bronchial lymph nodes (BLN) and cranioventral lung lobe tissue was aseptically collected.

To study the proliferative responses in the BLN and lobe tissue samples, GST-tagged recombinant VapA and VapC-H proteins were developed. Cells were separately incubated with no antigen (blank), 2 μg/mL of concanavalin A (positive control), 10 μg/mL of *Corynebacterium pseudotuberculosis* soluble antigens (negative control), or 50 μg/mL of each of the recombinant proteins. The lymphoproliferative response to VapA and VapC proteins in foals and adult horses was significantly greater than those to all other Vap proteins; however, Jacks et al. 2007 present data that indicates that vapA, vapD, and vapG are the most biologically relevant vap genes, due to their preferential induction during natural host infection.

Oliveira et. al. 2010 attempted to demonstrate the effects of immunization of mice with *Salmonella enterica Typhimurium* expressing the VapA antigen against *R. equi* infection. Five female BALB/c mice, 6 to 8 weeks of age, were intragastrically immunized with 1×10^9 CFU of *S. enterica Typhimurium* χ3987-pYA3137vapA. For the control group, five mice of the same type and age were intragastrically immunized with 1×10^9 CFU of *S. enterica Typhimurium* χ3987-pYA3137 and five mice were inoculated with 200 microliters of PBS only. The same pattern of immunization took place also 14 days post initial immunization.

All groups of mice were infected with a sublethal dose of virulent *R. equi* ATCC 33701, 14 days after the last immunization and euthanized. Based on analysis of samples of feces, spleen cells, and other organs Oliveira et al., 2010 concluded that VapA-immunization triggers mucosal-humoral response and systemic cell-mediated immunity, reflected by 5 fold higher IgA levels found in immunized mice compared to control mice. Additional analysis proved that *R. equi* antigen stimulates the production of Th1 Cytokines by spleen cells from mice vaccinated with *S. enterica Typhimurium* χ3987-pYA3137vapA. Additionally, vaccination with *S. enterica Typhimurium* χ3987-pYA3137vapA provided long term (duration of 5 months tested) protection of mice against *R. equi* infection. Based on the strong immune response of mice, Oliveira et al., 2010 suggested investigating immunization of foals against *R. equi*.

Cauchard et al., 2011 created a *Lactococcus lactis* strain, LL-VapA, that expressed a His-tagged and S-Tagged VapA recombinant protein, and used the live bacterial strain LL-VapA to immunize mice. Mice were challenged with *R. equi* and it was shown that the LL-VapA strain helped induce an immune response in mice. However, the LL-VapA strain was not tested in horses.

Heuzenroeder, et al. 2009 used the VapA protein to design overlapping peptides, which provides an epitope map to be used in discovering potential vaccines for *R. equi*.

Pei et al., 2007 generated an attenuated *R. equi* 103+ strain by disrupting the isocitrate lyase and cholesterol oxidase chromosomal genes (mutant). The goal was to assess the value of this strain for its immunizing ability. 6 ponies were immunized intrabronchially with $5\times10^7$ mutant *R. equi* at 7 days of age. At 21 days of age, foals were challenged with $5\times10^7$ virulent parent *R. equi* 103+. Foals were observed then euthanized 14 days post challenge. 3 foals remained unaffected by the mutant and were successfully immunized against infection with the parent *R. equi* strain. Pei et al. 2007 observed disease in a proportion of immunized foals, suggesting that the approach to producing double unmarked targeted mutations for use in immunization remains as a proof of principle.

A riboflavin auxotrophic live attenuated-vaccine stimulated an immune response but no protection against *R. equi* was observed when the foals were challenged (Lopez et al., 2008). A live attenuated-vaccine that targets the cholesterol catabolic gene cluster, necessary for *R. equi* virulence, was tested in foals and claimed to elicit an immune response against *R. equi* (van der Geize et al., 2011).

SUMMARY OF THE INVENTION

The present invention provides a recombinant protein comprising consecutive amino acids, the sequence of which is substantially identical to a sequence of amino acids present in a *Rhodococcus equi* virulence-associated protein.

The present invention also provides a composition comprising a recombinant protein of the invention and a carrier.

The present invention also provides a composition comprising a first recombinant protein, a second recombinant protein and a carrier, wherein each of the first recombinant protein and the second recombinant protein is different and is a recombinant protein of the invention.

The present invention also provides use of a fusion protein or a composition of the invention in the manufacture of hyperimmune plasma against *Rhodococcus equi*.

The present invention also provides a process of producing a hyperimmune plasma against *Rhodococcus equi* which comprises the steps of:
(a) identifying a donor animal;
(b) administering to the donor animal an amount of a composition of the invention effective to induce a hyperimmune response;
(C) obtaining blood from the donor animal of step (b); and
(d) purifying the hyperimmune plasma.

The present invention also provides a hyperimmune plasma produced by a process of the invention.

The present invention also provides a process for protecting an animal against *Rhodococcus equi* which comprises:
(a) administering to the animal an amount of a composition of the invention effective to induce a protective immune response; and then
(b) administering one or more booster amounts of the same composition.

The present invention also provides a process of protecting a newborn animal against *Rhodococcus equi* which comprises:
(a) administering to a pregnant female bearing the animal an amount of a composition of the invention effective to induce a protective immune response; and then
(b) administering one or more booster amounts of the same composition to the pregnant female.

BRIEF DESCRIPTION OF THE FIGURES

FIG. 1

Figure 2A:
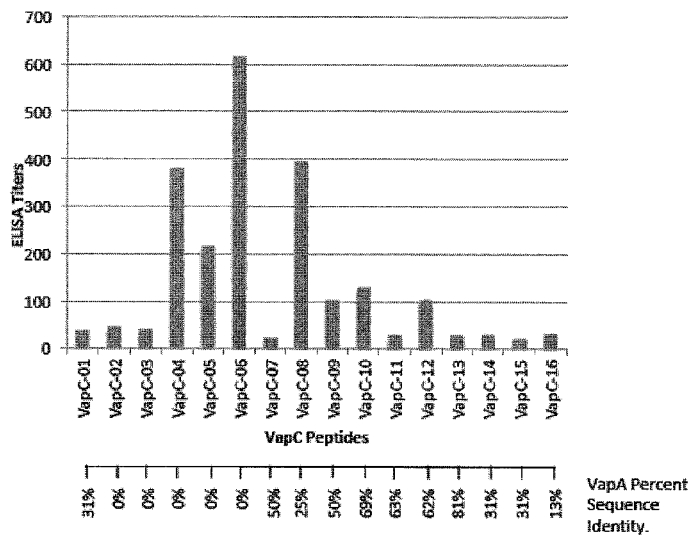

Amino acid alignment of all Vap protein sequences, corresponding to SEQ ID NOs 1-15 (VapA=SEQ ID NO:1; VapB=SEQ ID NO:2; VapC=SEQ ID NO:3; VapD=SEQ ID NO:4; VapE=SEQ ID NO:5; VapF=SEQ ID NO:6; VapG=SEQ ID NO:7; VapH=SEQ ID NO:8; VapI=SEQ ID NO:9; VapJ=SEQ ID NO:10; VapK1=SEQ ID NO:11; VapK2=SEQ ID NO:12; VapL=SEQ ID NO:13; VapM=SEQ ID NO:14; and VapX=SEQ ID NO:15). Multiple sequence alignment of *R. equi* Vap proteins using CLUSTAL W (1.83). Alignment was performed using alignment tools at www.tcoffee.org using T-coffee default parameters. SEQ IDENTITY row shows the level of sequence identity where a dash (-) indicates little to moderate sequence identity and an asterisk (*) represents a high level of sequence identity among all the Vap proteins.

FIG. 2

Comparison of average VapC peptide titers in serum collected from VapC immunized plasma donor horses and commercial plasma from *R. equi* immunized plasma donor horses. Synthesized VapC peptides were tested with an ELISA against donor test bleed samples from VapC vaccinated donors (A) and commercial plasma (B) to measure their titer concentrations. The VapA homology line indicates the percent homology between the VapA and VapC proteins.

DETAILED DESCRIPTION OF THE INVENTION

Terms

As used in this application, except as otherwise expressly provided herein, each of the following terms shall have the meaning set forth below.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

"Amino acid," "amino acid residue" and "residue" are used interchangeably herein to refer to an amino acid that is incorporated into a protein, polypeptide or peptide. The amino acid can be, for example, a naturally occurring amino acid or an analog of a natural amino acid that can function in a manner similar to that of the naturally occurring amino acid.

As used herein, an "amount" or "dose" of an agent measured in milligrams refers to the milligrams of agent present in a drug product, regardless of the form of the drug product.

As used herein, the term "composition", as in pharmaceutical composition, is intended to encompass a product comprising the active ingredient(s) and the inert ingredient(s) that make up the carrier, as well as any product which results, directly or indirectly from combination, complexation, or aggregation of any two or more of the ingredients, or from dissociation of one or more of the ingredients, or from other types of reactions or interactions of one or more of the ingredients.

As used herein, "effective amount" refers to an amount which is capable of treating a subject. Accordingly, the effective amount will vary with the subject being treated, as well as the condition to be treated. A person of ordinary skill in the art can perform routine titration experiments to determine such sufficient amount. The effective amount of a compound will vary depending on the subject and upon the particular route of administration used. Based upon the compound, the amount can be delivered continuously, such as by continuous pump, or at periodic intervals (for example, on one or more separate occasions). Desired time intervals of multiple amounts of a particular compound can be determined without undue experimentation by one skilled in the art.

The terms "nucleic acid", "polynucleotide" and "nucleic acid sequence" are used interchangeably herein, and each refers to a polymer of deoxyribonucleotides and/or ribonucleotides. The deoxyribonucleotides and ribonucleotides can be naturally occurring or synthetic analogues thereof. "Nucleic acid" shall mean any nucleic acid, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA). Nucleic acids include, without limitation, anti-sense molecules and catalytic nucleic acid molecules such as ribozymes and DNAzymes. Nucleic acids also include nucleic acids coding for peptide analogs, fragments or derivatives which differ from the naturally-occurring forms in terms of the identity of one or more amino acid residues (deletion analogs containing less than all of the specified residues; substitution analogs wherein one or more residues are replaced by one or more residues; and addition analogs, wherein one or more resides are added to a terminal or medial portion of the peptide) which share some or all of the properties of the naturally-occurring forms.

The terms "polypeptide," "peptide" and "protein" are used interchangeably herein, and each means a polymer of amino acid residues. The amino acid residues can be naturally occurring or chemical analogues thereof. Polypeptides, peptides and proteins can also include modifications such as glycosylation, lipid attachment, sulfation, hydroxylation, and ADP-ribosylation.

As used herein, "pharmaceutically acceptable carrier" means that the carrier is compatible with the other ingredients of the formulation and is not deleterious to the recipient thereof, and encompasses any of the standard pharmaceutically accepted carriers. Such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases, and the like.

As used herein, "substantially identical" means varying by one or more, preferably not more than five amino acids, more preferably not more than three amino acids, while having the same activity as a *Rhodococcus equi* virulence-associated protein. For example, an additional methionine or N-formyl methionine at the N-terminus.

As used herein, a "carbomer-based adjuvant" includes adjuvants containing Carbopol 934P such as Carbigen® (MVP Technologies).

Embodiments of the Invention

The present invention provides a recombinant protein comprising consecutive amino acids, the sequence of which is substantially identical to a sequence of amino acids present in a *Rhodococcus equi* virulence-associated protein.

In one or more embodiments the virulence-associated protein is VapA.

In one or more embodiments the virulence-associated protein is VapC.

In one or more embodiments the sequence of the recombinant protein is substantially identical to the sequence of amino acids 29-189 of VapA.

In one or more embodiments the sequence of the recombinant protein is the sequence set forth in SEQ ID NO: 16.

```
SEQ ID No. 16:
NATVLDSGSSSAILNSGAGSGIVGSGSYDSSTTSLNLQKDEPNGRASDT

AGQEQQYDVHGDVISAVVYQRFHVFGPEGKVFDGDAGGLTLPGAGAFWG

TLFTNDLQRLYKDTVSFQYNAVGPYLNINFFDSSGSFLGHIQSGGVSTV

VGVGGGSGSWHNA
```

In one or more embodiments the sequence of the recombinant protein is substantially identical to the sequence of amino acids 29-174 of VapC.

In one or more embodiments the sequence of the recombinant protein is the sequence set forth in SEQ ID NO: 17.

```
SEQ ID No. 17:
NVVAPSAWGGAQSAADKEGEGVTLGGVGVLRPHNKDADEQYTVHGVVVS

ALFYNHLRISVDGGMTFDGDGGGLSTPGGGALWGTLTTSDLQQLYDETA

SFECNAVGPYLNINFYDSYGRILASVQAGGVSTMIGIGGGNGRWHLV
```

In one or more embodiments the *Rhodococcus equi* virulence-associated protein is present in the *Rhodococcus equi* strain designated ATCCC 33701.

In one or more embodiments the recombinant protein further comprises consecutive amino acids which comprise a detectable tag.

In one or more embodiments the tag is a 6-His tag or a poly-6-His tag.

In one or more embodiments the tag is a glutathione S-transferase tag.

In one or more embodiments the tag is linked directly or via a linker sequence to the N-terminus of the amino acids, the sequence of which is substantially identical to the sequence of the *Rhodococcus equi* virulence-associated protein.

In one or more embodiments the tag is linked directly or via a linker sequence to the C-terminus of the amino acids, the sequence of which is substantially identical to the sequence of the *Rhodococcus equi* virulence-associated protein.

In one or more embodiments the tag is linked through a linker sequence.

In one or more embodiments the sequence of the recombinant protein is set forth in SEQ ID NO: 18.

SEQ ID No. 18: (HIS tagged VapA)
HHHHHH<polylinker>NATVLDSGSSSAILNSGAGSGIVGSGSYDSS

TTSLNLQKDEPNGRASDTAGQEQQYDVHGDVISAVVYQRFHVFGPEGKV

FDGDAGGLTLPGAGAFWGTLFTNDLQRLYKDTVSFQYNAVGPYLNINFF

DSSGSFLGHIQSGGVSTVVGVGGSGSWHNA

In one or more embodiments the sequence of the recombinant protein is set forth in SEQ ID NO: 19.

SEQ ID No. 19: (GST tagged VapA)
MSPILGYWKIKGLVQPTRLLLEYLEEKYEEHLYERDEGDKWRNKKFELG

LEFPNLPYYIDGDVKLTQSMAIIRYIADKHNMLGGCPKERAEISMLEGA

VLDIRYGVSRIAYSKDFETLKVDFLSKLPEMLKMFEDRLCHKTYLNGDH

VTHPDFMLYDALDVVLYMDPMCLDAFPKLVCFKKRIEAIPQIDKYLKSS

KYTAWPLQGWQATFGGGDHPPK<polylinker>NATVLDSGSSSAILN

SGAGSGIVGSGSYDSSTTSLNLQKDEPNGRASDTAGQEQQYDVHGDVIS

AVVYQRFHVFGPEGKVFDGDAGGLTLPGAGAFWGTLFTNDLQRLYKDTV

SFQYNAVGPYLNINFFDSSGSFLGHIQSGGVSTVVGVGGSGSWHNA

In one or more embodiments the sequence of the recombinant protein is set forth in SEQ ID NO: 20.

SEQ ID No. 20: (HIS tagged VapC)
HHHHHH<polylinker>NVVAPSAWGGAQSAADKEGEGVTLGGVGVLR

PHNKDADEQYTVHGVVVSALFYNHLRISVDGGMTFDGDGGGLSTPGGGA

LWGTLTTSDLQQLYDETASFECNAVGPYLNINFYDSYGRILASVQAGGV

STMIGIGGGNGRWHLV

In one or more embodiments the sequence of the recombinant protein is set forth in SEQ ID NO: 21.

SEQ ID No. 21: (GST tagged VapC)
MSPILGYWKIKGIVQPTRLLLEYLEEKYEEHLYERDEGDKWRNKKFELG

LEFPNLPYYIDGDVKLTQSMAIIRYIADKHNMLGGCPKERAEISMLEGA

VLDIRYGVSRIAYSKDFETLKVDFLSKLPEMLKMFEDRLCHKTYLNGDH

VTHPDFMLYDALDVVLYMDPMCLDAFPKLVCFKKRIEAIPQIDKYLKSS

KYIAWPLQGWQATFGGGDHPPK<polylinker>NVVAPSAWGGAQSAA

-continued
DKEGEGVTLGGVGVLRFHNKDADEQYTVHGVVVSALFYNHLRISVDGGM

TFDGDGGGLSTPGGGALWGTLTTSDLQQLYDETASFECNAVGPYLNINF

YDSYGRILASVQAGGVSTMIGIGGGNGRWHLV

The present invention also provides a composition comprising a recombinant protein of the invention and a carrier.

In one or more embodiments the recombinant protein is present in an amount about 0.25 mg/ml to about 2.5 mg/ml.

In one or more embodiments the recombinant protein is present in an amount about 0.5 mg/ml to about 1.5 mg/ml.

In one or more embodiments the recombinant protein is present in an amount of about 1 mg/ml.

The present invention also provides a composition comprising a first recombinant protein, a second recombinant protein and a carrier, wherein each of the first recombinant protein and the second recombinant protein is different and is a recombinant protein of the invention.

In one or more embodiments each of the first recombinant protein and the second recombinant protein is present in an amount which may be the same or different and is between about 0.25 mg/ml and about 2.5 mg/ml.

In one or more embodiments each of the first recombinant protein and the second recombinant protein is present in an amount between about 0.5 mg/ml and about 1.5 mg/ml.

In one or more embodiments each of the first recombinant protein and the second recombinant protein is present in an amount of about 1 mg/ml.

In one or more embodiments the composition further comprises an adjuvant.

In one or more embodiments the adjuvant is present in an amount of 5-15% by volume.

In one or more embodiments the adjuvant is present in an amount of about 10% by volume.

In one or more embodiments the adjuvant is a carbomer-based adjuvant.

In one or more embodiments the composition has a pH between about 6.5 and about 7.5.

In one or more embodiments the pH is between about 6.7 and about 7.2.

The present invention also provides use of a fusion protein or a composition of the invention in the manufacture of hyperimmune plasma against *Rhodococcus equi*.

The present invention also provides a process of producing a hyperimmune plasma against *Rhodococcus equi* which comprises the steps of:
(a) identifying a donor animal;
(b) administering to the donor animal an amount of a composition of the invention effective to induce a hyperimmune response;
(C) obtaining blood from the donor animal of step (b); and
(d) purifying the hyperimmune plasma.

In one or more embodiments the donor animal is a mammal.

In one or more embodiments the donor animal is a horse.
In one or more embodiments the donor animal is a rabbit.
In one or more embodiments the donor animal is a pig.
In one or more embodiments step (a) comprises screening potential donor animals for a desired blood type.

In one or more embodiments the donor animal is a horse and wherein the horse is identified as a donor horse if the blood typing screen yields a positive result for both blood factors Aa and Ca.

In one or more embodiments step (a) further comprises testing the immunological status of the animal.

In one or more embodiments the animal is tested for antibodies against the following: Equine Viral Arteritis, Brucellosis, Equine infectious Anemia, Equine Piroplasmosis (*Babesia cabilli* and *Theileria equi*), Equine Rhinopnuemonitis (EHV1), Glanders, and Dourine.

In one or more embodiments an animal is identified as a donor animal by the following criteria: <1:4 as tested with Serum Virus Neutralization for Equine Viral Arteritis, negative for Brucellosis, negative for Equine Infectious Anemia, negative for Equine Piroplasmosis, <1: 1024 as tested with Serum Virus Neutralization for Equine Rhinopnuemonitis (EHV1), negative for Glanders, and negative for Dourine.

In one or more embodiments after step (b) but before step (c) a booster amount of the composition is administered.

In one or more embodiments the booster amount is administered from about 2 weeks to about 4 weeks after the administration in step (b).

In one or more embodiments the booster amount is administered about 3 weeks after the administration in step (b).

In one or more embodiments after step (b) additional booster amounts are administered.

In one or more embodiments a second booster amount is administered from about 8 weeks to about 16 weeks after step (b) or after the previous booster amount.

In one or more embodiments a second booster amount is administered about 12 weeks after step (b) or after the previous booster amount.

In one or more embodiments amount is administered in a volume from about 0.5 ml to about 2 ml.

In one or more embodiments the volume is about 1 ml.

In one or more embodiments the amount or the booster amount(s) or both are administered intramuscularly, intraperitoneally, intravenously, or intradermally.

In one or more embodiments the amount or the booster amount(s) or both are administered via intramuscular injection.

The present invention also provides a hyperimmune plasma produced by a process of the invention.

The present invention also provides a process for protecting an animal against *Rhodococcus equi* which comprises:
  (a) administering to the animal an amount of a composition of the invention effective to induce a protective immune response; and then
  (b) administering one or more booster amounts of the same composition.

In one or more embodiments the animal is a mammal.
In one or more embodiments the animal is a horse.
In one or more embodiments the animal is a rabbit.
In one or more embodiments the animal is a pig.

In one or more embodiments step (a) is performed between about 1 week and about 8 weeks after birth of the animal.

In one or more embodiments step (a) is performed between about 2 weeks and about 6 weeks after birth of the animal.

In one or more embodiments a booster amount is administered between about 1 week to about 6 weeks after step (a) or after administration of a previous booster amount.

In one or more embodiments a booster amount is administered between about 2 week to about 4 weeks after step (a) or after administration of a previous booster amount.

In one or more embodiments the number of administrations of booster amounts is 1 to 6, inclusive.

In one or more embodiments an initial booster amount is administered about 2 weeks after step (a) and additional booster amounts are administered about 4 weeks after administration of each previous booster amount.

In one or more embodiments the number of administrations of booster amounts is 3.

In one or more embodiments the amount or the booster amount(s) or both is administered in a volume from about 0.1 ml to about 0.5 ml.

In one or more embodiments the volume is about 0.25 ml.

In one or more embodiments each amount is administered intramuscularly, intraperitoneally, intravenously or intradermally.

In one or more embodiments each amount is administered intramuscularly.

In one or more embodiments the process further comprises administering hyperimmune plasma to the animal, prior to step (a).

In one or more embodiments the hyperimmune plasma is hyperimmune plasma according to the invention.

In one or more embodiments the hyperimmune plasma is administered in a volume from about 500 ml to about 1500 ml.

In one or more embodiments the volume of hyperimmune plasma is about 1000 ml.

In one or more embodiments the hyperimmune plasma is administered orally or intravenously.

The present invention also provides a process of protecting a newborn animal against *Rhodococcus equi* which comprises:
  (a) administering to a pregnant female bearing the animal an amount of a composition of the invention effective to induce a protective immune response; and then
  (b) administering one or more booster amounts of the same composition to the pregnant female.

In one or more embodiments the animal is a horse and wherein the amount is administered during about 6 months to about 10 months after the female animal is pregnant.

In one or more embodiments the amount is administered at about 8 months after the female animal is pregnant.

In one or more embodiments a booster amount is administered from about 1 week to about 4 weeks after step (a).

In one or more embodiments the booster amount is administered at about 2 weeks after step (a).

In one or more embodiments a booster amount is administered about 1 month prior to the predicted foaling date.

All combinations of the various elements described herein are within the scope of the invention.

This invention is illustrated in the Experimental Details section which follows. This section is set forth to aid in an understanding of the invention but is not intended to, and should not be construed to; limit in any way the invention as set forth in the claims which follow thereafter.

Experimental Details

Recombinant VapA/VapC Vaccine(s)

We developed an *R. equi* protein subunit vaccine candidate that induces production of VapA and/or VapC antibodies in foals for protection against *R. equi*. The vaccine was generated by cloning a fragment of vapA or vapC into a His-tagged pRSET-C plasmid and transformed into BL21 (DE3) pLysS cells to produce the protein subunit. We used the vaccine to vaccinate pregnant mares to protect the foal, and donors to generate hyper immune plasma. The foals were administered HIP plasma from the donors and vaccinated with the recombinant VapA, or VapC, or VapAVapC vaccines.

Methods
Development of *R. equi* VapC Vaccine Candidate
*R. equi* Strain and Plasmids The strain 33701 *R. equi* from ATCC was used to clone vapA and vapC. The freeze-dried *R. equi* cells were resuspended in 100 μl Tryptic Soy Broth (BD) and used as a template for PCR amplification of vapA or vapC. The vapA or vapC fragment was cloned into the GST-tagged pGEX vector (GE Healthcare). The GST-tagged vapA or vapC plasmid was used for sequence verification and for expression of recombinant VapA or VapC protein, respectively. Following cloning into the GST-tagged pGEX vector, the vapA or vapC fragment was subcloned into the His-tagged vector pRSET-C (Invitrogen) for expression of recombinant His-tagged VapA or VapC protein and subsequent purification of the VapA or VapC protein. The His-tagged VapA or VapC allows the protein to bind tightly to the Ni-NTA (nickel nitriloacetic acid) agarose during the VapA or VapC protein purification process.

*R. equi* Whole Cell PCR

The vapA [GenBank: AF116907.2] fragment was amplified using the forward primer: 5'-GCCGGATCCACTAATGCGACCGTTCTT-3' [SEQ ID No. 22] and the reverse primer: 5'-CATGAATTCCTAGGCGTTGTGCCA-3' [SEQ ID No. 23] based upon the published sequence of vap A. The vapC [GenBank: AF118813.1] fragment was amplified using the forward primer: 5'-GCCGGATCCGCCAATGTAGTCGCTCCGTC-3' [SEQ ID No. 24] and the reverse primer: 5'-CATGAATTCGCGAGCGTTTACCTTCCGAC-3' [SEQ ID No. 25] based upon the published sequence of vapC. The PCR amplification for vapA or vapC was performed using 5 μl of resuspended *R. equi* cells as a template, an annealing temperature of 72° C., and the published 2-step PCR conditions for the Phusion (Finnzymes) DNA polymerase.

Cloning and Sequencing of vapA and vapC Fragments

The vapA PCR fragment was ligated into the BamHI and EcoRI digested GST-tagged pGEX vector and transformed into the *E. coli* DH5 a competent cells. The plasmid DNA was isolated from *E. coli* DH5 a cells and the gene of interest was sequenced by the BigDye Terminator kit (Applied Biosystems) with the primer 5'-GGGCTGGCAAGCCACGTTTGGT-3'[SEQ ID No. 26], purified with Clean Seq Beads (Applied Biosystems), and analyzed using the 3730x1 DNA analyzer (Applied Biosystems) to verify that the fragment had the correct vapA sequence. The procedure was repeated to clone and sequence the vapC fragment.

Subcloning and Construction of the his-Tagged VapA Protein and his-Tagged VapC Protein The sequence verified pGEX/vapA construct was used to generate an identical vapA fragment to be ligated into the pRSET-C vector. The vapA fragment was amplified using the forward primer: 5'-CGATGGATCCCTAATGCGACCGTTCTTGATTC-3' [SEQ ID No. 27] and the reverse primer: 5'-CATGAATTCCTAGGCGTTGTGCCA-3' [SEQ ID No. 23]. The PCR amplification was performed using 1 μl purified plasmid as a template, an annealing temperature of 72° C. and the published 2-step PCR conditions for the Phusion (Finnzymes) DNA polymerase. The new vapA fragment was ligated into the His-tagged pRSET-C vector and transformed into *E. coli* BL21 (DE3) pLysS cells to express a His-tagged VapA protein. The same procedure was followed to subclone and construct the His-tagged vapC protein. The vapC fragment was amplified using the forward primer: 5'-CGATGGATCCCCAATGTAGTCGCTCCGTCG-3' [SEQ ID No. 28] and the reverse primer: 5'-CATGAATTCGCGAGCGTTTACCTTCCGAC-3' [SEQ ID No. 25].

His-Tagged or GST-Tagged VapA Protein and his-Tagged or GST-Tagged VapC Protein Expression and Western Blotting For production of His-tagged VapA and VapC proteins, a single colony of the transformed *E. coli* BL21 (DE3) pLysS cells expressing either His-tagged VapA protein or His-tagged VapC protein was grown overnight shaking in 5 ml of Terrific Broth (EMD or equivalent) plus antibiotic (Ampicillin at 100 μg/ml) at 37° C. For production of GST-tagged VapA and VapC proteins, a single colony of the transformed *E. coli* DH5 a competent cells expressing either GST-tagged VapA protein or GST-tagged VapC protein was grown overnight shaking in 5 ml of Terrific Broth (EMD or equivalent) plus antibiotic (Ampicillin at 100 μg/ml) at 37° C.

One (1) ml of the overnight culture was transferred into 5 ml of fresh TB plus antibiotic (Ampicillin at 100 μg/mL) and incubated at 37° C. with shaking for 30 min. A 1 ml sample was saved as the non-IPTG (isopropyl 5-D-thiogalactoside) treated sample, and the remaining 5 ml culture was induced with 5 μl of 1 M IPTG. The culture was incubated with shaking for 2 hrs at 37° C. A 1 ml sample of the IPTG treated culture was saved, and both the IPTG treated and non-treated 1 ml samples were spun in a microcentrifuge at room temperature (RT) for 3 min at 10K rpm. Each pellet was resuspended in 100 μl of electrophoresis buffer, boiled for 3 min. and separated in a 15% SDS-PAGE gel.

His-Tagged or GST-Tagged VapA Protein and his-Tagged or GST-Tagged VapC Protein Growth and Purification For production of the His-tagged VapA or VapC protein, two 100 ml starter flasks of TB were inoculated with the pRSET-C construct transformed *E. coli* BL21 (DE3) pLysS cells and incubated at 37° C. overnight. For production of the GST-tagged VapA or VapC protein, two 100 ml starter flasks of TB were inoculated with the pGEX transformed *E. coli* DH5 a competent cells and incubated at 37° C. overnight.

The starter flask was added to 600 ml of TB in a 1 L Erlenmeyer flask and incubated at 30° C. with shaking until the $OD_{600}$ reached 0.9-1.0. The two 700 ml of cells were induced for 4 hrs with 1 mM IPTG and then spun for 10 min at 5,000 rpm in an F6S-6X1000y rotor. The pellets were scraped and transferred into a 50 ml conical at RT where it was resuspended and lysed in 30 ml of PBS/1% Triton X-100/20 mM imidazole/1 mM TCEP and sonicated for 2 min at 20%. The lysed pellets were spun for 15 min at 15,000 rpm in a SS34 rotor, and the supernatant was mixed with 2 ml of Ni-NTA His beads (Qiagen) for every 50 ml conical. The beads and supernatant were mutated for 1 hr at 4° C., and transferred to a chromatography column (Santa Cruz) where the beads were washed with 1×PBS (Santa Cruz) until the $OD_{280}$ reached <0.02. The protein was eluted with 500 mM imidazol, and fractions were pooled until $OD_2$go was equal to 0.3, or higher if possible. Approximately 15-19 ml of protein was gel filtered into Sephadex G25 media (GE Healthcare) on a XK 26/20 column (GE Healthcare) equilibrated with PBS. The protein was concentrated to either 1.15-1.2 mg/ml for a single (VapA or VapC) subunit preparation or greater than 2.3 mg/ml for a dual (VapAVapC) subunit preparation. The protein was sterile filtered using a Luer-Lock syringe (BD) with a 0.2 micron filter. The protein concentration was verified with a BCA assay (Santa Cruz). The protein sample was diluted in electrophoresis buffer (1:1 dilution) and 5 μl were run on a 15% SDS PAGE gel. The procedure was followed for the growth and purification of either His-tagged VapA protein or His-tagged VapC protein.

GST-Tagged VapD, VapE and VapG Protein Growth and Purification

The aforementioned procedure used to grow and purify GST-tagged VapA and VapC proteins was followed for the growth and purification of GST-tagged VapD, SEQ ID No. 29, VapE, SEQ ID No. 30 and VapG, SEQ ID No. 31 proteins.

```
SEQ ID No. 29: (GST tagged VapD)
MSPILGYWKIKGLVQPTRLLLEYLEEKYEEHLYERDEGDKWRNKKFELGLEFPNLPYYIDGDVKLTQS

MAIIRYIADKHNMLGGCPKERAEISMLEGAVLDIRYGVSRIAYSKDFETLKVDFLSKLPEMLKMFEDR

LCHKTYLNGDHVTHPDFMLYDALDVVLYMDPMCLDAFPKLVCFKKRIEAIPQIDKYLKSSKYIAWPLQ

GWQATFGGGDHPPK<polylinker>MVRARAFGRLFTFLLAVAVIATVSMGGANAQELAGTKTSDAA

LLSGNKAAIPEDKEYDVSGRVVSALVYQYFIVTVDDAEDKKGKTFQGDAGGVTIFGVDFFWGTLHTPD

LEKLYSDTVSFQYNAAATFLNINFFDSKGERLGYVLAGAAGTVSGIGGGTGGWE

SEQ ID No. 30: (GST tagged VapE)
MSPILGYWKIKGLVQPTRLLLEYLEEKYEEHLYERDEGDKWRNKKFELGLEFPNLPYYIDGDVKLTQS

MAIIRYIADKHNMLGGCPKERAEISMLEGAVLDIRYGVSRIAYSKDFETLKVDFLSKLPEMLKMFEDR

LCHKTYLNGDHVTHPDFMLYDALDVVLYMDPMCLDAFPKLVCFKKRIEAIPQIDKYLKSSKYIAWPLQ

GWQATFGGGDHPPK<polylinker>MTTVHKKASKAIAFTVALRLPFAGTAVALVLIALTIVAAPTG

IAGAREIGAQAWPASQLESGLAVSGNPVGVHDVRMAVHDDSTHTREFKEDDSEKQYPVHGFASSFIFY

QTVSIIDDDGRGGPGKTFEGEAGGITTPGAAGYAGVLFTSDLERLYRETVSFEYNAVGPYLNINLFA

GDGGLLGHVQSGAISSLVGIGGGTGAWR

SEQ ID No. 31: (GST tagged VapG)
MSRILGYWKIKGLVQPTRLLLEYLEEKYEEHLYERDEGDKWRNKKFELGLEFPNLPYYIDGDVKLTQS

MAIIRYIADKHNMLGGCPKERAEISMLEGAVLDIRYGVSRIAYSKDFETLKVDFLSKLPEMLKMFEDR

LCHKTYLNGDHVTHPDFMLYDALDVVLYMDPMCLDAFPKLVCFKKRIEAIPQIDKYLKSSKYIAWPLQ

GWQATFGGGDHPPK<polylinker>MSVRTLLAATLVAGISVLAPAGIANAETSMVSTTAASSVEHA

ANTYDFAEAKSGSSIPAKVAAEQANSYSVHGLVTSLAVYQHFSLTVEGGGKTFTGDSGGISIPGVAVL

EGTLFTEDLQHLYSDTVSFEYNAVGPYLNINFFDSHGTLLGHVQSGSIGTVSGIGGGTGGWQ
```

Vaccine Preparation Using his-Tagged Recombinant VapA and/or VapC Proteins

His-tagged recombinant VapA and His-tagged recombinant VapC were used for preparation of the vaccine. The recombinant VapA only vaccine was prepared by mixing sterile filtered 1.2 mg/ml±0.1 mg/ml recombinant VapA protein in PBS with 10% Carbigen (MVP) adjuvant of the total volume, and vortexed until it was well mixed so that the final concentration of VapA protein was 1.0±0.1 mg/ml. The VapA VapC combination vaccine was prepared by combining 2.3 mg/ml±0.1 mg/ml of sterile filtered recombinant VapA protein, 2.3 mg/ml±0.1 mg/ml of sterile filtered recombinant VapC protein, and 10% Carbigen adjuvant of the total volume so that the final concentration of VapA protein was 1.0±0.1 mg/ml. The mixture was vortexed until mixed. The recombinant VapC only vaccine was prepared by mixing sterile filtered 1.2 mg/ml±0.1 mg/ml of VapC protein in PBS with 10% Carbigen adjuvant of the total volume, and vortexed until it was well mixed so that the final concentration of VapC protein was 1.0±0.1 mg/ml. Each vaccine suspension was incubated at 4° C. for 0-8 hrs, and pH adjusted to 6.7-7.2 with 10 M NaOH. The pH was measured again 0-16 hrs later before placing the suspension in the needles. To prepare the adult vaccine 1 ml of the suspension was taken up into a 3 ml syringe. To prepare the foal vaccine 250 μl of the suspension was taken up into a 1 ml syringe. The syringes were packaged and stored at 4° C. for immediate use.

Screening Horses as Potential Blood Donors for Donating Plasma

Prospective horses underwent a series of exams to determine their qualification as plasma donors. Blood samples were obtained from the jugular vein on either side of the neck in a furrow or groove coursing longitudinally the length of the ventrolateral portion of the neck. The first series of tests to determine if the horse was suitable for the program was a Blood Typing/Antibody screen. A horse was considered suitable if the blood typing and antibody screen yielded positive results for the blood factors Aa and Ca. The horse was considered an unsuitable donor if the blood typing and antibody screen yielded negative results for the blood factors Aa and Ca. A negative result suggested that the animal had or had developed naturally occurring antibodies to these antigens, which was counterproductive for using this individual as a blood donor.

If the horse passed the first initial tests, the second series of tests verified the immunological status of specific diseases. The tests and test types included: Equine Viral Arteritis tested with Serum Virus Neutralization, Brucellosis tested with Card Test, Equine infectious Anemia tested with Agar Gel Immunodiffusion, Equine Piroplasmosis (*Babesia cabilli* and *Theileria equi*) tested with Competitive Enzyme Linked Immunosorbent Assay, Equine Rhinopnuemonitis (EHV1) tested with SVN, Glanders tested with Complement Fixation, and Dourine tested with Complement Fixation. A horse was considered suitable for the program if the immunological tests had the following results: <1:4 for Equine Viral Arteritis, negative for Brucellosis, negative for Equine Infectious Anemia, negative for Equine Piroplasmosis, <1:1024 for Equine Rhinopnuemonitis (EHV1), negative for Glanders, and negative for Dourine. If the horse was found unsuitable based on the immunological results, the horse was disqualified from the program. A suitable donor was considered one that passed both the blood typing/antibody screen and the immunological testing. The horse was then referred to as an Equine Plasma Donor (EPD). An unsuitable donor was a horse that failed either the blood typing/antibody screen or one that passed the blood typing/antibody screen, but failed one or more tests that make up the immunological testing. Horses accepted as blood donors underwent additional immunological testing for specific diseases before the 12-month anniversary of the initial screening date to ensure the immunological status of each donor to be within acceptable limits.

Receipt of Equine Plasma Donors (EPDs) into the Donor Herd, Initializing and Boosting of the EPDs Each non-vaccinated EPD was tested for immunological titers prior initializing (first vaccine given to an EPD not previously vaccinated for *R. equi*) with the VapA, VapAVapC, or VapC vaccine. A minimum of 3 ml of blood was collected from the left jugular vein into a vial without anticoagulant for the purpose of immunological screening. The 2011 non-vaccinated EPD was initialized with the VapC vaccine and the 2012 non-vaccinated EPD was initialized with the VapA vaccine. Both were vaccinated via an intramuscular injection of 1 ml in the left neck region. The 2012 EPD vaccinated with VapC in prior year (2011), was initialized with 1 ml dose of VapAVapC, via an intramuscular injection of 1 ml in the left neck region. The date and time of initialization was recorded per EPD. Following initialization, the rectal temperatures of the EPDs were monitored twice daily for a period of three days. A normal rectal temperature was in the range of 99-101.0° F. All the temperature readings were recorded per EPD with the date and time of each examination. Each EPD was tested for immunological titers by taking a blood sample as described previously prior to administering the first boost. The first boost was given to each EPD three weeks from the date of initialization via an intramuscular injection of 1 ml into the right neck region. The date and time of the boost was recorded per EPD. Following the boost, the rectal temperature of the EPD was monitored twice daily for three days, and recorded as before. Each EPD was further tested for immunological titers by taking a blood sample prior to subsequent boosts and received additional boosts of VapC vaccine at 12-week intervals in 2011 using the same concentration (1 mg/ml) via an intramuscular injection rotating injection sites with each procedure. In 2012, each EPD received additional boosts of VapA and VapA VapC vaccine at 8-week intervals. The date and time of each boost was recorded per EPD. The rectal temperature of each EPD was monitored twice daily for a period of three days and recorded following each subsequent boost.

Preparation of Fresh Whole Blood Collection Bags

In a cell culture flow hood a sterile 50 ml top dispenser bottle was placed onto a bottle of citrate-phosphate-dextrose solution with adenine (CPDA) anticoagulant, and attached to a 1 L blood collection bag. A total of 90 ml of CPDA was transferred to the bag and the excess air was removed with a 30 ml syringe. The collection bag was plugged with a female luer plug and stored at 4° C. for no more than 7 days.

Administration of *Rhodococcus equi* Vaccine to EPDs

In 2011 five donor horses were vaccinated with VapC vaccine to generate *R. equi* HIP (REHIP) plasma. The 2011 donor horses were boosted with VapC vaccine 3 weeks after the first initial vaccine, and boosted at approximately 12-week intervals thereafter. In 2012 we vaccinated 11 donors with VapAVapC vaccine, of which 10 donors were used for REHIP plasma. Three different donor horses were vaccinated with VapA vaccinate, of which 2 were used for VapA REHIP plasma. The VapA donors were not previously vaccinated with VapC, however the VapAVapC donors were previously vaccinated with VapC in 2011. The 2012 donor horses were boosted with the corresponding vaccine 3 weeks after initial boost, and again 4 weeks later and at 8-week intervals thereafter. Vaccinated donor horses that had a VapA or VapC titer of less than 1/800 were not included to generate plasma. The temperature of each donor was monitored twice a day in the morning and afternoon for 3 days after vaccination.

Identification of Suitable EPDs and Collection of Fresh Whole Blood from EPDs

Fresh whole blood from EPDs was harvested every 28 days but no later than every 30 days. No EPD was bled within 2 weeks of a boost with the VapA, VapC, or VapAVapC vaccine or re-vaccination with routine commercially available products for health purposes. Any donor horses treated with painkillers for regular ailments were taken off the painkillers five days prior to harvesting whole blood. The day before a scheduled collection each EPD was screened by observing the individual for signs of clinical illness and by taking a blood sample. A minimum of 3 ml of blood was collected and assayed to determine the packed cell volume (PCV) and total plasma protein (TPP). If the EPD showed any signs of clinical illness, or if the PCV was less than 35%, or if the TPP was less than 6 g/dl, then the EPD was excused as a donor for the scheduled day of collection and subsequently evaluated for reasons that qualified its exclusion from the procedure.

Nine-1 L blood collection bags were allotted per EPD allowing for the harvest of roughly 8 L of whole blood. Each bag was prepared by ensuring the white cap attached to the end of the tubing was removed and kept for future use and a clip or hemostat was placed to clamp the tubing as needed during the blood collection procedure. A vacuum chamber was used to aid in the blood harvesting procedure and was connected to a vacuum pump. The chamber was placed on a 5000-gram scale. With a blood collection bag introduced into the vacuum chamber in preparation for the harvest, the chamber and bag were weighed, with a zeroed scale for purposes of determining the weight of the whole blood being harvested.

Each EPD was placed in a stock or stanchion for purposes of restraint during the procedure. An area over the left jugular vein was clipped and prepped by scrubbing the area with Betadine scrub and rinsing with 70% alcohol. A small bleb of 2% lidocaine was placed subcutaneously using a 21 gauge, 1inch needle and 3 ml syringe. Using a #15 size surgical blade, a small skin incision was made in the area of the bleb. A 10 gauge, 3-inch intravenous catheter was introduced through the skin incision and placed in the left jugular vein. A 72" blood collection set was secured to the hub of the catheter. While occluding the jugular vein just below the catheter placement, a flow of blood was established by means of gravity to fill the tubing. Once the tubing was charged with fresh whole blood, it was subsequently clamped using a clip or hemostat. The collection tubing was then connected to the tubing of the blood collection bag. The clamps were removed from the collection tubing and the tubing of the bag to allow for the flow of blood into the bag. The scale was monitored to allow for a collection of between 720 and 730 grams of fresh whole blood; the flow was stopped by means of replacing clamps onto the tubing of the collection and the bag. The tubing of the bag was re-capped with the white cap and removed from the vacuum chamber. The bag was placed into a refrigerator (4° C.) or ice chest filled with frozen ice packs. The blood harvesting procedure was repeated until 9-1 L blood collection bags were filled with fresh whole blood. Once the procedure was completed, the intravenous catheter was removed from the left jugular vein of the EPD. A liberal amount of povidone-iodine ointment was placed at the venipuncture site and the site was monitored for signs of hematoma formation or continual bleeding. The EPD was then removed from the stock or stanchion and released into a small paddock area. Each EPD was monitored for a period no less than 2 hours and maintained in this area for no less than 18 hours after completion of the procedure. The blood collection bags were transported to the laboratory for further processing.

Processing Fresh Whole Blood from EPD

Each blood collection bag containing the fresh whole blood was prepared for centrifugation by sealing one line of the bag with a tube sealer and by taping the other line of the bag with the capped needle to the bag itself. Each blood collection bag was weighed and its weight recorded. The bags were paired according to weight and placed in a refrigerated centrifuge in opposing compartments and centrifuged for 10 minutes at 5,000 G at 4° C., to separate plasma from the cellular portion of the blood. Following centrifugation each blood collection bag was suspended from the prongs of the plasma expressor. Each blood collection bag was expressed individually into a 10 L transfer bag by means of a transfer tube. Hemostats were used to occlude the transfer tube when switching out the blood collection bags during the transfer procedure. During the transfer the 10 L transfer bag was sustained at 4° C. by means of ice packs. Once the 10 L transfer bag was charged with plasma from fresh whole blood collection from the different EPDs, the plasma was dispensed into custom product bags in aliquots of 1 L, based on weight (i.e., 1,000 g is equivalent to 1 L). The plasma was dispensed by means of a dispensing tube that connected the 10 L transfer bag to each custom product bag. Hemostats were used to occlude the dispensing tube when switching out the custom product bags during the dispensing procedure. Each custom product bag filled with plasma was purged of excess air, weighed to confirm volume by weight, and sealed with a tube sealer. The custom bag was labeled with lot number, expiration date, and stored on a flat surface at −20° C.

Source and Description of USDA Licensed Commercial Plasma Products

At the time of this study, three USDA Licensed commercially available *R. equi* specific plasma products were available for purchase.

Commercial Plasma 1 is the EQUIPLAS® Equine IgG-*Rhodococcus Equi* Antibody, Equine Origin product purchased from Plasvacc (Templeton, Calif.). The serial number used for testing was 33008686 with an expiration date of 16 Mar. 2012. This product claims that it is for use in horses and that it can be administered to foals for the treatment of failure of passive transfer (FPT) and/or as an aid in the management and control of respiratory disease associated with *Rhodococcus equi*. This product is licensed under US Vet Lic No 360.

Commercial Plasma 2 is the ReSolution *Rhodococcus Equi* Antibody, Equine Origin product purchased from MG Biologics (Ames, Iowa). The serial number used for testing was SL3000-057-10 with an expiration date of 26 Feb. 2013. This product claims that it is intended for use as an aid in the control of foal pneumonia caused by *Rhodococcus equi* by reducing disease severity. This product is licensed under US Vet Lic No 614.

Commercial Plasma 3 is the *Rhodococcus Equi* Antibody, Equine Origin PNEUMOMUNE-RE product purchased from Lake Immunogenics, Inc. (Ontario, N.Y.). The serial number used for testing was REN050809 with an expiration date of May 8, 2012. This product claims that it is for intravenous use in the horse as an aid in the control of disease caused by *Rhodococcus equi* infection in the neonate. This product is licensed under US Vet Lic No 318.

Administration of Commercial Plasma or *Rhodococcus equi* Hyperimmune Plasma to Foals Foals were positioned in right lateral recumbency and ophthalmic ointment was placed into each eye. The left jugular vein was clipped and prepped by cleansing the area with betadine scrub and rinsing with 70% alcohol. A small amount (<1 ml) of 2% lidocaine was placed subcutaneously in the area of the intravenous catheter placement using a 21-gauge needle and 3 cc syringe. Each of the 30 2010 foals received 1 L of commercial plasma 1, a USDA licensed plasma hyperimmunized for *R. equi*, 24 hours after birth and 21 days after birth. The commercial plasma was administered intravenously (IV) via the jugular at a slow rate over a period of approximately 30-45 minutes. A 16 gauge, 2-inch catheter was placed in the left jugular vein using strict aseptic technique in each of the 2011 and 2012 foals. A 6 ml syringe was attached to the catheter and a small blood sample was taken to assay the IgG level prior to REHIP administration. Each of the 30 2011 and 31 2012 foals received 1 L of REHIP 24 hours after birth. The REHIP was administered (IV) via the jugular vein at a slow rate over a period of 30-45 minutes. All foals were monitored for side effects associated with rapid plasma administration such as trembling, increased heart rate, increased respiration rate, increased capillary refill time and change in mucous membrane color from pink to pale pink or gray. If any of the side effects were noted, the flow of plasma was slowed or halted until the side effects abated. After plasma administration was complete, the IV catheter was removed and the jugular venipuncture site was treated with povidone-iodine ointment. The site was monitored for any potential formation of a hematoma or continued bleeding from the site. The foal was monitored for 5-10 minutes following plasma administration for any other clinical signs or side effects.

Administration of *Rhodococcus* Equi Vaccine to Pregnant Mares and Foals

2012 Mares and Foals: Vaccinated with VapAVapC, VapA, or VapC Vaccine

In 2012, 31 mares were vaccinated with VapAVapC, VapA, or VapC vaccine. Ten pregnant mares were immunized with three 1 ml doses of VapAVapC vaccine. The initial VapAVapC vaccine dose was administered at 7-9 months of pregnancy based on the last breeding date of the mare. The first boost was administered 2 weeks from the initial vaccination. The second boost was administered within 1 month of the projected foaling date based on the last breeding date of the mare. Two of the 2012 mares vaccinated with the VapAVapC vaccine had an additional boost within 2 months of the projected foaling, and their scheduled boost within 1 month of the projected foaling with the VapAVapC vaccine, for a total of four 1 ml doses. Eleven 2012 pregnant mares were immunized with three 1 ml doses of VapA vaccine. The initial VapA vaccine dose was administered at 7-9 months of pregnancy based on the last breeding date of the mare. The first boost was administered 2 weeks from the initial vaccination. The second boost was administered within 1 month of the projected foaling date based on the last breeding date of the mare. Eight 2012 pregnant mares were immunized with three 1 ml doses of VapC vaccine. The initial VapC vaccine dose was administered at 7-9 months of pregnancy based on the last breeding date of the mare. The first boost was administered 2 weeks from the initial vaccination. The second boost was administered within 1 month of the projected foaling date based on the last breeding date of the mare. Two 2012 pregnant mares were boosted within 2 months of the projected foaling and their scheduled boost within 1 month of the projected foaling with the VapC vaccine, for a total of four 1 ml doses.

The side of the neck of each mare was swabbed with 70% alcohol and the vaccine was administered in the muscle of the neck using a 21 gauge by 1-inch needle attached to a 3 ml syringe housing the vaccine. All vaccines were administered aseptically. Following each vaccine administration, the mare was monitored for any clinical signs of local pain, heat or swelling at the injection site as well as any other systemic signs of clinical illness such as fever, lethargy or anorexia.

The 31 foals from the 2012 mares were immunized with four 250 microliter doses of vaccine. Of the 2012 foals, 10 foals from the 10 mares vaccinated with VapAVapC were vaccinated with VapAVapC, 10 foals from the 10 mares vaccinated with VapC were vaccinated with VapC, and 11 foals from the 11 mares vaccinated with VapA were vaccinated with VapA vaccine. The initial vaccine was administered at 6 weeks from the date of birth (DOB). The first, second and third boosts were administered 8, 12, and 16 weeks from DOB. The region of the thigh below the brim of the pelvis of each foal was swabbed with 70% alcohol and the vaccine was administered in the muscle of the thigh using a 21 gauge by 1-inch needle attached to a 1 ml tuberculin syringe housing the vaccine. All vaccines were administered aseptically. Following each vaccine administration, the foal was monitored for any clinical signs of local pain, heat or swelling at the injection site as well as any other systemic signs of clinical illness such as fever, lethargy or anorexia. All foals had their temperature checked in the morning and in the afternoon every day. The 2012 foals that were vaccinated with VapA were administered VapA plasma from the 2012 donors, foals that were vaccinated with VapAVapC were administered VapA VapC plasma from the 2012 donors, and foals that were vaccinated with only VapC vaccine were administered with VapC plasma from the 2011 donors 24 hours after birth.

2011 Mares and Foals: Vaccinated with VapC Vaccine

In 2011, 30 pregnant mares were immunized with three 1 ml doses of VapC vaccine using the same administration technique as described for the 2012 mares. The initial vaccine dose was administered at 7-9 months of pregnancy based on the last breeding date of the mare. The first boost was administered 2 weeks from the initial vaccination. The second boost was administered within 1 month of the projected foaling date based on the last breeding date of the mare. The side of the neck of each mare was swabbed with 70% alcohol and the vaccine was administered in the muscle of the neck using a 21 gauge by 1-inch needle attached to a 3 ml syringe housing the vaccine. All vaccines were administered aseptically. Following each vaccine administration, the mare was monitored for any clinical signs of local pain, heat or swelling at the injection site as well as any other systemic signs of clinical illness such as fever, lethargy or anorexia.

In 2011, 30 foals were vaccinated with the VapC vaccine. The foals were divided into three groups: Group 1 with 18 foals were vaccinated at approximately 2, 6, 10, and 14 weeks after DOB; Group 2 with 2 foals, were vaccinated at approximately 4, 7, 11 and 15 weeks after DOB; and Group 3 with 10 foals, were vaccinated at approximately 4, 6, 10, and 14 weeks after DOB. The region of the thigh below the brim of the pelvis of each foal was swabbed with 70% alcohol and the vaccine was administered in the muscle of the thigh using a 21 gauge by 1-inch needle attached to a 1 ml tuberculin syringe housing the vaccine. All vaccines were administered aseptically. Following each vaccine administration, the foal was monitored for any clinical signs of local pain, heat or swelling at the injection site as well as any other systemic signs of clinical illness such as fever, lethargy or anorexia. All foals had their temperature checked in the morning and in the afternoon every day. All foals were administered REHIP plasma from the 2011 donors vaccinated with the VapC, 24 hours after birth.

Presumed *Rhodococcus equi* Foals

Foals were presumed to be *R. equi* positive if they displayed the following signs: non-productive coughs, fever (temperature persistently >101.5° C.), nasal discharge, and multiple, large persistent abscesses in their lungs determined by ultrasound evaluation. These presumed *R. equi* positive foals remained symptomatic for long periods and were relatively non responsive to treatment with antibiotics such as Naxcel, Clarithromycin and Rifampin. A fecal sample from the single 2012 foal exhibiting these clinical signs was tested by Idexx Laboratory Services and reported to be positive for *R. equi*.

Presumed *Streptococcus zooepidemicus* Foals

Foals were presumed to be *S. zooepidemicus* positive if they displayed the following signs: mild and transient productive cough, nasal discharge, and either a normal temperature or fever (temperature >101.5° C.). Presumed *S. zooepidemicus* positive foals responded rapidly to Naxcel antibiotic treatment and did not require treatment with much stronger antibiotics such as Clarithromycin and Rifampin used to treat presumed *R. equi* positive foals.

VapC Peptide Design and Synthesis

Epitope Mapping of the VapC Protein of *R. equi*

The protein accession numbers were determined by using the National Center for Biotechnology database. The VapC accession number used was NP 066767. Protein Sequence Mark-up Tool was used to help design the conjugated peptide sequences. All peptides were 15 amino acids long and overlapped by 4 amino acids. Sixteen VapC peptides were designed: VapC-01—SEQ ID No. 32, VapC-02—SEQ ID No. 33, VapC-03—SEQ ID No. 34, VapC-04—SEQ ID No. 35, VapC-05—SEQ ID No. 36, VapC-06—SEQ ID No. 37, VapC-07—SEQ ID No. 38, VapC-08—SEQ ID No. 39, VapC-09—SEQ ID No. 40, VapC-10—SEQ ID No. 41, VapC-11—SEQ ID No. 42, VapC-12—SEQ ID No. 43, VapC-13—SEQ ID No. 44 VapC-14—SEQ ID No. 45, VapC-15—SEQ ID No. 46, and VapC-16—SEQ ID No. 47.

```
VapC-01 SEQ ID No. 32:
MFRVGRPSKSIAVVAC

VapC-02 SEQ ID No. 33:
AVVASVLCFLALGGTK
```

```
VapC-03 SEQ ID No. 34:
LGGTARANVVAPSAWK

VapC-04 SEQ ID No. 35:
CPSAWGGAQSAADKEG

VapC-05 SEQ ID No. 36:
DKEGEGVTLGGVGVLC

VapC-06 SEQ ID No. 37:
VGVLRPHNKDADEQYC

VapC-07 SEQ ID No. 38:
DEQYTVHGVVVSALFK

VapC-08 SEQ ID No. 39:
SALFYNHLRISVDGGK

VapC-09 SEQ ID No. 40:
KVDGGMTFDGDGGGLS

VapC-10 SEQ ID No. 41:
GGLSTPGGGALWGTLK

VapC-11 SEQ ID No. 42:
WGTLTTSDLQQLYDEK

VapC-12 SEQ ID No. 43:
KLYDETASFECNAVGP

VapC-13 SEQ ID No. 44:
KAVGPYLNINFYDSYG

VapC-14 SEQ ID No. 45:
DSYGRILASVQAGGVK

VapC-15 SEQ ID No. 46:
KAGGVSTMIGIGGGNG

VapC-16 SEQ ID No. 47:
KTMIGIGGGNGRWHLV
```

Synthetic Peptide Synthesis

A one-hour coupling time was used for the coupling of amino acids. The peptides marked as Ac-capped received an additional coupling step with Acetic Anhydride. The peptide sequence was removed from the resin by using standard cleavage protocols. To pass QC standards HPLC and Mass Spec standards were followed, all peptides must have a percent purity determined by HPLC to be greater than or equal to 40%.

Cleavage Protocol

A cleavage cocktail was prepared to remove the peptide sequence from the resin. The cocktail consisted of 88% TFA (Trifluoroacetic Acid), 5% Phenol, Liquified, 5% MQ Water and 2% Tris (Triisopropylsilane). 1 ml of cocktail was dispensed per peptide. The cocktail and resin mixed for 2.5-3 hours. The mixture was drained into 4 ml vials and the resin was rinsed with 0.5 ml of the cocktail. The content of each vial was transferred to a pre-labeled conical with 10 mL of chilled Diethyl Ether to begin the precipitation process. Each conical was spun in a centrifuge at 1400 RPM for 4 minutes. Once completed, the supernatant was poured off and 7 mL of Ether was added. The conical was mixed by hand to break up the remaining pellet and spun down for another 4 minutes. Pouring off the supernatant and mixing to break up the pellet was repeated one more time. After the final spin, the supernatant was poured out and the remaining pellet was allowed to air out and dry overnight in a flow hood, covered with a large Kim Wipe.

Dissolution

After the overnight in the flow hood the cleaved peptides were removed from the hood and all pellets were crushed into fine powder. 7 mL of MQ water was added to each peptide, capped and mixed on an orbital shaker for 35 minutes at 400 RPM. Ammonium Hydroxide was added to any peptide that was insoluble in water. The dissolved peptide was then transferred to the pre-labeled scintillation vial. HPLC and Mass Spec analysis samples were made. All vials were capped and freeze dried in liquid nitrogen. When frozen, the vials were removed and un-capped and placed in a lyophilizer jar. The jar was placed on a lyophilizer and ran for 2 days at −80° C. under vacuum.

HPLC Analysis

HPLC samples were made by using the dissolved peptide from the dissolution step. 250 µL of dissolved sample was aliquoted to a pre-labeled HPLC vial. 500 µL of MQ water was aliquoted to dilute the sample. The HPLC vial was capped and placed in the HPLC machine. The sample ran for 12 minutes over the HPLC column on a gradient. The gradient started at 0% Acetonitrile (w/0.1% TFA) and 100% MQ water (w/0.1% TFA). The run finished at 50% Acetonitrile and 50% MQ water. A final wash of 100% Acetonitrile was performed to flush the column. The results were analyzed when completed. The main peak should comprise over 40% of the overall run. The second largest peak should be less than half of the main peak (i.e. if main peak was 42%, the second largest peak should be less than 21%). If the sequence contained either a W or a Y, the UV spectrum was checked for presence of the correct wavelength.

Mass Spec Analysis

The Mass Spec samples were made by using the dissolved peptides from the dissolution step. The matrix comprised a-Cyano-4-hydroxycinnamic acid dissolved in a solvent of 70% Acetonitrile (w/0.1% TFA) and 30% MQ Water (w/0.1% TFA). The ratio was 10 mg per 1 mL. 0.5 µl of the matrix was aliquoted into a clean Mass Spec plate for each sample. 0.5 µl of the dissolved peptide was aliquoted onto the matrix. The plate was loaded onto the Mass Spec and the sample was aligned with the laser and shoot sample. The results were analyzed when completed. For the sample to pass the molecular weight of the peptide, the shot should have fallen within the range of −10 up to +50 of the calculated MW. The largest peak was within the passing range. Other peaks were smaller than the correct peak.

When the peptide was removed from the lyophilizer and capped, a re-run of the samples that required additional HPLC or Mass Spec analysis was performed. If the peptide passed HPLC and Mass Spec, the peptide was used in the ELISA test.

ELISA Assay to Measure VapA, -C, -D, -E and or -G Antibody Titers in Test Bleed and Plasma Samples VapA and -C titers from test bleed and plasma samples were measured using ELISA assays with synthetically derived VapA and VapC peptides as well as a GST-tagged VapA (SEQ ID No. 19), GST-tagged VapC (SEQ ID No. 21), GST-tagged VapD (SEQ ID No. 29), GST-tagged VapE (SEQ ID No. 30), or GST-tagged VapG (SEQ ID No. 31) antigen to eliminate non-target cross-reactions for the recombinant proteins. The plates were coated with either the peptide of interest or the recombinant proteins. Each plate was diluted in a TRIS based solution, the overall concentration yields 50 ng of protein per coated well. Each coated plate was incubated overnight at 4° C. and blocked the following day w/ELISA Bovine Serum Albumin (BSA). Samples were tested by combining samples with ELISA BSA in dilution plates such that the following serial dilutions were made: 1/20, 1/80, 1/320, 1/1280, 1/5120, 1/20480. The diluted sample was transferred to the corresponding ELISA plate and incubated at room temperature for 1 hour. The solution was discarded and the plate was washed with PBS/Tween-20. The secondary antibody solution (goat anti-horse IgG-AP/BSA) was added to each ELISA plate well and incubated for 1 hour at room temperature. The solution was discarded and the plate was washed with PBS/Tween-20. The PNPP substrate solution was added and the plate was incubated for 10 minutes at room temperature. The absorbance was read on an ELISA reader and titers were recorded at an absorbance of ~0.500 (rounding up to the nearest ones).

VapA and VapC Protein Percent Identities

The percent identities between each protein sequence were found by using NCBI BLAST sequence comparison tools. Each protein accession number was aligned with the correct protein sequence to get the percent identities of each. The accession numbers for each Vap was: VapA-NP_066765, VapB-YP_002149601, VapC-NP_066767, VapK2-YP_002149598, Vapk1-YP_002149595, VapM-YP_002149599, VapL-YP_002149597, VapJ-YP_002149592, VapX-RLYDETGPFDFNAAGLFMNV DHFGYRA.

Ultrasound Procedure for Detection of Lung Abscesses in Foals

Thoracic ultrasound examinations were performed on foals using a MicroMaxx Ultrasound System (Sonosite, Inc.). Examinations of the left and right thoraxes were performed using a 5 MHz linear ultrasound probe. Findings were scored for the caudodorsal and cranioventral quadrants on both sides, and any significant pathology, such as abscesses, were identified, measured and images saved. Two-second video clips were retained for each scored quadrant.

Results and Discussion:

Average Mare Titers

The antibody titer levels of VapA, -C, -D, -E, and -G, were measured from the 2012 mares vaccinated with recombinant VapC only, recombinant VapA only, or the recombinant VapA VapC combination (Table 3). Mare test bleed samples from pre- and post-vaccinations were measured using ELISA and tested against the VapA, -C, -D, -E, and -G recombinant proteins. The averaged antibody titer levels show that mares vaccinated with VapA only have higher VapA titers at 14-days post-vaccination (11,535) and at post-foaling (19,304), in comparison to VapC titer at 14-days post vaccination (104) and at post-foaling (241). VapA only vaccinated mares have higher titers against VapA, -E, -D, and -G for both 14-days post vaccination and post-foaling, than VapC only vaccinated mares. Although VapC only vaccinated mares have low titers against VapA, -C, -D, -E, and -G, they have higher VapC titers than VapA only vaccinated mares. Mares vaccinated with the combination vaccine show higher VapC titer levels at 14-days post vaccine (4097), than VapA titer levels at 14-days post vaccine (2982). However, the opposite is observed for titer levels of VapC and VapA at post-foaling. The VapA titer levels at post-foaling (5998) are higher than that of VapC at post-foaling (2617). VapA VapC vaccinated mares have elevated titers in comparison to pre-vaccinated titers for all the Vap proteins, not observed in VapA or VapC only vaccinated mares. Mares vaccinated with VapA, VapC, or VapAVapC combination vaccine clearly show elevated titer levels against their respective proteins and VapD, -E, and -G recombinant proteins after vaccination and at post-foaling. Additionally, VapC only vaccinated mares show relatively high post-foaling titer against VapA in comparison to VapA only against VapC. VapA only vaccinated mares show higher titers against VapD, -E, -G than VapC only vaccinated mares.

This data shows that foals are receiving high antibody titers against all the Vap proteins when they are born from a mare vaccinated with VapA VapC.

TABLE 3

Comparison of average Vap protein antibody titers in serum collected from VapA, VapC, and VapA/VapC immunized mares:

| | VapA Titer | VapC Titer | VapD Titer | VapE Titer | VapG Titer |
|---|---|---|---|---|---|
| VapA Immunized Mares: | | | | | |
| Pre-vaccination | 69 | 59 | 30 | 88 | 35 |
| 14 days post-initial vaccination | 11535 | 104 | 2713 | 1807 | 1124 |
| Within 24 hours of foaling | 19304 | 241 | 15564 | 3538 | 4402 |
| VapC Immunized Mares: | | | | | |
| Pre-vaccination | 44 | 224 | 34 | 93 | 60 |
| 14 days post-initial vaccination | 991 | 5026 | 422 | 1044 | 426 |
| Within 24 hours of foaling | 1764 | 5692 | 1110 | 808 | 2422 |
| VapA/VapC Immunized Mares: | | | | | |
| Pre-vaccination | 101 | 125 | 120 | 152 | 97 |
| 14 days post-initial vaccination | 2982 | 4097 | 4330 | 15171 | 3957 |
| Within 24 hours of foaling | 5998 | 2617 | 5048 | 6332 | 5939 |

Results are expressed as average ELISA titers from 3 different VapA immunized mares, 3 different VapC immunized mares and 3 different VapA/VapC immunized mares.

Donor/Plasma Average Titers

The average antibody titers for the VapA, -C, -D, -E, and -G were also measured for donor horses vaccinated with the recombinant VapC vaccine in 2011, and for the 2012 donor horses vaccinated with recombinant VapA, or the VapA VapC combination vaccine (Table 4). Donor test bleed samples from pre- and post-vaccination were tested using an ELISA and tested against the VapA, -C, -D, -E, and -G recombinant proteins. Across all donor groups vaccinated there is a significant increase in titer levels compared to pre-vaccination titer levels. Donors vaccinated with the VapA VapC and VapC vaccine show high levels for all the Vap proteins in comparison to VapA vaccinated donors. In addition, the VapAVapC vaccinated donors show higher VapA titer levels in comparison to VapC titer levels for post-vaccination titers. Donors vaccinated with VapC show elevated titers against VapA and VapC recombinant protein, while VapA only donors show elevated levels for VapA and not for VapC. Donors vaccinated with VapAVapC show higher titers against VapD, -E, and -G than only VapA or VapC vaccinated donors. Therefore, vaccinating with VapAVapC provides the most protection against all Vap proteins compared to vaccinating with VapA alone or VapC alone.

TABLE 4

Comparison of average Vap protein antibody titers in serum collected from representative VapA, VapC, and VapA/VapC immunized plasma donor horses:

| | VapA Titer | VapC Titer | VapD Titer | VapE Titer | VapG Titer |
|---|---|---|---|---|---|
| VapA Immunized Donors: | | | | | |
| Pre-vaccination | 103 | 179 | 19 | 74 | 101 |
| Post-vaccination* | 13914 | 924 | 5820 | 2654 | 2338 |

TABLE 4-continued

Comparison of average Vap protein antibody titers in serum collected from representative VapA, VapC, and VapA/VapC immunized plasma donor horses:

| | VapA Titer | VapC Titer | VapD Titer | VapE Titer | VapG Titer |
|---|---|---|---|---|---|
| VapC Immunized Donors: | | | | | |
| Pre-vaccination | 102 | 115 | 123 | 212 | 61 |
| 56 days post-vaccination | 2407 | 3706 | 2020 | 3611 | 7324 |
| VapA/VapC Immunized Donors: | | | | | |
| Pre-vaccination | 74 | 69 | 74 | 145 | 70 |
| 14 days post-vaccination | 10451 | 2819 | 4032 | 4332 | 5291 |

Results are expressed as average ELISA titers from 3 different donor horses immunized with VapA, 5 different donor horses immunized with VapC, and 11 different donor horses immunized with VapA/VapC.
*ELISA titers are averaged from serum collected 63 days post-vaccination for 2 different donor horses and 105 days post-vaccination for 1 donor horse immunized with VapA.

Plasma samples collected from VapA, VapC, and VapAVapC vaccinated donors were also tested using an ELISA for VapA, -C, -D, -E, and -G titer levels (Table 5). All samples from the vaccinated donors show an increase in ELISA antibody titers against their respective recombinant proteins. Plasma from donor horses vaccinated with VapA had the highest Vap protein titer concentrations of VapA, -D, -E, and -G, in comparison to VapAVapC and VapC only vaccinated donors. Although plasma from VapA donors had the highest titers for VapA, -D, -E, and -G, plasma from VapAVapC vaccinated donors had high titers against all the Vap proteins. Plasma from VapC only vaccinated donors had the lowest titers against VapA, -D, and -E. Therefore plasma from VapAVapC vaccinated donors has protection against all Vap proteins.
Table 5

TABLE 5

Comparison of Vap protein antibody titers in pooled R. equi hyperimmune plasma collected from VapA, VapC, and VapA/VapC immunized plasma donor horses:

| | VapA Titer | VapC Titer | VapD Titer | VapE Titer | VapG Titer |
|---|---|---|---|---|---|
| VapA Plasma | 20480 | 3120 | 9147 | 13276 | 11418 |
| VapC Plasma | 3541 | 7612 | 2212 | 5771 | 3340 |
| VapA/VapC Plasma | 17000 | 4758 | 5397 | 8798 | 3117 |

Results are expressed as ELISA titers from plasma from 1 donor horse immunized with VapA, plasma pooled from 5 different donor horses immunized with VapC, and plasma pooled from 9 different donor horses immunized with VapA/VapC.

Three different USDA licensed commercial plasmas: 1, 2, and 3 that are hyperimmunized for R. equi, were tested through an ELISA using the same antibodies used to measure the Vap antibody titer levels in the VapA, VapC, or VapAVapC vaccinated mare and donor test bleed samples (Table 6). Commercial plasma 3 had the lowest Vap antibody concentrations, ranging from 88-1565, with VapC at a low titer of 88. Commercial plasma 1 and 2 had the lowest antibody titer concentrations of VapC titers of all the Vap protein antibody titers. Surprisingly, commercial plasma 3 had low titers across the board of all the Vap proteins in comparison to commercial plasma 1 and 2, with slightly elevated titer levels for VapA and VapD only. Commercial plasma 1 and 2 samples show elevated ELISA antibody titers against VapA, -D, -E, and -G. VapD had the highest measured Vap titer of all Vap antibodies in all three commercial samples. In comparison to USDA licensed commercially available plasma, plasma collected from the VapA, VapC, or VapAVapC vaccinated donors had strong antibody titers. In particular, VapC titers were much higher in VapA, VapC and VapAVapC plasma than those observed in USDA licensed commercial plasma.

TABLE 6

Comparison of average Vap protein antibody titers in USDA licensed commercial plasma from R. equi immunized plasma donor horses:

| | VapA Titer | VapC Titer* | VapD Titer | VapE Titer | VapG Titer |
|---|---|---|---|---|---|
| Commercial Plasma 1 | 8706 | 329 | 10256 | 9242 | 4810 |
| Commercial Plasma 2 | 9720 | 374 | 10922 | 5585 | 5847 |
| Commercial Plasma 3 | 1565 | 88 | 1019 | 448 | 353 |

Results are expressed as ELISA titers from R. equi hyperimmune plasma purchased from three different suppliers.
*Note the low VapC Titers in USDA licensed commercial plasma (Table 5) compared to the VapC Titers in plasma from VapA, VapC, and VapA/VapC immunized donor horses (Table 4).

2011 Foal Average Titers

The 2011 foals were orally administered hyper-immunized colostrum raised against VapC recombinant protein and IV administered 1 L of REHIP at 1 day after birth (Table 7). In addition, 2011 foals were vaccinated with VapC recombinant protein four times. The 2011 foals were divided into three groups that received their initial vaccination at approximately 15, approximately 20, or at 30 days post DOB. Test bleed samples from the 2011 foals vaccinated with VapC were used to measure titer levels of VapA, -C, -D, -E, and -G (Table 8). The average titer concentration of VapA, VapD and VapG at the points 0, 2, 90, and 180 days shows a steady increase at 90 days, and a slow decrease over time through 180 days. The VapE titers for the three groups show a slow steady drop in titer concentration from the initial vaccination. The average titer concentration of VapC shows a high concentration at birth and at 2 days after birth, with an exponential decrease in titer concentration as the foals reach 200 days. The three groups vaccinated at approximately 15, 20, or 30 days after birth all have very high VapC titer concentrations after birth.

TABLE 7

Comparison of individual VapC antibody titers in serum collected pre- and post-plasma administration from 2011 foals (0-2 days old) born to VapC immunized mares:

| | Foal ID | Pre-Plasma* VapC Titer | Post-Plasma** VapC Titer |
|---|---|---|---|
| Foals who received colostrum from their VapC immunized dams and plasma from VapC immunized donors | E-1101 | 19229 | 19477 |
| | E-1102 | 837 | 3012 |
| | E-1103 | 1111 | 376 |
| | E-1104 | 364 | 464 |
| | E-1105 | 754 | 817 |
| | E-1106 | 1991 | 1715 |
| | E-1107 | 2551 | 2095 |
| | E-1108 | 3110 | 2593 |
| | E-1109 | 3500 | 3448 |
| | E-1110 | 4536 | 3499 |
| | E-1111 | 439 | 631 |
| | E-1112 | 1780 | 1902 |
| | E-1113 | 2664 | 2367 |
| | E-1114 | 142 | 361 |
| | E-1115 | 7392 | 6528 |
| | E-1116 | 1959 | 1567 |
| | E-1117 | 5250 | 4509 |
| | E-1118 | 16002 | 8417 |
| | E-1119 | 20480 | 15012 |
| | E-1120 | 11837 | 7709 |
| | E-1121 | 4486 | 1754 |

TABLE 7-continued

Comparison of individual VapC antibody titers in serum collected
pre- and post-plasma administration from 2011 foals (0-2 days old)
born to VapC immunized mares:

| Foal ID | Pre-Plasma* VapC Titer | Post-Plasma** VapC Titer |
|---|---|---|
| E-1122 | 11501 | 12123 |
| E-1123 | 5622 | 6356 |
| E-1124 | 1485 | 2173 |
| E-1125 | 1682 | 1582 |
| E-1126 | 8524 | 9657 |
| E-1127 | 5128 | 5679 |
| E-1128 | 2833 | 3560 |
| E-1129 | 2515 | 2856 |
| E-1130 | 2819 | 2170 |

Results are expressed as ELISA titers.
*Pre-plasma serum was collected within 24 hours of foaling after foals had received colostrum from their dams, but prior to receiving plasma.
**Post-plasma serum was collected approximately 24 hours after receiving plasma.

2012 Foal Average Titers

The 2012 foals were orally administered hyper-immunized colostrum raised against VapA, VapC or VapAVapC recombinant protein and IV administered 1 L of REHIP at 1 day after birth (Table 9). In addition, 2012 foals were vaccinated with VapA, VapC, or VapAVapC recombinant protein four times, at 6, 8, 12, and 16 weeks of age. Test bleed samples from vaccinated 2012 foals were tested with an ELISA to measure the antibody titers of VapA, -C, -D, -E, and -G against their respective recombinant proteins (Table 10). The 2012 foal test bleed samples post-hyper-immunized orally administered colostrum (day 0 test bleed) and post-REHIP (day 2 test bleed) show elevated ELISA antibody titers against their respective recombinant proteins, with post-plasma titers only slightly higher.

Foals that received VapA only colostrum and plasma show the highest ELISA antibody titers against VapD, -E, and -G, in comparison to foals that received VapC, or VapAVapC colostrum and plasma, but do not have elevated

TABLE 8

Comparison of average Vap protein antibody titers in serum collected from 2011 VapC immunized foals
(0-180 days old) born to VapC immunized mares:

| | Average Age (days) | VapA Titer | VapC Titer | VapD Titer | VapE Titer | VapG Titer |
|---|---|---|---|---|---|---|
| Foals who received | 0* | 111 | 6240 | 1211 | 1273 | 1154 |
| colostrum from their | 2** | 72 | 5547 | 1137 | 947 | 851 |
| VapC immunized | 15*** | — | 4411 | — | — | — |
| dams, plasma from | 30 | — | 2095 | — | — | — |
| VapC immunized | 45 | — | 1111 | — | — | — |
| donors, and VapC | 60 | — | 691 | — | — | — |
| vaccine at | 75 | — | 448 | — | — | — |
| approximately 2, 6, 10, | 90 | 417 | 526 | 852 | 610 | 1419 |
| and 14 weeks old | 105 | — | 373 | — | — | — |
| (Group 1) | 120 | — | 381 | — | — | — |
| | 135 | — | 256 | — | — | — |
| | 150 | — | 140 | — | — | — |
| | 165 | — | 96 | — | — | — |
| | 180 | 56 | 63 | 170 | 104 | 223 |
| Foals who received | 0* | 23 | 1110 | 223 | 439 | 230 |
| colostrum from their | 2** | 12 | 1267 | 221 | 430 | 222 |
| VapC immunized | 30 | — | 604 | — | — | — |
| dams, plasma from | 45 | — | 377 | — | — | — |
| VapC immunized | 60 | — | 121 | — | — | — |
| donors, and VapC | 75 | — | 115 | — | — | — |
| vaccine at | 90 | 514 | 157 | 365 | 353 | 243 |
| approximately 3, 7, 11 | 105 | — | 109 | — | — | — |
| and 15 weeks old | 120 | — | 201 | — | — | — |
| (Group 2) | 135 | — | 153 | — | — | — |
| | 150 | — | 95 | — | — | — |
| | 165 | — | 48 | — | — | — |
| | 180 | 54 | 30 | 66 | 87 | 52 |
| Foals who received | 0* | 37 | 3798 | 350 | 578 | 299 |
| colostrum from their | 2** | 41 | 1876 | 495 | 824 | 374 |
| VapC immunized | 30 | — | 712 | — | — | — |
| dams, plasma from | 45 | — | 495 | — | — | — |
| VapC immunized | 60 | — | 491 | — | — | — |
| donors, and VapC | 75 | — | 297 | — | — | — |
| vaccine at | 90 | 648 | 238 | 732 | 305 | 441 |
| approximately 4, 6, 10, | 105 | — | 131 | — | — | — |
| and 14 weeks old | 120 | — | 150 | — | — | — |
| (Group 3) | 135 | — | 250 | — | — | — |
| | 150 | — | 455 | — | — | — |
| | 165 | — | 254 | — | — | — |
| | 180 | 164 | 161 | 415 | 234 | 1095 |

Results are expressed as average ELISA titers. VapC titers are averaged from 18 foals in Group 1, 2 foals in Group 2 and 10 foals in Group 3. VapA, VapD, VapE and VapG titers are averaged from 3 foals in Group 1, 2 foals in Group 2 and 3 foals in Group 3.
A dash (—) indicates that the sample was not tested.
*Pre-plasma serum was collected within 24 hours of foaling after foals received colostrum from their dams, but prior to receiving plasma.
**Post-plasma serum was collected approximately 24 hours after receiving plasma. Individual titers in serum collected pre- and post-plasma are represented in Table 7.
***No sample was taken at 15 days for Groups 2 and 3.

titers against VapC. Foals that received VapC only colostrum and plasma show elevated titers against VapA and VapC recombinant protein. Foals that received VapAVapC colostrum and REHIP show similar high ELISA antibody titers against VapA, -C, -D, -E, and -G. Additionally, ELISA antibody titers drop slowly over the course of 24 weeks for VapA, VapC or VapAVapC recombinant protein vaccinations. VapA only immunized foals show a spike in VapA protein titer after their third vaccination. VapC only immunized foals show a spike in VapA protein titer after their third vaccination. VapAVapC immunized foals show a spike in antibody titer after the fourth vaccination.

TABLE 9

Comparison of individual VapA and VapC antibody titers in serum collected pre- and post-plasma administration from 2012 foals (0-2 days old) born to VapA, VapC, and VapA/VapC immunized mares:

| | Foal ID | Pre-Plasma* VapA Titer | Post-Plasma** VapA Titer | Pre-Plasma* VapC Titer | Post-Plasma** VapC Titer |
|---|---|---|---|---|---|
| Foals who received colostrum from their VapA immunized dams and plasma from VapA immunized donors | E-1202 | 4819 | 7795 | 729 | 725 |
| | E-1204 | 434 | 5394 | 0 | 56 |
| | E-1211 | 6676 | 9744 | 95 | 124 |
| | E-1215 | 4605 | 6560 | 135 | 114 |
| | E-1217 | 4674 | 6162 | 313 | 215 |
| | E-1218 | 3512 | 4090 | 103 | 253 |
| | E-1220 | 5587 | 4563 | 119 | 88 |
| | E-1221 | 20510 | 19992 | 192 | 803 |
| | E-1222 | 21690 | 20490 | 125 | 108 |
| | E-1223 | 23719 | 20497 | 87 | 79 |
| | E-1224 | 26265 | 39875 | 179 | 1193 |
| Foals who received colostrum from their VapC immunized dams and plasma from VapC immunized donors | E-1203 | 696 | 1475 | 2370 | 3487 |
| | E-1205 | 1068 | 1674 | 907 | 1850 |
| | E-1209 | 2261 | 1621 | 4681 | 3465 |
| | E-1210 | 492 | 939 | 1533 | 2126 |
| | E-1212 | 1161 | 2508 | 3554 | 5956 |
| | E-1214 | 1132 | 2918 | 2524 | 3704 |
| | E-1225 | 704 | 1791 | 12939 | 14776 |
| | E-1226 | 5415 | 4340 | 5188 | 5042 |
| | E-1229 | 882 | 2931 | 2963 | 9901 |
| | E-1231 | 3136 | 2781 | 8054 | 8245 |
| Foals who received colostrum from their VapA/VapC immunized dams and plasma from VapA/VapC immunized donors | E-1201 | 2840 | 4696 | 571 | 1265 |
| | E-1206 | 2625 | 3255 | 2338 | 2274 |
| | E-1207 | 5250 | 3932 | 4038 | 2570 |
| | E-1208 | 4921 | 4260 | 2196 | 1964 |
| | E-1213 | 592 | 322 | 1490 | 1664 |
| | E-1219 | 5316 | 4442 | 1377 | 1015 |
| | E-1227 | 5441 | 5277 | 3462 | 4448 |
| | E-1228 | 7054 | 11479 | 11514 | 13423 |
| | E-1230 | 23591 | 20956 | 26561 | 24026 |
| | E-1232 | 12689 | 13062 | 4345 | 5502 |

Results are expressed as ELISA titers.
*Pre-plasma serum was collected within 24 hours of foaling after foals had received colostrum from their dams, but prior to receiving plasma.
**Post-plasma serum was collected approximately 24 hours after receiving plasma.

TABLE 10

Comparison of average Vap protein antibody titers in serum collected from 2012 VapA, VapC, and VapA/C immunized foals (0-168 days old) born to VapA, VapC, and VapA/VapC immunized mares, respectively:

| | Age (days) | VapA Titer | VapC Titer | VapD Titer | VapE Titer | VapG Titer |
|---|---|---|---|---|---|---|
| Foals who received colostrum from their VapA immunized dams, plasma from VapA immunized donors, and VapA vaccine at 6, 8, 12 and 16 weeks old (Group 4) | 0* | 11136 | 189 | 384 | 763 | 474 |
| | 2** | 13197 | 342 | 2922 | 2478 | 4132 |
| | 42 | 5713 | 119 | — | — | — |
| | 56 | 5019 | 113 | — | — | — |
| | 70 | 2970 | 288 | — | — | — |
| | 84 | 3079 | 243 | 702 | 488 | 770 |
| | 98 | 3086 | 420 | — | — | — |
| | 112 | 2125 | 275 | — | — | — |
| | 126 | 2808 | 428 | — | — | — |
| | 140 | 2507 | 278 | — | — | — |
| | 154 | 1486 | 196 | — | — | — |
| | 168 | 1118 | 144 | 162 | 102 | 159 |
| Foals who received colostrum from their VapC immunized dams, plasma from VapC immunized donors, and | 0* | 1695 | 4471 | 702 | 1010 | 1052 |
| | 2** | 2298 | 5855 | 1064 | 1748 | 1333 |
| | 42 | 1352 | 2013 | — | — | — |
| | 56 | 1433 | 1229 | — | — | — |
| | 70 | 1141 | 915 | — | — | — |

TABLE 10-continued

Comparison of average Vap protein antibody titers in serum collected from 2012 VapA, VapC, and VapA/C immunized foals (0-168 days old) born to VapA, VapC, and VapA/VapC immunized mares, respectively:

| | Age (days) | VapA Titer | VapC Titer | VapD Titer | VapE Titer | VapG Titer |
|---|---|---|---|---|---|---|
| VapC vaccine at 6, 8, 12 | 84 | 1049 | 696 | 258 | 308 | 381 |
| and 16 weeks old | 98 | 1338 | 1185 | — | — | — |
| (Group 5) | 112 | 1069 | 944 | — | — | — |
| | 126 | 1209 | 1859 | — | — | — |
| | 140 | 938 | 1254 | — | — | — |
| | 154 | 715 | 849 | — | — | — |
| | 168 | 460 | 567 | 83 | 112 | 80 |
| Foals who received | 0* | 7032 | 5789 | 1777 | 2593 | 2421 |
| colostrum from their | 2** | 7168 | 5815 | 1758 | 2162 | 2519 |
| VapA/VapC immunized | 42 | 2542 | 1232 | — | — | — |
| dams, plasma from | 56 | 1678 | 908 | — | — | — |
| VapA/VapC immunized | 70 | 1324 | 753 | — | — | — |
| donors, and VapA/VapC | 84 | 935 | 532 | 313 | 386 | 232 |
| vaccine at 6, 8, 12 and 16 | 98 | 865 | 745 | — | — | — |
| weeks old | 112 | 702 | 504 | — | — | — |
| (Group 6) | 126 | 1465 | 1086 | — | — | — |
| | 140 | 1088 | 669 | — | — | — |
| | 154 | 814 | 490 | — | — | — |
| | 168 | 644 | 381 | 189 | 130 | 226 |

Results are expressed as average ELISA titers. VapA and VapC titers are averaged from 11 foals in Group 4, 10 foals in Group 5 and 10 foals in Group 6. VapD, VapE and VapG titers are averaged from 2 different foals in Group 4, 4 different foals in Group 5, and 4 different foals in Group 6.
A dash (—) indicates that the sample was not tested.
*Pre-plasma serum was collected within 24 hours of foaling after foals received colostrum from their dams, but prior to receiving plasma.
**Post-plasma serum was collected approximately 24 hours after receiving plasma. Individual titers in serum collected pre- and post-plasma are represented in Table 9.

Foal Clinical Data

The 2010 foals were not orally administered hyper-immunized colostrum but were IV administered 1 L hyper-immunized plasma from commercial plasma 1 at 1 day old and again at 21 days of age. The 30 non-vaccinated 2010 foals that received commercial plasma were observed for clinical signs for 200 days (Table 11). Only 7 foals were presumed healthy out of the 30 (23%) observed foals. Thirteen of the non-vaccinated foals were presumed to be *R. equi* positive, and 10 were presumed to be *R. equi* and *S. zooepidemicus* positive, in which the diagnoses were based on how well the foals responded to antibiotic treatment. The 2010 sick foals were observed longer than 200 days. Out of the 23 foals presumed to be *R. equi* positive one foal died due to an *R. equi* infection. The high number of presumed *R. equi* positive foals suggests VapA commercial plasma, USDA approved for protection of *R. equi* infection in foals, is not enough to fully protect foals from an *R. equi* infection. The 30 foals vaccinated with recombinant VapC in 2011 (Table 12), and the 31 foals vaccinated with VapA, VapC, or VapAVapC vaccine combination in 2012 (Table 13) were observed for 200 days for any sign of clinical symptoms. Nineteen of the 30 (63%) vaccinated 2011 foals were presumed healthy throughout the 200 days of observation. Eleven 2011 foals were presumed to be *S. zooepidemicus* positive and none of the foals were presumed to be *R. equi* positive. In 2012, 30, of the 31 (97%) vaccinated foals were presumed to be healthy. Only one 2012 foal was presumed to *R. equi* positive and no foal was presumed to be *S. zooepidemicus* positive. Twenty-two of the 30, 2010 non-vaccinated foals, 11 of the 30 2011 vaccinated foals, and one out of 31 2012 foals were administered antibiotics. All of the 2010 foals administered antibiotics where observed to have clinical symptoms of fever, lethargy, cough, nasal discharge, diarrhea, muscle tremors and/or dyspnea. Of the 30 2011 foals, only 11 exhibited clinical signs of disease including very mild cough, fever and/or lethargy. These clinical signs were very responsive to antibiotic treatment, which was continued for 5-51 days compared to the 2010 non-vaccinated foals in which duration of therapy lasted 17-187 days. The responsiveness of the 2011 foals to the antibiotic Naxcel and the mildness of the clinical signs indicated that the clinical signs were due to a *S. zooepidemicus* infection. Only one of the 2012 foals exhibited clinical signs of disease including severe and persistent cough, fever and lethargy. This foal was highly resistant to antibiotic therapy with treatment for 114 days and was diagnosed as *R. equi* positive. Two foals from the 2012 group were administered antibiotics for non-respiratory related illnesses (data not shown).

TABLE 11

Clinical evaluation of 2010 non-immunized foals born to non-immunized mares:

| 2010 Foal ID | Date of Birth (2010) | Age (in days) at Onset of Clinical Signs of Respiratory Illness | Clinical Signs of Respiratory Illness* | Antibiotics Administered in Response to Clinical Signs of Respiratory Illness** | Duration of Antibiotic Therapy (days) | Presumed Overall Assessment Based on Clinical Signs of Respiratory Illness and Response to Antibiotic Treatment |
|---|---|---|---|---|---|---|
| E-1001 | 1/8 | — | None | None | — | Healthy |
| E-1002 | 1/9 | — | None | None | — | Healthy |
| E-1003 | 1/12 | — | None | None | — | Healthy |
| E-1004 | 1/18 | 159 | F L C | Cla Rif | 102 | R. equi |
| E-1005 | 1/22 | 154 | None | Died | — | R. equi*** |

TABLE 11-continued

Clinical evaluation of 2010 non-immunized foals born to non-immunized mares:

| 2010 Foal ID | Date of Birth (2010) | Age (in days) at Onset of Clinical Signs of Respiratory Illness | Clinical Signs of Respiratory Illness* | Antibiotics Administered in Response to Clinical Signs of Respiratory Illness** | Duration of Antibiotic Therapy (days) | Presumed Overall Assessment Based on Clinical Signs of Respiratory Illness and Response to Antibiotic Treatment |
|---|---|---|---|---|---|---|
| E-1006 | 1/22 | 54 | F L C | Cla Dox Rif | 102 | *R. equi* |
| E-1007 | 1/22 | 77 | F L Dy | Dox Rif | 46 | *R. equi* |
| E-1008 | 2/1 | 71 | F L | Dox Rif | 101 | *R. equi* |
| E-1009 | 2/1 | 57 | F L C | Cla Dox Rif | 84 | *R. equi* |
| E-1010 | 2/2 | 125 | F N C L | Cla Rif Nax | 96 | *R. equi* and *S. zooepidemicus* |
| E-1011 | 2/2 | 185 | F L C | Cla Nax Rif | 82 | *R. equi* and *S. zooepidemicus* |
| E-1012 | 2/3 | 80 | F L C Dy | Cla Dox Rif | 182 | *R. equi* |
| E-1013 | 2/6 | 73 | F L C N | Cla Dox Rif | 135 | *R. equi* |
| E-1014 | 2/7 | 50 | F C D | Cla Nax Rif | 119 | *R. equi* and *S. zooepidemicus* |
| E-1015 | 2/10 | 65 | F L C D | Cla Dox Rif Met | 134 | *R. equi* and *S. zooepidemicus* |
| E-1016 | 2/15 | 71 | C Dy | Dox Rif | 17 | *R. equi* |
| E-1017 | 2/15 | 50 | F L D | Cla Dox Rif Met Nax | 158 | *R. equi* |
| E-1018 | 2/16 | — | None | None | — | Healthy |
| E-1019 | 2/16 | 150 | F L C D | Cla Nax Rif Met | 95 | *R. equi* |
| E-1020 | 2/20 | 107 | F C N | Cla Rif | 86 | *R. equi* and *S. zooepidemicus* |
| E-1021 | 2/23 | 54 | F L C N D | Cla Dox Nax Rif Met | 132 | *R. equi* and *S. zooepidemicus* |
| E-1022 | 3/3 | 118 | F L C M | Cla Nax Rif | 99 | *R. equi* |
| E-1023 | 3/2 | 146 | F L C N | Cla Nax Rif | 113 | *R. equi* and *S. zooepidemicus* |
| E-1024 | 3/13 | 118 | F L C N | Cla Nax Rif | 111 | *R. equi* and *S. zooepidemicus* |
| E-1025 | 3/14 | 114 | F L C N M | Cla Nax Rif | 113 | *R. equi* and *S. zooepidemicus* |
| E-1026 | 3/16 | 33 | F L C | Cla Dox Exc Rif | 111 | *R. equi* and *S. zooepidemicus* |
| E-1027 | 3/26 | — | None | None | — | Healthy |
| E-1028 | 4/13 | — | None | None | — | Healthy |
| E-1029 | 4/14 | 86 | F L C | Cla Rif | 88 | *R. equi* |
| E-1030 | 3/10 | — | None | None | — | Healthy |

All foals received colostrum from their dams within 24 hours of birth. All foals were intravenously administered 1 liter of USDA licensed commercial plasma from *R. equi* immunized plasma donor horses at 1 day and 21 days of age. Foals were observed for 200 days post foaling.
*Clinical Signs of Respiratory Illness are abbreviated as follows: C: Cough D: Diarrhea Dy: Dyspnea F: Fever L: Lethargy M: Muscle Tremors N: Nasal Discharge
**Antibiotics are abbreviated as follows: Cla: Clarithromycin Dox: Doxycycline Exc: Excede Met: Metronidazole Nax: Naxcel Rif: Rifampin
***Foal E-1005 was presumed positive for *R. equi* based on clinical signs of respiratory illness and necropsy findings.

TABLE 12

Clinical evaluation of 2011 VapC immunized foals born to VapC immunized mares:

| 2011 Foal ID | Date of Birth (2011) | Group | Date of Onset of Clinical Signs of Respiratory Illness | Age (in days) at Onset of Clinical Signs of Respiratory Illness | Clinical Signs of Respiratory Illness* | Antibiotics Administered in Response to Clinical Signs of Respiratory Illness** | Duration of Antibiotic Therapy (days) | Presumed Overall Assessment Based on Clinical Signs of Respiratory Illness and Response to Antibiotic Treatment |
|---|---|---|---|---|---|---|---|---|
| E-1101 | 1/3 | 3 | — | — | — | — | — | Healthy |
| E-1102 | 1/14 | 3 | 2/24 | 41 | F L | Cla Rif Nax | 51 | *S. zooepidemicus* |
| E-1103 | 1/24 | 3 | — | — | — | — | — | Healthy |
| E-1104 | 1/23 | 3 | — | — | — | — | — | Healthy |
| E-1105 | 1/19 | 3 | 5/13 | 114 | — | Nax | 5 | *S. zooepidemicus* |
| E-1106 | 1/27 | 3 | — | — | — | — | — | Healthy |
| E-1107 | 2/2 | 3 | — | — | — | — | — | Healthy |
| E-1108 | 1/19 | 3 | 4/28 | 100 | L C | Cla Rif Nax | 21 | *S. zooepidemicus* |
| E-1109 | 2/10 | 3 | 5/20 | 99 | F C | Nax | 5 | *S. zooepidemicus* |
| E-1110 | 2/10 | 3 | — | — | — | — | — | Healthy |
| E-1111 | 2/10 | 2 | 3/28 | 46 | L | Nax | 8 | *S. zooepidemicus* |
| E-1112 | 2/14 | 2 | — | — | — | — | — | Healthy |
| E-1113 | 2/19 | 1 | — | — | — | — | — | Healthy |
| E-1114 | 2/21 | 1 | — | — | — | — | — | Healthy |
| E-1115 | 2/24 | 1 | 4/28 | 63 | F N | Nax | 15 | *S. zooepidemicus* |
| E-1116 | 2/26 | 1 | — | — | — | — | — | Healthy |
| E-1117 | 2/27 | 1 | — | — | — | — | — | Healthy |
| E-1118 | 2/27 | 1 | — | — | — | — | — | Healthy |
| E-1119 | 2/28 | 1 | — | — | — | — | — | Healthy |
| E-1120 | 3/4 | 1 | — | — | — | — | — | Healthy |
| E-1121 | 3/7 | 1 | — | — | — | — | — | Healthy |
| E-1122 | 3/10 | 1 | 4/8 | 29 | L | Nax | 6 | *S. zooepidemicus* |
| E-1123 | 3/14 | 1 | — | — | — | — | — | Healthy |
| E-1124 | 3/14 | 1 | 4/28 | 45 | L | — | 8 | Healthy |
| E-1125 | 3/19 | 1 | — | — | — | — | — | Healthy |
| E-1126 | 3/20 | 1 | — | — | — | — | — | Healthy |
| E-1127 | 3/26 | 1 | — | — | — | — | — | Healthy |

TABLE 12-continued

Clinical evaluation of 2011 VapC immunized foals born to VapC immunized mares:

| 2011 Foal ID | Date of Birth (2011) | Group | Date of Onset of Clinical Signs of Respiratory Illness | Age (in days) at Onset of Clinical Signs of Respiratory Illness | Clinical Signs of Respiratory Illness* | Antibiotics Administered in Response to Clinical Signs of Respiratory Illness** | Duration of Antibiotic Therapy (days) | Presumed Overall Assessment Based on Clinical Signs of Respiratory Illness and Response to Antibiotic Treatment |
|---|---|---|---|---|---|---|---|---|
| E-1128 | 4/2 | 1 | 5/3 | 31 | L | Nax | 7 | *S. zooepidemicus* |
| E-1129 | 4/21 | 1 | 5/20 | 29 | — | Nax*** | 5 | Healthy |
| E-1130 | 4/28 | 1 | 6/9 | 42 | L | Nax | 5 | *S. zooepidemicus* |

All foals received colostrum from their VapC immunized dams within 24 hours of birth. All foals were intravenously administered 1 liter of plasma from VapC immunized plasma donor horses at 1 day of age. Foals were observed for 200 days post foaling. Foals were immunized with VapC vaccine at approximately approximately 2, 6, 10, and 14 weeks old in group 1, approximately 3, 7, 11 and 15 weeks old in group 2 and approximately 4, 6, 10, and 14 weeks old in group 3. See Table 6B for individual VapC protein antibody titers and Table 6 for average VapC protein antibody titers.

*Clinical Signs of Respiratory Illness are abbreviated as follows:

C: Cough

F: Fever

L: Lethargy

N: Nasal Discharge

**Antibiotics are abbreviated as follows:

Cla: Clarithromycin

Nax: Naxcel

Rif: Rifampin

***Foal E-1129 was treated with Naxcel in response to umbillical swelling.

TABLE 13

Clinical evaluation of 2012 VapA, VapC and VapA/VapC immunized foals born to VapA, VapC and VapA/VapC immunized mares:

| 2012 Foal ID | Date of Birth (2012) | Group | Immunogen used to vaccinate mares and their foals | Date of Onset of Clinical Signs of Respiratory Illness | Age (in days) at Onset of Clinical Signs of Respiratory Illness | Clinical Signs of Respiratory Illness* | Antibiotics Administered in Response to Clinical Signs of Respiratory Illness** | Duration of Antibiotic Therapy (days) | Presumed Overall Assessment Based on Clinical Signs of Respiratory Illness and Response to Antibiotic Treatment |
|---|---|---|---|---|---|---|---|---|---|
| E-1201 | 39467 | 6 | VapA/VapC | — | — | — | — | — | Healthy |
| E-1202 | 39472 | 4 | VapA | — | — | — | — | — | Healthy |
| E-1203 | 39474 | 5 | VapC | — | — | — | — | — | Healthy |
| E-1204 | 39475 | 4 | VapA | — | — | — | — | — | Healthy |
| E-1205 | 39477 | 5 | VapC | — | — | — | — | — | Healthy |
| E-1206 | 39480 | 6 | VapA/VapC | — | — | — | — | — | Healthy |
| E-1207 | 39481 | 6 | VapA/VapC | — | — | — | — | — | Healthy |
| E-1208 | 39483 | 6 | VapA/VapC | — | — | — | — | — | Healthy |
| E-1209 | 39484 | 5 | VapC | — | — | — | — | — | Healthy |
| E-1210 | 39484 | 5 | VapC | — | — | — | — | — | Healthy |
| E-1211 | 39486 | 4 | VapA | — | — | — | — | — | Healthy |
| E-1212 | 39493 | 5 | VapC | — | — | — | — | — | Healthy |
| E-1213 | 39497 | 6 | VapA/VapC | — | — | — | — | — | Healthy |
| E-1214 | 39499 | 5 | VapC | — | — | — | — | — | Healthy |
| E-1215 | 39499 | 4 | VapA | — | — | — | — | — | Healthy |
| E-1217 | 39504 | 4 | VapA | — | — | — | — | — | Healthy |
| E-1218 | 39506 | 4 | VapA | — | — | — | — | — | Healthy |
| E-1219 | 39509 | 6 | VapA/VapC | — | — | — | — | — | Healthy |
| E-1220 | 39511 | 4 | VapA | — | — | — | — | — | Healthy |
| E-1221 | 39512 | 4 | VapA | 39579 | 67 | F C L N | Azi Rif Met Cla Ven | 128 | *R. equi**** |
| E-1222 | 39513 | 4 | VapA | — | — | — | — | — | Healthy |
| E-1223 | 39514 | 4 | VapA | — | — | — | — | — | Healthy |
| E-1224 | 39516 | 4 | VapA | — | — | — | — | — | Healthy |
| E-1225 | 39518 | 5 | VapC | — | — | — | — | — | Healthy |
| E-1226 | 39522 | 5 | VapC | — | — | — | — | — | Healthy |
| E-1227 | 39525 | 6 | VapA/VapC | — | — | — | — | — | Healthy |
| E-1228 | 39527 | 6 | VapA/VapC | — | — | — | — | — | Healthy |
| E-1229 | 39531 | 5 | VapC | — | — | — | — | — | Healthy |

TABLE 13-continued

Clinical evaluation of 2012 VapA, VapC and VapA/VapC immunized foals born to VapA, VapC and VapA/VapC immunized mares:

| 2012 Foal ID | Date of Birth (2012) | Group | Immunogen used to vaccinate mares and their foals | Date of Onset of Clinical Signs of Respiratory Illness | Age (in days) at Onset of Clinical Signs of Respiratory Illness | Clinical Signs of Respiratory Illness* | Antibiotics Administered in Response to Clinical Signs of Respiratory Illness** | Duration of Antibiotic Therapy (days) | Presumed Overall Assessment Based on Clinical Signs of Respiratory Illness and Response to Antibiotic Treatment |
|---|---|---|---|---|---|---|---|---|---|
| E-1230 | 39533 | 6 | VapA/VapC | — | — | — | — | — | Healthy |
| E-1231 | 39535 | 5 | VapC | — | — | — | — | — | Healthy |
| E-1232 | 39543 | 6 | VapA/VapC | — | — | — | — | — | Healthy |

All foals received colostrum from their dams within 24 hours of birth. All foals were intravenously administered 1 liter of plasma from VapA, VapC and VapA/VapC immunized donor horses, respectively, at 1 day of age. Foals were immunized with VapA (group 4), VapC (group 5) or VapA/VapC (group 6) vaccine at 6, 8, 12 and 16 weeks old. Foals were observed for 200 days post foaling. See Table 7B for individual Vap protein antibody titers and Table 7 for average Vap protein antibody titers.
*Clinical Signs of Respiratory Illness are abbreviated as follows: C: Cough F: Fever L: Lethargy N: Nasal Discharge
**Antibiotics are abbreviated as follows: Azi: Azithromycin Cla: Clarithromycin Met: Metronidazole Rif: Rifampin Ven: Ventipulmin
***Foal E-1221 was confirmed positive for R. equi by PCR In 2011 and 2012 all but one of the VapA, VapC, or VapAVapC vaccinated foals that also received REHIP were protected against an R. equi infection in comparison to the non-vaccinated foals of 2010 that only received commercial plasma. Out of the three foal groups (2010, 2011, and 2012) the highest number of presumed R. equi positive cases was noted in the non-vaccinated foals of 2010. In addition, all of the 22 presumed R. equi positive 2010 foals and the single presumed R. equi positive 2012 foal were poorly responsive to antibiotic treatment and exhibited severe respiratory clinical signs for extended periods of time. In 2010 one foal died from an R. equi infection. None of the VapC vaccinated foals of 2011 or VapC, or VapAVapC vaccinated foals of 2012 were presumed to have an R. equi infection. The only foal to have an R. equi infection in 2012 was a foal vaccinated with VapA only vaccine.

Foal Abscesses

Foal abscesses found in 2012 vaccinated foals were measured to determine size of abscess (Table 14). Three small, transient lung abscesses and one large lung abscess were observed in foals immunized with VapC only. However, none of these foals showed any other signs of clinical respiratory illness and therefore all VapC immunized foals were presumed healthy. Six small, transient lung abscesses and three slightly larger lung abscesses were observed in foals immunized with VapA only. All of these abscesses were transient and none progressed into any signs of R. equi disease symptoms. One foal showed other clinical signs of respiratory illness, including fever, cough, lethargy and nasal discharge. Fecal PCR tested positive for R. equi and therefore the foal was determined to be clinically ill due to an R. equi infection. The rest of the foals showed no other signs of clinical respiratory illness and were therefore presumed healthy. Nine small, transient lung abscesses were observed in foals immunized with VapAVapC. However, none of these foals showed any other signs of clinical respiratory illness and therefore all VapAVapC immunized foals were presumed healthy. In 2011, none of the ???? symptomatic foals were ???? by ultrasound for lung abscesses while in the 2010 foal group, all 23 of the foals diagnosed as R. equi positive had multiple large abscesses that were highly resistant to antibiotic therapy. However, the only foals in this group that were screened for abscesses were those that exhibited respiratory clinical signs.

TABLE 14

Comparison of number, size and duration of detection of lung abscesses in VapA, VapC and VapA/VapC immunized 2012 foals born to VapA, VapC and VapA/VapC immunized mares:

| | Number of abscess detected for one week or less | Number of abscess detected for one to two weeks | Number of abscess detected for more than two weeks |
|---|---|---|---|
| VapA immunized foals: | | | |
| Number of abcesses <1 cm | 6 | 0 | 0 |
| Number of abcesses 1-3 cm | 7 | 2 | 2 |
| VapC immunized foals: | | | |
| Number of abcesses <1 cm | 3 | 0 | 0 |
| Number of abcesses 1-3 cm | 1 | 1 | 1 |
| VapA/VapC immunized foals: | | | |
| Number of abcesses <1 cm | 9 | 0 | 0 |
| Number of abcesses 1-3 cm | 0 | 0 | 0 |

All foals received colostrum from their dams within 24 hours of birth.
All foals were intravenously administered 1 liter of plasma from VapA, VapC and VapA/VapC immunized donor horses, respectively, at 1 day of age.
Foals were immunized with VapA (group 4), Vap C (group 5) or VapA/VapC (group 6) vaccine at 6, 8, 12 and 16 weeks old.
Foals were evaluated by ultrasound at regular intervals (every 2 weeks) for 200 days post foaling.

VapC Peptides

Figure 2B:
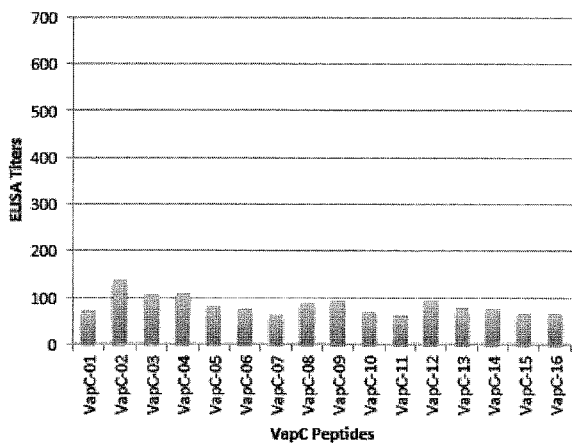

Synthesized VapC peptides were tested with an ELISA against donor test bleed samples from VapC vaccinated donors and commercial plasma to measure their titer concentrations (FIG. 2). The test bleed samples from VapC immunized donors show elevated ELISA antibody titers against in-house VapC peptide epitopes VapC-04 through VapC-06 and VapC-08, corresponding to the region on the VapC native protein between amino acids 34-70 and 78-93. There is little to no homology (0-25%) between VapA and VapC proteins at the amino acid regions 34-70 and 78-93, corresponding to VapC-04 through vapC-06 and VapC-08. The region considered most conserved between VapA and VapC protein is between amino acids 94-174, which correspond to the peptides VapC-10 through VapC-13. Vanniasinkam et al. in patent number U.S. Pat. No. 7,169,393 B2 described that the most immunological region of VapA corresponds to the VapA amino acid region 62-81, which has marginal homology to VapC at that same region. The averaged titers of commercial plasmas 1, 2, and 3 do not show elevated titers against any of the in-house synthesized VapC peptide epitopes compared to titers of plasma from VapC immunized donors (FIG. 2). Plasma antibody from VapC immunized donors was more effective in preventing respiratory illness in foals than the commercial plasma. This may suggest that the amino acid regions 34-70 and 78-93 of VapC are immunologically significant.

The low numbers of presumed R. equi positive foals from 2011 and 2012 in our results suggests that the combination of orally administered hyper-immunized colostrum and REHIP administration at 0-1 days after birth in addition to vaccination with VapA, VapC, or VapAVapC is important in protecting foals against an *R. equi* infection. Taken as a whole, our results suggest that antibodies raised against VapC recombinant protein provide protection against VapC and some protection against VapA recombinant proteins, and more specifically, provide protection against potentially immunologically significant VapC protein regions 34-70 and 78-93, which shows marginal to no homology to VapA protein. Antibodies raised against VapA recombinant protein provide very little to no protection against VapC recombinant protein, but provide additional protection against VapA, VapD, VapE, and VapG recombinant proteins. Therefore, antibodies raised against both VapA and VapC provide the most protection. The recombinant VapAVapC vaccine is a strong candidate for a commercial vaccine that helps foals combat *R. equi* infections and lead healthy lives.

REFERENCES

Becú, T. et al. *Vet. Microbiol.* 1997 Jun. 16; 56(3-4): 193-204.

Bell et al. *J. appl. Mircobiol.* 1998 August; 85(2): 195-210.

Benoit et al. *Infection and Immunity.* 2002 July; 70(7): 3768-3776.

Breathnach, C. C, et al. *Vet. Immunol. Immunopathol.* 2006 Aug. 15; 112(3-4): 199-209.

Byrne, B. A., et al. *Infect Immun.* 2001 February; 69(2): 650-6. Cauchard, J. et al. *Vet Microbiol.* 2004 Nov. 30; 104(1-2): 73-81.

Cauchard et al. *Int J Med Microbiol.* 2006 October; 296(6): 389-96.

Chirino-Trejo, J. M. et al. *Can. J. Vet. Res.* 1987 October; 51(4): 444-7.

Cohen, N. *Compendium: Equine Edition.* 2006; 14-18.

Coulson et al. *Infect and Immun.* 2010 August; 78(8): 3323-3334.

Dawson, T. R. et al. *Vet. Immunol. Immunopathol.* 2010 May 15; 135(1-2): 1-11.

Embley, T. M., et al. *Annu. Rev. Microbiol.* 1994; 48: 257-289.

Fernandez-Mora et al., *Traffic.* 2005 August; 6(8): 635-653.

Giguere et al. *Vet microbial.* 1997; 56: 313-34.

Giguere, S. *Infect. Immun.* 1999 July; 67(7): 3548-57.

Giguere et al. *Infect and Immun.* 1999 October; 67(10): 5041-5047.

Giguere, S. *J. Am. Vet. Med. Assoc.* 2002 Jan. 1; 220(1): 59-63.

Gürtler et al. *FEMS Microbiol Rev.* 2004 June; 28(3): 377-403.

Haas, A. *Traffic.* 2007 April; 8(4): 311-30.

Haghighi, H. R. and Prescott, J. F. *Vet. Immunol. Immunopathol.* 2005 Apr. 8; 104(3-4): 215-25.

Heuzenroeder, M. et al. *Methods MolBiol.* 2009; 524:137-44.

Higuchi et al. *Zentralbl Veterinarmed B.* 1999 November; 46(9): 641-648.

Hines and Hitela. *Equine Vet J.* 1996 September; 28(5): 339-340.

Holznagel et al. *Equine. Vet. J.* 2003 September; 35(6): 620-622.

Hondulas et al. *Infect Immun.* 1994 October; 62(10): 4167-4175.

Hooper-McGrevy et al. *Am J Vet Res.* 2001 August; 62(8): 1307-1313.

Hooper-McGrevy, K. E. et al. *Clin. Diagn. Lab Immunol.* 2003 May; 10(3): 345-51.

Hooper-McGrevy, K. E. et al. *Vaccine.* 2005 Dec. 30; 23(50): 5760-7.

Hurley, J. R. *Aust. Vet. J.* 1995 November; 72(11): 418-20.

Jacks, S. et al. *Clin. Vaccine Immunol.* 2007 April; 14(4): 369-374.

Jain, S. *Mol. Microbio.* 2003 October; 50(1): 115-28.

Letek et al. *J Bacterial.* 2008 September; 190(17): 5797-5805.

Letek, M. et al. *PLosS Genet.* 2010 Sep. 30; 6(9). pii: e1OO1 145.

Lewis, B. et al. *Mol. Immuno.* 2008 February; 45(3): 818-27.

Lopez, A. M. *Clin Diagn Lab Immunol.* 2002 November; 9(6): 1270-6.

Lopez et al. *Vaccine.* 2003 Sep. 8; 21(25-26): 3815-3825.

Lopez et al. *Vaccine.* 2008 Feb. 13; 26(7): 998-1009.

Lührmann, A. et al. *Infect. Immuno.* 2004 February; 72(2): 853-62.

Martens, R. J. et al. *Equine Vet J.* 1989 July; 21(4), 249-255.

Meijer and Prescott. *Vet Res.* 2004 July-August; 35(4): 383-396.

Muscatello, G. *Vet J.* 2012 April; 192(1): 20-6.

Muscatello, G. *Vet J.* 2012 April; 192(1): 27-33.

Muscatello, G. et al. *Equine Vet J.* 2007 September; 39(5): 470-8. Review.

Muscatello, G. et al. *J. Clin. Microbiol.* 2009 March; 47(3): 734-7.

Ocampo-Sosa, et al. *J. infect. Dis.* 2007 Sep. 1; 196(5):763-769.

Oldfield, C. et al. *Antonie Van Leeuwenkoek.* 2004 May; 85(4): 317-26.

Oliveira et al. *PLoS One.* 2010 Jan. 13; 5(1): e8644.

Pei, Y. et al. *Can J Vet Res.* 2007 January; 71(1): 1-7.

Pei et al. *Vet Microbiol.* 2007 Nov. 15; 125(1-2): 100-110.

Perkins, G. A. et al. *Vet. Ther.* 2002 Fall; 3(3): 334-46.

Prescott, J. F. *Clin Microbiol* Rev. 1991 January; 4(1): 20-34.

Rahman, M. T. et al. *Vet Microbiol.* 2003 Jul. 1; 94(2): 143-58.

Ren, J. and Prescott J. F. *Vet Microbiol.* 2003 Jul. 1; 94(2): 167-82.

Ren J. and Prescott J. F. *Vet Microbiol.* 2004 Nov. 15: 103(3-4): 219-230.

Russell, D. A. et al. *J. Bacterial.* 2004 September; 186(17): 5576-84.

Ryan, et al. *Vet. Immunol Immunopathol.* 2010 Jan. 15; 133(1), 66-71.

Sheoran, A. S. et al. *Am J Vet Res.* 2000 September; 61(9): 1099-1105.

Takai, S. et al. *J Clin. Microbiol.* 1991; 29: 439-443.

Takai, S. et al. *Infect. Immunol.* 1991 November; 59(11): 4056-60.

Takai, S. et al. *Infect Immun.* 1992 July; 60(7): 2995-2997.

Takai, S. et al. *J Clin Microbiol.* 1996 April; 34(4): 1034-7.

Takai, S. et al. *Microbiol. Immunol.* 1996; 40(8): 591-4.

Takai, S. et al. *Infect. Immun.* 2000 December; 68(12): 6840-7.

Takai, S. et al. *Vet Microbiol.* 2000 Sep. 15; 76(1): 71-80.

Tan, C. et al. *Can. J. Vet. Res.* 1995 January; 59(1): 51-9.

Taouji, S. et al. *Vaccine.* 2004 Mar. 12; 22(9-10): 1114-23.

Tkachuk-Sadd, O. and Prescott J. *J. Clin. Microbiol.* 1991 December; 29(12): 2696-700.

Toyooka, K. et al. *J. Med. Microbiol.* 2005 November; 54(Pt 11): 1007-15.

Vanniasinkam, T. *Vet. Immunol Immunopathol.* 2004 March; 98(1-2): 91-100.

Vanniasinkam, T. *Int. J. Med. Microbiol.* 2005 January; 294(7): 437-45.

Vanniasinkam, T. et al. "Antigenic Peptide Fragments of VapA Protein, and Uses Thereof" U.S. Pat. No. 7,169,393 B2.30, January, 2007.

Von Bargen, K. and Haas, A. *FEMS Microbiol. Rev.* 2009 September; 33(5): 870-91.

Von Bargen, K et al. *Infect Immun.* 2009 December; 77(12): 5676-5681.

Wagner, B. *Dev. Comp. Immunol* 2006; 30(1-2): 155-64. Review.

Wall, D. M., et al. *Infect Immun.* 2005 October; 73(10), 6736-6741.

Weinstock, D. M. and Brown, A. *Clin Infect Dis.* 2002 May 15; 34(10): 1379-85.

WHO, *HIV/AIDS Data and Statistics,* 2010 Zink, M. C. et al. *Vet. Microbiol.* 1987 August; 14(3): 295-305.

---

The invention claimed is:

1. An isolated recombinant protein consisting of:
   (a) consecutive amino acids 29-189 of *Rhodococcus equi* virulence-associated protein A (VapA), (i) the sequence of which is set forth in SEQ ID NO:1, or (ii) varies from such sequence by not more than five amino acids; or consecutive amino acids 29-173 of *Rhodococcus equi* virulence-associated protein (VapC), the sequence of which is set forth in SEQ ID NO:3, or (ii) varies from such sequence by not more than five amino acids,
   (b) consecutive amino acids which consist of a 6-His tag, a poly-6-His tag, or a glutathione S-transferase tag, and
   (c) a linker sequence between (a) and (b).

2. The isolated recombinant protein of claim 1, wherein the sequence of the isolated recombinant protein is the sequence set forth in SEQ ID NO: 18.

3. The isolated recombinant protein of claim 1, wherein the sequence of the isolated recombinant protein is the sequence set forth in SEQ ID NO: 19.

4. The isolated recombinant protein of claim 1, wherein the sequence of the isolated recombinant protein is the sequence set forth in SEQ ID NO: 20.

5. The isolated recombinant protein of claim 1, wherein the sequence of the isolated recombinant protein is the sequence set forth in SEQ ID NO: 21.

6. A composition comprising the isolated recombinant protein of claim 1 and a carrier.

7. The composition of claim 6, wherein the carrier is an aqueous or non-aqueous solution, suspension or emulsion and the recombinant protein is present in an amount of about 0.25 mg/ml to about 2.5 mg/ml.

8. The composition of claim 7, wherein the recombinant protein is present in an amount of about 0.5 mg/ml to about 1.5 mg/ml.

9. The composition of claim 8, wherein the recombinant protein is present in an amount of about 1 mg/ml.

10. The composition of claim 9, wherein the composition further comprises an adjuvant.

11. The composition of claim 10, wherein the adjuvant is present in an amount of 5-15% by volume.

12. The composition of claim 11, wherein the adjuvant is present in an amount of about 10% by volume.

13. The composition of claim 12 wherein the adjuvant is a carbomer-based adjuvant.

14. The composition of claim 6, wherein the carrier is an aqueous solution, and the composition has a pH between about 6.5 and about 7.5.

15. The composition of claim 14, wherein the pH is between about 6.7 and about 7.2.

16. A composition comprising:
   (a) an isolated recombinant protein comprising consecutive amino 29-189 of *Rhodococcus equi* virulence-associated protein A (VapA) (i) the sequence of which is set forth in SEQ ID NO:1, or (ii) varies from such sequence by not more than five amino acids;
   (b) an isolated recombinant protein comprising consecutive amino acids 29-173 of *Rhodococcus equi* virulence-associated protein (VapC) the sequence of which is set forth in SEQ ID NO:3, or (ii) varies from such sequence by not more than five amino acids; and
   (c) a carrier.

17. The composition of claim 16, wherein the carrier is an aqueous or non-aqueous solution, suspension or emulsion and wherein (a) and (b) are present in an amount which may be the same or different and is between about 0.25 mg/ml and about 2.5 mg/ml.

18. The composition of claim 17, wherein each of (a) and (b) is present in an amount between about 0.5 mg/ml and about 1.5 mg/ml.

19. The composition of claim 18, wherein each of (a) and (b) is present in an amount of about 1 mg/ml.

20. The composition of claim 16, wherein the composition further comprises an adjuvant.

21. The composition of claim 20, wherein the carrier is an aqueous or non-aqueous solution, suspension or emulsion and wherein the adjuvant is present in an amount of 5-15% by volume.

22. The composition of claim 21, wherein the adjuvant is present in an amount of about 10% by volume.

23. The composition of claim 20 wherein the adjuvant is a carbomer-based adjuvant.

24. The composition of claim 19, wherein the carrier is an aqueous solution, and wherein the composition has a pH between about 6.5 and about 7.5.

25. The composition of claim 24, wherein the pH is between about 6.7 and about 7.2.

* * * * *

SEQUENCE LISTING

```
<160> NUMBER OF SEQ ID NOS: 46

<210> SEQ ID NO 1
<211> LENGTH: 189
<212> TYPE: PRT
<213> ORGANISM: Rhodococcus equi

<400> SEQUENCE: 1

Met Lys Thr Leu His Lys Thr Val Ser Lys Ala Ile Ala Ala Thr Ala
1               5                   10                  15

Val Ala Ala Ala Ala Met Ile Pro Ala Gly Cys Ala Asn Ala Thr
            20                  25                  30

Val Leu Asp Ser Gly Ser Ser Ala Ile Leu Asn Ser Gly Ala Gly
        35                  40                  45

Ser Gly Ile Val Gly Ser Gly Ser Tyr Asp Ser Ser Thr Thr Ser Leu
    50                  55                  60

Asn Leu Gln Lys Asp Glu Pro Asn Gly Arg Ala Ser Asp Thr Ala Gly
65                  70                  75                  80

Gln Glu Gln Gln Tyr Asp Val His Gly Asp Val Ile Ser Ala Val Val
                85                  90                  95

Tyr Gln Arg Phe His Val Phe Gly Pro Glu Gly Lys Val Phe Asp Gly
                100                 105                 110

Asp Ala Gly Gly Leu Thr Leu Pro Gly Ala Gly Ala Phe Trp Gly Thr
            115                 120                 125

Leu Phe Thr Asn Asp Leu Gln Arg Leu Tyr Lys Asp Thr Val Ser Phe
        130                 135                 140

Gln Tyr Asn Ala Val Gly Pro Tyr Leu Asn Ile Asn Phe Phe Asp Ser
145                 150                 155                 160

Ser Gly Ser Phe Leu Gly His Ile Gln Ser Gly Val Ser Thr Val
                165                 170                 175

Val Gly Val Gly Gly Ser Gly Ser Trp His Asn Ala
            180                 185

<210> SEQ ID NO 2
<211> LENGTH: 197
<212> TYPE: PRT
<213> ORGANISM: Rhodococcus equi

<400> SEQUENCE: 2

Met Met Lys Ala Leu His Lys Thr Val Ser Arg Ala Ile Ala Ala Ile
1               5                   10                  15

Ala Thr Ala Ala Ala Ala Val Leu Ala Val Ala Pro Ala Ser Val Ala
            20                  25                  30
```

```
Asn Ala Ala Val Leu Asp Ser Gly Gly Ser Ala Leu Leu Lys Asp
             35                  40                  45

Gly Ala Gly Ser Gly Glu Val Gly Ser Gln Ala Tyr Asp Ser Ser Thr
 50                  55                  60

Val Ser Ser Asn Leu Gln Lys Ala Glu Thr Asn Gly Pro Val Gly Leu
 65                  70                  75                  80

Ala Gly Thr Ala Glu Gln Glu Gln Tyr Asp Val His Gly Asn Val
                 85                  90                  95

Ile Ser Ala Ala Val Tyr Gln Lys Phe His Val Tyr Gly Pro Glu Asp
                100                 105                 110

Met Val Phe Asp Gly Asp Ala Gly Gly Leu Thr Ile Pro Gly Ala Gly
                115                 120                 125

Ala Phe Trp Gly Thr Leu Phe Thr Ser Asp Leu Gln Arg Leu Tyr Lys
    130                 135                 140

Asp Thr Val Ser Phe Gln Tyr Asn Ala Leu Gly Thr Tyr Leu Asn Ile
145                 150                 155                 160

Asn Phe Phe Asp Ser Ser Gly Gly Phe Leu Gly His Ile Gln Ala Gly
                165                 170                 175

Ala Val Ser Ala Val Val Gly Val Gly Gly Ser Gly Ser Trp His
                180                 185                 190

Asn Trp Glu Val Ala
            195

<210> SEQ ID NO 3
<211> LENGTH: 173
<212> TYPE: PRT
<213> ORGANISM: Rhodococcus equi

<400> SEQUENCE: 3

Met Phe Arg Val Gly Arg Pro Ser Lys Ser Ile Ala Val Val Ala Ser
  1               5                  10                  15

Val Leu Cys Phe Leu Ala Leu Gly Gly Thr Ala Arg Ala Asn Val Val
                 20                  25                  30

Ala Pro Ser Ala Trp Gly Gly Ala Gln Ser Ala Ala Asp Lys Glu Gly
             35                  40                  45

Glu Gly Val Thr Leu Gly Gly Val Gly Val Leu Arg Pro His Asn Lys
 50                  55                  60

Asp Ala Asp Glu Gln Tyr Val His Gly Val Val Ser Ala Leu Phe
 65                  70                  75                  80

Tyr Asn His Leu Arg Ile Ser Val Asp Gly Met Thr Phe Asp Gly
                 85                  90                  95

Asp Gly Gly Gly Leu Ser Thr Pro Gly Gly Gly Ala Leu Trp Gly Thr
                100                 105                 110

Leu Thr Thr Ser Asp Leu Gln Gln Leu Tyr Asp Glu Thr Ala Ser Phe
            115                 120                 125

Glu Cys Asn Ala Val Gly Pro Tyr Leu Asn Ile Asn Phe Tyr Asp Ser
    130                 135                 140

Tyr Gly Arg Ile Leu Ala Ser Val Gln Ala Gly Gly Val Ser Thr Met
145                 150                 155                 160

Ile Gly Ile Gly Gly Gly Asn Gly Arg Trp His Leu Val
                165                 170

<210> SEQ ID NO 4
<211> LENGTH: 164
<212> TYPE: PRT
<213> ORGANISM: Rhodococcus equi
```

<400> SEQUENCE: 4

```
Met Val Arg Ala Arg Ala Phe Gly Arg Leu Phe Thr Phe Leu Leu Ala
1               5                   10                  15
Val Ala Val Ile Ala Thr Val Ser Met Gly Gly Ala Asn Ala Gln Glu
            20                  25                  30
Leu Ala Gly Thr Lys Thr Ser Asp Ala Ala Leu Leu Ser Gly Asn Lys
        35                  40                  45
Ala Ala Ile Pro Glu Asp Lys Glu Tyr Asp Val Ser Gly Arg Val Val
    50                  55                  60
Ser Ala Leu Val Tyr Gln Tyr Phe Ile Val Thr Val Asp Asp Ala Glu
65                  70                  75                  80
Asp Lys Lys Gly Lys Thr Phe Gln Gly Asp Ala Gly Gly Val Thr Ile
                85                  90                  95
Pro Gly Val Asp Phe Phe Trp Gly Thr Leu His Thr Pro Asp Leu Glu
            100                 105                 110
Lys Leu Tyr Ser Asp Thr Val Ser Phe Gln Tyr Asn Ala Ala Ala Thr
        115                 120                 125
Phe Leu Asn Ile Asn Phe Phe Asp Ser Lys Gly Glu Arg Leu Gly Tyr
    130                 135                 140
Val Leu Ala Gly Ala Ala Gly Thr Val Ser Gly Ile Gly Gly Gly Thr
145                 150                 155                 160
Gly Gly Trp Glu
```

<210> SEQ ID NO 5
<211> LENGTH: 206
<212> TYPE: PRT
<213> ORGANISM: Rhodococcus equi

<400> SEQUENCE: 5

```
Met Thr Thr Val His Lys Lys Ala Ser Lys Ile Ala Phe Thr Val
1               5                   10                  15
Ala Leu Arg Leu Pro Phe Ala Gly Thr Ala Val Ala Leu Val Leu Ile
            20                  25                  30
Ala Leu Thr Ile Val Ala Ala Pro Thr Gly Ile Ala Gly Ala Arg Glu
        35                  40                  45
Ile Gly Ala Gln Ala Trp Pro Ala Ser Gln Leu Glu Ser Gly Leu Ala
    50                  55                  60
Val Ser Gly Asn Pro Val Gly Val His Asp Val Arg Met Ala Val His
65                  70                  75                  80
Asp Asp Ser Thr His Thr Arg Glu Phe Lys Glu Asp Ser Glu Lys
                85                  90                  95
Gln Tyr Pro Val His Gly Phe Ala Ser Ser Phe Ile Phe Tyr Gln Thr
            100                 105                 110
Val Ser Ile Ile Ile Asp Asp Asp Gly Arg Gly Gly Pro Gly Lys Thr
        115                 120                 125
Phe Glu Gly Glu Ala Gly Gly Ile Thr Thr Pro Gly Ala Ala Gly Tyr
    130                 135                 140
Ala Gly Val Leu Phe Thr Ser Asp Leu Glu Arg Leu Tyr Arg Glu Thr
145                 150                 155                 160
Val Ser Phe Glu Tyr Asn Ala Val Gly Pro Tyr Leu Asn Ile Asn Leu
                165                 170                 175
Phe Ala Gly Asp Gly Gly Leu Leu Gly His Val Gln Ser Gly Ala Ile
            180                 185                 190
```

```
Ser Ser Leu Val Gly Ile Gly Gly Thr Gly Ala Trp Arg
        195                 200                 205

<210> SEQ ID NO 6
<211> LENGTH: 150
<212> TYPE: PRT
<213> ORGANISM: Rhodococcus equi

<400> SEQUENCE: 6

Met Ile Glu Tyr Ala Trp Tyr Gly Pro Ser Ile Gln Ser Asn Arg Cys
1               5                   10                  15

Cys Gly Asp Cys Pro Ile Leu Ala Leu Gly Gly His Arg Thr Cys
            20                  25                  30

Arg Leu Ala Thr Pro Ser Ala Trp Val Gly Thr Pro Ser Ala Ala Gly
        35                  40                  45

Lys Val Leu Pro Pro Ile Asn Asn Asn Ala Asp Glu Gln Tyr Ala Val
    50                  55                  60

His Gly Val Val Phe Ser Ala Val Phe Tyr Asn His Val Arg Ile Ser
65                  70                  75                  80

Val Asp Gly Gly Met Thr Phe Asp Gly Glu Gly Gly Leu Ser Thr
                85                  90                  95

Pro Gly Gly Gly Ala Leu Trp Gly Asn Leu Met Thr Ser Asp Leu Leu
                100                 105                 110

Cys Ser Tyr Thr Thr Lys Leu Arg Arg Ser Asn Val Ile Trp Pro
            115                 120                 125

Val Ser Lys Asp Gln Leu Leu Arg Gln Leu Trp Trp His Ser Trp Glu
    130                 135                 140

Cys Ser Arg Glu Arg Cys
145                 150

<210> SEQ ID NO 7
<211> LENGTH: 172
<212> TYPE: PRT
<213> ORGANISM: Rhodococcus equi

<400> SEQUENCE: 7

Met Ser Val Arg Thr Leu Leu Ala Ala Thr Leu Val Ala Gly Ile Ser
1               5                   10                  15

Val Leu Ala Pro Ala Gly Ile Ala Asn Ala Glu Thr Ser Met Val Ser
            20                  25                  30

Thr Thr Ala Ala Ser Ser Val Glu His Ala Ala Asn Thr Tyr Asp Phe
        35                  40                  45

Ala Glu Ala Lys Ser Gly Ser Ser Ile Pro Ala Lys Val Ala Ala Glu
    50                  55                  60

Gln Ala Asn Ser Tyr Ser Val His Gly Leu Val Thr Ser Leu Ala Val
65                  70                  75                  80

Tyr Gln His Phe Ser Leu Thr Val Glu Gly Gly Lys Thr Phe Thr
                85                  90                  95

Gly Asp Ser Gly Gly Ile Ser Ile Pro Gly Val Ala Val Leu Glu Gly
                100                 105                 110

Thr Leu Phe Thr Glu Asp Leu Gln His Leu Tyr Ser Asp Thr Val Ser
            115                 120                 125

Phe Glu Tyr Asn Ala Val Gly Pro Tyr Leu Asn Ile Asn Phe Phe Asp
    130                 135                 140

Ser His Gly Thr Leu Leu Gly His Val Gln Ser Gly Ser Ile Gly Thr
145                 150                 155                 160
```

Val Ser Gly Ile Gly Gly Gly Thr Gly Gly Trp Gln
              165                 170

<210> SEQ ID NO 8
<211> LENGTH: 187
<212> TYPE: PRT
<213> ORGANISM: Rhodococcus equi

<400> SEQUENCE: 8

Met Asn Leu Ser Lys Thr Thr Arg Lys Phe Leu Ser Arg Thr Ala Val
1               5                   10                  15

Pro Ala Thr Phe Val Met Ala Leu Thr Val Pro Trp Gly Cys Ala Ala
                20                  25                  30

Pro Pro Pro Leu Pro Asp Gly Pro Thr His Asp Leu Pro Thr Trp Arg
            35                  40                  45

Glu Glu Gly Ala Asn Tyr Ser Asp Gly Thr Met Leu Val Arg Ala Ser
        50                  55                  60

Ser Asn Phe Leu Glu Pro Ser Thr His Ser Asp Ser Gly Gln Gln Gln
65                  70                  75                  80

Trp Thr Val Gln Gly Val Leu Ala Ser Ala Leu Val Tyr Gln Arg Leu
                85                  90                  95

Lys Leu Asn Val Glu Gly Gly Glu Thr Phe Glu Gly Tyr Ala Gly Gly
            100                 105                 110

Leu Ser Phe Pro Gly Gly Ala Met Val Trp Gly Thr Leu Phe Thr Asp
        115                 120                 125

Asn Ile Gln Arg Leu Tyr Asp Arg Thr Glu Ser Phe Glu Phe Asn Ala
    130                 135                 140

Val Gly Pro Tyr Leu Asn Val Asn Phe Phe Asp Gly His Ser Ala Ile
145                 150                 155                 160

Leu Gly His Ala Gln Leu Gly Gly Val Ser Ser Val Ile Gly Ile Gly
                165                 170                 175

Gly Gly Thr Gly Thr Trp Ile Gly Asp Val Ala
            180                 185

<210> SEQ ID NO 9
<211> LENGTH: 80
<212> TYPE: PRT
<213> ORGANISM: Rhodococcus equi

<400> SEQUENCE: 9

Met Pro Ile Ala Leu Thr Ala Val Ala Leu Pro Ala Gly Met Ala Ser
1               5                   10                  15

Ala Gln Glu Met Gly Asp His Ala Trp Ser Gly Ser Arg Ala Glu Ser
                20                  25                  30

Asp Val Ala Val Leu Gly Lys Ala Glu Ser Ala His Asp Asp Pro Ser
            35                  40                  45

Leu Arg Thr Pro Lys Leu Lys Lys Ser Asn Ser Gly Asn Gln Tyr Arg
        50                  55                  60

Tyr Thr Val Leu Leu Ser Ser Phe Ile Phe Tyr Gln Thr Leu Ser Ile
65                  70                  75                  80

<210> SEQ ID NO 10
<211> LENGTH: 183
<212> TYPE: PRT
<213> ORGANISM: Rhodococcus equi

<400> SEQUENCE: 10

Met Asn Leu Ala His Val Thr Arg Lys Phe Leu Val Ser Thr Ala Val

```
1               5                   10                  15
Pro Val Thr Leu Val Ile Ala Phe Ala Ala Pro Phe Gln Phe Ser Ala
            20                  25                  30

Pro Leu Ala Ser Ala Ala Thr Ser Asp Leu Ser Ile Arg Arg Asp Gly
            35                  40                  45

Ser Ala His Tyr Ser Asp Ser Thr Leu Ser Leu Arg Ala Ser Ser Asp
            50                  55                  60

Ser Pro Glu Pro Thr Thr His Gly Ala Gln Gln Trp Ala Val His
65                  70                  75                  80

Gly Val Leu Ala Ser Ala Leu Val Tyr Gln Leu Leu Thr Leu Thr Val
                85                  90                  95

Asp Gly Gly Glu Gln Phe Gln Gly Tyr Ala Gly Gly Val Ser Phe Pro
                100                 105                 110

Gly Gly Ala Ala Val Trp Gly Thr Leu Phe Thr Asp Asp Ile Gln Arg
                115                 120                 125

Leu Tyr Asp Gln Thr Ala Ser Phe Gln Phe Asn Ala Val Gly Pro Tyr
            130                 135                 140

Leu Asn Val Asn Phe Phe Asp Arg His Gly Thr Leu Leu Gly His Ala
145                 150                 155                 160

Gln Leu Gly Gly Val Ser Ser Val Ile Gly Ile Gly Gly Ser Gly
                165                 170                 175

Thr Trp Thr Gly Asp Val Ala
            180

<210> SEQ ID NO 11
<211> LENGTH: 202
<212> TYPE: PRT
<213> ORGANISM: Rhodococcus equi

<400> SEQUENCE: 11

Met Gly Asn Ala Arg Arg Ser Trp Val Lys Ala Ala Ala Ala Thr
1               5                   10                  15

Leu Thr Ala Ala Ala Val Met Val Pro Ala Gly Leu Ala Asn Ala Gln
            20                  25                  30

Pro Leu Asp Val Gly Ser Ser Thr Val Val Ala Asn Asp Ala Phe
            35                  40                  45

Gly Ser Val Ser Leu Gly Gly His Gly Ser Ser Gly Tyr Gly Ser Ser
            50                  55                  60

Ser Asp Tyr Gly Ser Ser Ser Asp Tyr Asp Gly Ser Gly Ser Gly Phe
65                  70                  75                  80

Gly Thr Ala Pro Asp Val Arg Ser Gln Val Ala Ala Ser Leu Asp Glu
                85                  90                  95

Glu Gln Gln Tyr Asp Val Lys Gly Asp Val Trp Ser Ala Leu Val Tyr
                100                 105                 110

Gln Gln Phe His Val Glu Gly Pro Gln Gly Lys Val Phe Asp Gly Gln
                115                 120                 125

Ala Gly Gly Leu Thr Ile Pro Gly Ala Gly Ala Phe Trp Gly Thr Leu
            130                 135                 140

Phe Thr Ser Asp Leu Asn Arg Leu Tyr Ala Asp Thr Ser Ser Phe Gln
145                 150                 155                 160

Tyr Asn Ala Val Gly Pro Tyr Leu Asn Ile Asn Phe Phe Asp Gly Asn
                165                 170                 175

Gly Val Leu Leu Gly His Ile Gln Ala Gly Ala Val Ser Thr Val Thr
                180                 185                 190
```

```
Gly Val Gly Gly Gly Thr Gly Ser Trp Ser
        195                 200
```

<210> SEQ ID NO 12
<211> LENGTH: 202
<212> TYPE: PRT
<213> ORGANISM: Rhodococcus equi

<400> SEQUENCE: 12

```
Met Gly Asn Ala Arg Arg Ser Trp Val Lys Ala Ala Ala Ala Ala Thr
1               5                   10                  15

Leu Thr Ala Ala Ala Val Met Val Pro Ala Gly Leu Ala Asn Ala Gln
            20                  25                  30

Pro Leu Asp Val Gly Gly Ser Ser Thr Val Val Ala Asn Asp Ala Phe
        35                  40                  45

Gly Ser Val Ser Leu Gly Gly His Gly Ser Ser Asp Tyr Gly Ser Ser
    50                  55                  60

Ser Asp Tyr Gly Ser Ser Asp Tyr Asp Gly Ser Gly Ser Gly Phe
65                  70                  75                  80

Gly Thr Ala Pro Asp Val Arg Ser Gln Val Ala Ala Ser Leu Asp Glu
                85                  90                  95

Glu Gln Gln Tyr Asp Val Lys Gly Asp Val Trp Ser Ala Leu Val Tyr
            100                 105                 110

Gln Gln Phe His Val Glu Gly Pro Gln Gly Lys Val Phe Asp Gly Gln
        115                 120                 125

Ala Gly Gly Leu Thr Ile Pro Gly Ala Gly Ala Phe Trp Gly Thr Leu
    130                 135                 140

Phe Thr Ser Asp Leu Asn Arg Leu Tyr Ala Asp Thr Ser Ser Phe Gln
145                 150                 155                 160

Tyr Asn Ala Val Gly Pro Tyr Leu Asn Ile Asn Phe Phe Asp Gly Asn
                165                 170                 175

Gly Val Leu Leu Gly His Ile Gln Ala Gly Ala Val Ser Thr Val Thr
            180                 185                 190

Gly Val Gly Gly Gly Thr Gly Ser Trp Ser
        195                 200
```

<210> SEQ ID NO 13
<211> LENGTH: 189
<212> TYPE: PRT
<213> ORGANISM: Rhodococcus equi

<400> SEQUENCE: 13

```
Met Arg Pro Gln Ser Ser Tyr Arg Pro Tyr Val Arg Ala Ile Phe Ala
1               5                   10                  15

Ala Ala Leu Val Ala Gly Ile Ser Ile Leu Gly Ala Thr Gly Val Val
            20                  25                  30

Asn Ala Glu Thr Ser Met Ala Ser Asn Ala Ala Thr Ser Thr Val His
        35                  40                  45

Arg Val Ala Lys Thr Cys Asp Ser Asn Leu Ser Glu Asn Asp His Ser
    50                  55                  60

Ser Ala Glu Thr Asn Gly Gln Leu Ser Phe Ala Thr Glu Ala Thr Ala
65                  70                  75                  80

Glu Gln Gly Tyr Thr Tyr Ser Val His Gly Leu Val Thr Ser Leu Ala
                85                  90                  95

Val Tyr Gln His Phe Ser Leu Thr Val Glu Asp Asp Gly Lys Thr Phe
            100                 105                 110
```

```
Thr Gly Asp Ser Gly Gly Ile Ser Val Pro Gly Val Ala Val Leu Lys
            115                 120                 125

Gly Thr Leu Phe Thr Glu Asp Leu Gln Arg Leu Tyr Asn Asp Thr Val
130                 135                 140

Ser Phe Gln Tyr Asn Ala Val Gly Pro Tyr Met Asn Ile Asn Phe Phe
145                 150                 155                 160

Asp Ser His Ser Thr Leu Leu Gly His Val Gln Ser Gly Ser Ile Gly
                165                 170                 175

Thr Leu Thr Gly Ile Gly Gly Thr Gly Gly Trp Arg
            180                 185
```

<210> SEQ ID NO 14
<211> LENGTH: 177
<212> TYPE: PRT
<213> ORGANISM: Rhodococcus equi

<400> SEQUENCE: 14

```
Met Ile Arg Thr Val Val Gly Trp Gly Ala Phe Val Leu Ala Phe Ser
1               5                   10                  15

Ile Leu Ala Thr Gly Ala Ala Tyr Ala His Ala Gln Glu Leu Glu Pro
            20                  25                  30

Gly Gly Ser Phe Ser Glu Gly Ile Leu Gln Arg Asn Phe Pro Leu Glu
        35                  40                  45

Gly Glu Phe Ala Ser Val Ser Glu Pro Gly Ser Gly Asn Val Ser Ala
    50                  55                  60

Ser Lys Val Gly Glu Glu Ser Asn Phe Ala Val Arg Gly Val Val Val
65                  70                  75                  80

Ser Ala Leu Phe Tyr Gln His Leu Glu Ile Thr Val Ser Gly Gly Glu
                85                  90                  95

Thr Phe Asp Gly Asp Gly Gly Leu Ser Val Pro Gly Gly Ala
            100                 105                 110

Leu Trp Gly Thr Leu Phe Thr Arg Asp Leu Gln Arg Leu Tyr Asp Glu
        115                 120                 125

Thr Val Ser Phe Glu Phe Asn Ala Ala Gly Leu Phe Val Asn Val Asn
    130                 135                 140

Phe Phe Asp Lys Asp Gly Ile Leu Leu Gly His Val Glu Ser Gly Ala
145                 150                 155                 160

Val Ser Thr Ala Val Gly Ile Gly Gly Thr Gly Arg Trp His Ile
                165                 170                 175

Val
```

<210> SEQ ID NO 15
<211> LENGTH: 27
<212> TYPE: PRT
<213> ORGANISM: Rhodococcus equi

<400> SEQUENCE: 15

```
Arg Leu Tyr Asp Glu Thr Gly Pro Phe Asp Phe Asn Ala Ala Gly Leu
1               5                   10                  15

Phe Met Asn Val Asp His Phe Gly Tyr Arg Ala
            20                  25
```

<210> SEQ ID NO 16
<211> LENGTH: 160
<212> TYPE: PRT
<213> ORGANISM: Rhodococcus equi

<400> SEQUENCE: 16

```
Asn Ala Thr Val Leu Asp Ser Gly Ser Ser Ala Ile Leu Asn Ser
1               5                   10                  15

Gly Ala Gly Ser Gly Ile Val Gly Ser Gly Ser Tyr Asp Ser Ser Thr
                20                  25                  30

Thr Ser Leu Asn Leu Gln Lys Asp Glu Pro Asn Gly Arg Ala Ser Asp
            35                  40                  45

Thr Ala Gly Gln Glu Gln Gln Tyr Asp Val His Gly Asp Val Ile Ser
50                  55                  60

Ala Val Val Tyr Gln Arg Phe His Val Phe Gly Pro Glu Gly Lys Val
65                  70                  75                  80

Phe Asp Gly Asp Ala Gly Gly Leu Thr Leu Pro Gly Ala Gly Ala Phe
                85                  90                  95

Trp Gly Thr Leu Phe Thr Asn Asp Leu Gln Arg Leu Tyr Lys Asp Thr
                100                 105                 110

Val Ser Phe Gln Tyr Asn Ala Val Gly Pro Tyr Leu Asn Ile Asn Phe
            115                 120                 125

Phe Asp Ser Ser Gly Ser Phe Leu Gly His Ile Gln Ser Gly Gly Val
        130                 135                 140

Ser Thr Val Val Gly Val Gly Gly Ser Gly Ser Trp His Asn Ala
145                 150                 155                 160

<210> SEQ ID NO 17
<211> LENGTH: 145
<212> TYPE: PRT
<213> ORGANISM: Rhodococcus equi

<400> SEQUENCE: 17

Asn Val Val Ala Pro Ser Ala Trp Gly Gly Ala Gln Ser Ala Ala Asp
1               5                   10                  15

Lys Glu Gly Glu Gly Val Thr Leu Gly Gly Val Gly Val Leu Arg Pro
                20                  25                  30

His Asn Lys Asp Ala Asp Glu Gln Tyr Thr Val His Gly Val Val Val
            35                  40                  45

Ser Ala Leu Phe Tyr Asn His Leu Arg Ile Ser Val Asp Gly Gly Met
50                  55                  60

Thr Phe Asp Gly Asp Gly Gly Leu Ser Thr Pro Gly Gly Gly Ala
65                  70                  75                  80

Leu Trp Gly Thr Leu Thr Thr Ser Asp Leu Gln Gln Leu Tyr Asp Glu
                85                  90                  95

Thr Ala Ser Phe Glu Cys Asn Ala Val Gly Pro Tyr Leu Asn Ile Asn
                100                 105                 110

Phe Tyr Asp Ser Tyr Gly Arg Ile Leu Ala Ser Val Gln Ala Gly Gly
            115                 120                 125

Val Ser Thr Met Ile Gly Ile Gly Gly Gly Asn Gly Arg Trp His Leu
        130                 135                 140

Val
145

<210> SEQ ID NO 18
<211> LENGTH: 167
<212> TYPE: PRT
<213> ORGANISM: Rhodococcus equi
<220> FEATURE:
<221> NAME/KEY: DOMAIN
<222> LOCATION: (7)..(8)
<223> OTHER INFORMATION: Polylinker
```

<400> SEQUENCE: 18

His His His His His Xaa Asn Ala Thr Val Leu Asp Ser Gly Ser
1               5                   10                  15

Ser Ser Ala Ile Leu Asn Ser Gly Ala Gly Ser Gly Ile Val Gly Ser
            20                  25                  30

Gly Ser Tyr Asp Ser Ser Thr Thr Ser Leu Asn Leu Gln Lys Asp Glu
        35                  40                  45

Pro Asn Gly Arg Ala Ser Asp Thr Ala Gly Gln Glu Gln Gln Tyr Asp
    50                  55                  60

Val His Gly Asp Val Ile Ser Ala Val Val Tyr Gln Arg Phe His Val
65                  70                  75                  80

Phe Gly Pro Glu Gly Lys Val Phe Asp Gly Asp Ala Gly Gly Leu Thr
                85                  90                  95

Leu Pro Gly Ala Gly Ala Phe Trp Gly Thr Leu Phe Thr Asn Asp Leu
            100                 105                 110

Gln Arg Leu Tyr Lys Asp Thr Val Ser Phe Gln Tyr Asn Ala Val Gly
        115                 120                 125

Pro Tyr Leu Asn Ile Asn Phe Phe Asp Ser Ser Gly Ser Phe Leu Gly
    130                 135                 140

His Ile Gln Ser Gly Gly Val Ser Thr Val Val Gly Val Gly Gly Gly
145                 150                 155                 160

Ser Gly Ser Trp His Asn Ala
                165

<210> SEQ ID NO 19
<211> LENGTH: 379
<212> TYPE: PRT
<213> ORGANISM: Rhodococcus equi
<220> FEATURE:
<221> NAME/KEY: DOMAIN
<222> LOCATION: (219)..(220)
<223> OTHER INFORMATION: Polylinker

<400> SEQUENCE: 19

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

-continued

```
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
            195                 200                 205
Thr Phe Gly Gly Gly Asp His Pro Pro Lys Xaa Asn Ala Thr Val Leu
210                 215                 220
Asp Ser Gly Ser Ser Ala Ile Leu Asn Ser Gly Ala Gly Ser Gly
225                 230                 235                 240
Ile Val Gly Ser Gly Ser Tyr Asp Ser Ser Thr Ser Leu Asn Leu
                245                 250                 255
Gln Lys Asp Glu Pro Asn Gly Arg Ala Ser Asp Thr Ala Gly Gln Glu
            260                 265                 270
Gln Gln Tyr Asp Val His Gly Asp Val Ile Ser Ala Val Val Tyr Gln
        275                 280                 285
Arg Phe His Val Phe Gly Pro Glu Gly Lys Val Phe Asp Gly Asp Ala
290                 295                 300
Gly Gly Leu Thr Leu Pro Gly Ala Gly Ala Phe Trp Gly Thr Leu Phe
305                 310                 315                 320
Thr Asn Asp Leu Gln Arg Leu Tyr Lys Asp Thr Val Ser Phe Gln Tyr
                325                 330                 335
Asn Ala Val Gly Pro Tyr Leu Asn Ile Asn Phe Phe Asp Ser Ser Gly
            340                 345                 350
Ser Phe Leu Gly His Ile Gln Ser Gly Gly Val Ser Thr Val Val Gly
        355                 360                 365
Val Gly Gly Gly Ser Gly Ser Trp His Asn Ala
        370                 375

<210> SEQ ID NO 20
<211> LENGTH: 152
<212> TYPE: PRT
<213> ORGANISM: Rhodococcus equi
<220> FEATURE:
<221> NAME/KEY: DOMAIN
<222> LOCATION: (7)..(8)
<223> OTHER INFORMATION: Polylinker

<400> SEQUENCE: 20

His His His His His His Xaa Asn Val Val Ala Pro Ser Ala Trp Gly
1               5                   10                  15
Gly Ala Gln Ser Ala Ala Asp Lys Glu Gly Glu Gly Val Thr Leu Gly
            20                  25                  30
Gly Val Gly Val Leu Arg Pro His Asn Lys Asp Ala Asp Glu Gln Tyr
        35                  40                  45
Thr Val His Gly Val Val Ser Ala Leu Phe Tyr Asn His Leu Arg
    50                  55                  60
Ile Ser Val Asp Gly Gly Met Thr Phe Asp Gly Asp Gly Gly Leu
65                  70                  75                  80
Ser Thr Pro Gly Gly Gly Ala Leu Trp Gly Thr Leu Thr Thr Ser Asp
                85                  90                  95
Leu Gln Gln Leu Tyr Asp Glu Thr Ala Ser Phe Glu Cys Asn Ala Val
            100                 105                 110
Gly Pro Tyr Leu Asn Ile Asn Phe Tyr Asp Ser Tyr Gly Arg Ile Leu
        115                 120                 125
Ala Ser Val Gln Ala Gly Gly Val Ser Thr Met Ile Gly Ile Gly Gly
    130                 135                 140
```

Gly Asn Gly Arg Trp His Leu Val
145                 150

<210> SEQ ID NO 21
<211> LENGTH: 364
<212> TYPE: PRT
<213> ORGANISM: Rhodococcus equi
<220> FEATURE:
<221> NAME/KEY: DOMAIN
<222> LOCATION: (219)..(220)
<223> OTHER INFORMATION: Polylinker

<400> SEQUENCE: 21

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Xaa Asn Val Val Ala Pro
    210                 215                 220

Ser Ala Trp Gly Gly Ala Gln Ser Ala Ala Asp Lys Glu Gly Glu Gly
225                 230                 235                 240

Val Thr Leu Gly Gly Val Gly Val Leu Arg Pro His Asn Lys Asp Ala
                245                 250                 255

Asp Glu Gln Tyr Thr Val His Gly Val Val Ser Ala Leu Phe Tyr
            260                 265                 270

Asn His Leu Arg Ile Ser Val Asp Gly Met Thr Phe Asp Gly Asp
        275                 280                 285

Gly Gly Gly Leu Ser Thr Pro Gly Gly Ala Leu Trp Gly Thr Leu
    290                 295                 300

Thr Thr Ser Asp Leu Gln Gln Leu Tyr Asp Glu Thr Ala Ser Phe Glu
305                 310                 315                 320

Cys Asn Ala Val Gly Pro Tyr Leu Asn Ile Asn Phe Tyr Asp Ser Tyr
                325                 330                 335

Gly Arg Ile Leu Ala Ser Val Gln Ala Gly Gly Val Ser Thr Met Ile

```
                340                 345                 350
Gly Ile Gly Gly Gly Asn Gly Arg Trp His Leu Val
            355                 360
```

<210> SEQ ID NO 22
<211> LENGTH: 27
<212> TYPE: DNA
<213> ORGANISM: Rhodococcus equi

<400> SEQUENCE: 22
gccggatcca ctaatgcgac cgttctt                                       27

<210> SEQ ID NO 23
<211> LENGTH: 24
<212> TYPE: DNA
<213> ORGANISM: Rhodococcus equi

<400> SEQUENCE: 23
catgaattcc taggcgttgt gcca                                          24

<210> SEQ ID NO 24
<211> LENGTH: 29
<212> TYPE: DNA
<213> ORGANISM: Rhodococcus equi

<400> SEQUENCE: 24
gccggatccg ccaatgtagt cgctccgtc                                     29

<210> SEQ ID NO 25
<211> LENGTH: 29
<212> TYPE: DNA
<213> ORGANISM: Rhodococcus equi

<400> SEQUENCE: 25
catgaattcg cgagcgttta ccttccgac                                     29

<210> SEQ ID NO 26
<211> LENGTH: 22
<212> TYPE: DNA
<213> ORGANISM: Rhodococcus equi

<400> SEQUENCE: 26
gggctggcaa gccacgtttg gt                                            22

<210> SEQ ID NO 27
<211> LENGTH: 32
<212> TYPE: DNA
<213> ORGANISM: Rhodococcus equi

<400> SEQUENCE: 27
cgatggatcc ctaatgcgac cgttcttgat tc                                 32

<210> SEQ ID NO 28
<211> LENGTH: 383
<212> TYPE: PRT
<213> ORGANISM: Rhodococcus equi
<220> FEATURE:
<221> NAME/KEY: DOMAIN
<222> LOCATION: (219)..(220)
<223> OTHER INFORMATION: Polylinker

<400> SEQUENCE: 28

```
Met Ser Pro Ile Leu Gly Tyr Trp Lys Ile Lys Gly Leu Val Gln Pro
1               5                   10                  15
```

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Xaa Met Val Arg Ala Arg
    210                 215                 220

Ala Phe Gly Arg Leu Phe Thr Phe Leu Leu Ala Val Ala Val Ile Ala
225                 230                 235                 240

Thr Val Ser Met Gly Gly Ala Asn Ala Gln Glu Leu Ala Gly Thr Lys
                245                 250                 255

Thr Ser Asp Ala Ala Leu Leu Ser Gly Asn Lys Ala Ala Ile Pro Glu
        260                 265                 270

Asp Lys Glu Tyr Asp Val Ser Gly Arg Val Val Ser Ala Leu Val Tyr
    275                 280                 285

Gln Tyr Phe Ile Val Thr Val Asp Asp Ala Glu Asp Lys Lys Gly Lys
290                 295                 300

Thr Phe Gln Gly Asp Ala Gly Val Thr Ile Pro Gly Val Asp Phe
305                 310                 315                 320

Phe Trp Gly Thr Leu His Thr Pro Asp Leu Glu Lys Leu Tyr Ser Asp
            325                 330                 335

Thr Val Ser Phe Gln Tyr Asn Ala Ala Ala Thr Phe Leu Asn Ile Asn
        340                 345                 350

Phe Phe Asp Ser Lys Gly Glu Arg Leu Gly Tyr Val Leu Ala Gly Ala
    355                 360                 365

Ala Gly Thr Val Ser Gly Ile Gly Gly Thr Gly Gly Trp Glu
370                 375                 380

<210> SEQ ID NO 29
<211> LENGTH: 425
<212> TYPE: PRT
<213> ORGANISM: Rhodococcus equi
<220> FEATURE:
<221> NAME/KEY: DOMAIN
<222> LOCATION: (219)..(220)
<223> OTHER INFORMATION: Polylinker

<400> SEQUENCE: 29

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Xaa Met Thr Thr Val His
    210                 215                 220

Lys Lys Ala Ser Lys Ala Ile Ala Phe Thr Val Ala Leu Arg Leu Pro
225                 230                 235                 240

Phe Ala Gly Thr Ala Val Ala Leu Val Leu Ile Ala Leu Thr Ile Val
                245                 250                 255

Ala Ala Pro Thr Gly Ile Ala Gly Ala Arg Glu Ile Gly Ala Gln Ala
            260                 265                 270

Trp Pro Ala Ser Gln Leu Glu Ser Gly Leu Ala Val Ser Gly Asn Pro
        275                 280                 285

Val Gly Val His Asp Val Arg Met Ala Val His Asp Asp Ser Thr His
    290                 295                 300

Thr Arg Glu Phe Lys Glu Asp Asp Ser Glu Lys Gln Tyr Pro Val His
305                 310                 315                 320

Gly Phe Ala Ser Ser Phe Ile Phe Tyr Gln Thr Val Ser Ile Ile Ile
                325                 330                 335

Asp Asp Asp Gly Arg Gly Gly Pro Gly Lys Thr Phe Glu Gly Glu Ala
            340                 345                 350

Gly Gly Ile Thr Thr Pro Gly Ala Ala Gly Tyr Ala Gly Val Leu Phe
        355                 360                 365

Thr Ser Asp Leu Glu Arg Leu Tyr Arg Glu Thr Val Ser Phe Glu Tyr
    370                 375                 380

Asn Ala Val Gly Pro Tyr Leu Asn Ile Asn Leu Phe Ala Gly Asp Gly
385                 390                 395                 400

Gly Leu Leu Gly His Val Gln Ser Gly Ala Ile Ser Ser Leu Val Gly
```

```
                            405                 410                 415
Ile Gly Gly Gly Thr Gly Ala Trp Arg
            420                 425

<210> SEQ ID NO 30
<211> LENGTH: 391
<212> TYPE: PRT
<213> ORGANISM: Rhodococcus equi
<220> FEATURE:
<221> NAME/KEY: DOMAIN
<222> LOCATION: (219)..(220)
<223> OTHER INFORMATION: Polylinker

<400> SEQUENCE: 30

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Xaa Met Ser Val Arg Thr
    210                 215                 220

Leu Leu Ala Ala Thr Leu Val Ala Gly Ile Ser Val Leu Ala Pro Ala
225                 230                 235                 240

Gly Ile Ala Asn Ala Glu Thr Ser Met Val Ser Thr Ala Ala Ser
                245                 250                 255

Ser Val Glu His Ala Ala Asn Thr Tyr Asp Phe Ala Glu Ala Lys Ser
            260                 265                 270

Gly Ser Ser Ile Pro Ala Lys Val Ala Ala Glu Gln Ala Asn Ser Tyr
        275                 280                 285

Ser Val His Gly Leu Val Thr Ser Leu Ala Val Tyr Gln His Phe Ser
    290                 295                 300

Leu Thr Val Glu Gly Gly Lys Thr Phe Thr Gly Asp Ser Gly Gly
305                 310                 315                 320

Ile Ser Ile Pro Gly Val Ala Val Leu Glu Gly Thr Leu Phe Thr Glu
                325                 330                 335
```

-continued

Asp Leu Gln His Leu Tyr Ser Asp Thr Val Ser Phe Glu Tyr Asn Ala
                340                 345                 350

Val Gly Pro Tyr Leu Asn Ile Asn Phe Phe Asp Ser His Gly Thr Leu
            355                 360                 365

Leu Gly His Val Gln Ser Gly Ser Ile Gly Thr Val Ser Gly Ile Gly
        370                 375                 380

Gly Gly Thr Gly Gly Trp Gln
385                 390

<210> SEQ ID NO 31
<211> LENGTH: 16
<212> TYPE: PRT
<213> ORGANISM: Rhodococcus equi

<400> SEQUENCE: 31

Met Phe Arg Val Gly Arg Pro Ser Lys Ser Ile Ala Val Val Ala Cys
1               5                   10                  15

<210> SEQ ID NO 32
<211> LENGTH: 16
<212> TYPE: PRT
<213> ORGANISM: Rhodococcus equi

<400> SEQUENCE: 32

Ala Val Val Ala Ser Val Leu Cys Phe Leu Ala Leu Gly Gly Thr Lys
1               5                   10                  15

<210> SEQ ID NO 33
<211> LENGTH: 16
<212> TYPE: PRT
<213> ORGANISM: Rhodococcus equi

<400> SEQUENCE: 33

Leu Gly Gly Thr Ala Arg Ala Asn Val Val Ala Pro Ser Ala Trp Lys
1               5                   10                  15

<210> SEQ ID NO 34
<211> LENGTH: 16
<212> TYPE: PRT
<213> ORGANISM: Rhodococcus equi

<400> SEQUENCE: 34

Cys Pro Ser Ala Trp Gly Gly Ala Gln Ser Ala Ala Asp Lys Glu Gly
1               5                   10                  15

<210> SEQ ID NO 35
<211> LENGTH: 16
<212> TYPE: PRT
<213> ORGANISM: Rhodococcus equi

<400> SEQUENCE: 35

Asp Lys Glu Gly Glu Gly Val Thr Leu Gly Gly Val Gly Val Leu Cys
1               5                   10                  15

<210> SEQ ID NO 36
<211> LENGTH: 16
<212> TYPE: PRT
<213> ORGANISM: Rhodococcus equi

<400> SEQUENCE: 36

Val Gly Val Leu Arg Pro His Asn Lys Asp Ala Asp Glu Gln Tyr Cys
1               5                   10                  15

<210> SEQ ID NO 37
<211> LENGTH: 16
<212> TYPE: PRT
<213> ORGANISM: Rhodococcus equi

<400> SEQUENCE: 37

Asp Glu Gln Tyr Thr Val His Gly Val Val Ser Ala Leu Phe Lys
1               5                   10                  15

<210> SEQ ID NO 38
<211> LENGTH: 16
<212> TYPE: PRT
<213> ORGANISM: Rhodococcus equi

<400> SEQUENCE: 38

Ser Ala Leu Phe Tyr Asn His Leu Arg Ile Ser Val Asp Gly Lys
1               5                   10                  15

<210> SEQ ID NO 39
<211> LENGTH: 16
<212> TYPE: PRT
<213> ORGANISM: Rhodococcus equi

<400> SEQUENCE: 39

Lys Val Asp Gly Gly Met Thr Phe Asp Gly Asp Gly Gly Leu Ser
1               5                   10                  15

<210> SEQ ID NO 40
<211> LENGTH: 16
<212> TYPE: PRT
<213> ORGANISM: Rhodococcus equi

<400> SEQUENCE: 40

Gly Gly Leu Ser Thr Pro Gly Gly Ala Leu Trp Gly Thr Leu Lys
1               5                   10                  15

<210> SEQ ID NO 41
<211> LENGTH: 16
<212> TYPE: PRT
<213> ORGANISM: Rhodococcus equi

<400> SEQUENCE: 41

Trp Gly Thr Leu Thr Thr Ser Asp Leu Gln Gln Leu Tyr Asp Glu Lys
1               5                   10                  15

<210> SEQ ID NO 42
<211> LENGTH: 16
<212> TYPE: PRT
<213> ORGANISM: Rhodococcus equi

<400> SEQUENCE: 42

Lys Leu Tyr Asp Glu Thr Ala Ser Phe Glu Cys Asn Ala Val Gly Pro
1               5                   10                  15

<210> SEQ ID NO 43
<211> LENGTH: 16
<212> TYPE: PRT
<213> ORGANISM: Rhodococcus equi

<400> SEQUENCE: 43

Lys Ala Val Gly Pro Tyr Leu Asn Ile Asn Phe Tyr Asp Ser Tyr Gly
1               5                   10                  15

<210> SEQ ID NO 44

```
<211> LENGTH: 16
<212> TYPE: PRT
<213> ORGANISM: Rhodococcus equi

<400> SEQUENCE: 44

Asp Ser Tyr Gly Arg Ile Leu Ala Ser Val Gln Ala Gly Gly Val Lys
1               5                   10                  15

<210> SEQ ID NO 45
<211> LENGTH: 16
<212> TYPE: PRT
<213> ORGANISM: Rhodococcus equi

<400> SEQUENCE: 45

Lys Ala Gly Gly Val Ser Thr Met Ile Gly Ile Gly Gly Gly Asn Gly
1               5                   10                  15

<210> SEQ ID NO 46
<211> LENGTH: 16
<212> TYPE: PRT
<213> ORGANISM: Rhodococcus equi

<400> SEQUENCE: 46

Lys Thr Met Ile Gly Ile Gly Gly Gly Asn Gly Arg Trp His Leu Val
1               5                   10                  15
```